US010138485B2

(12) United States Patent
Khvorova et al.

(10) Patent No.: US 10,138,485 B2
(45) Date of Patent: *Nov. 27, 2018

(54) NEUTRAL NANOTRANSPORTERS

(75) Inventors: Anastasia Khvorova, Westborough, MA (US); William Salomon, Worcester, MA (US); Joanne Kamens, Newton, MA (US); Dmitry Samarsky, Westborough, MA (US); Tod M. Woolf, Sudbury, MA (US); Michelle Miller, Norwood, MA (US); Karen G. Bulock, Mendon, MA (US)

(73) Assignee: RXi Pharmaceuticals Corporation, Marlborough, MA (US)

( * ) Notice: Subject to any disclaimer, the term of this patent is extended or adjusted under 35 U.S.C. 154(b) by 1064 days.

This patent is subject to a terminal disclaimer.

(21) Appl. No.: 13/120,341

(22) PCT Filed: Sep. 22, 2009

(86) PCT No.: PCT/US2009/005251
§ 371 (c)(1),
(2), (4) Date: Jun. 6, 2011

(87) PCT Pub. No.: WO2010/033248
PCT Pub. Date: Mar. 25, 2010

(65) Prior Publication Data
US 2011/0237522 A1    Sep. 29, 2011

Related U.S. Application Data

(60) Provisional application No. 61/192,954, filed on Sep. 22, 2008, provisional application No. 61/149,946, filed on Feb. 4, 2009, provisional application No. 61/224,031, filed on Jul. 8, 2009.

(51) Int. Cl.
*C12N 15/113* (2010.01)
*C12N 15/11* (2006.01)

(52) U.S. Cl.
CPC ........ *C12N 15/1136* (2013.01); *C12N 15/111* (2013.01); *C12N 15/113* (2013.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/3515* (2013.01); *C12N 2310/3519* (2013.01); *C12N 2310/3521* (2013.01); *C12N 2320/32* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 3,737,337 A | 6/1973 | Schnoring et al. |
| 3,891,570 A | 6/1975 | Fukushima et al. |
| 4,201,860 A | 5/1980 | Naito et al. |
| 4,235,871 A | 11/1980 | Papahadjopoulos et al. |
| 4,384,975 A | 5/1983 | Fong |
| 4,389,330 A | 6/1983 | Tice et al. |
| 4,415,732 A | 11/1983 | Caruthers et al. |
| 4,426,330 A | 1/1984 | Sears |
| 4,501,728 A | 2/1985 | Geho et al. |
| 4,652,441 A | 3/1987 | Okada et al. |
| 4,737,323 A | 4/1988 | Martin et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 5,013,556 A | 5/1991 | Woodle et al. |
| 5,023,243 A | 6/1991 | Tullis |
| 5,051,257 A | 9/1991 | Pietronigro |
| 5,053,228 A | 10/1991 | Mori et al. |
| 5,108,921 A | 4/1992 | Low et al. |
| 5,112,963 A | 5/1992 | Pieles et al. |
| 5,149,782 A | 9/1992 | Chang et al. |
| 5,151,510 A | 9/1992 | Stec et al. |
| 5,162,115 A | 11/1992 | Pietronigro |
| 5,188,897 A | 2/1993 | Suhadolnik et al. |
| 5,213,804 A | 5/1993 | Martin et al. |
| 5,227,170 A | 7/1993 | Sullivan |
| 5,264,221 A | 11/1993 | Tagawa et al. |
| 5,264,423 A | 11/1993 | Cohen et al. |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

Boutorin et al., Synthesis of alkylating oligonucleotide derivatives containing cholesterol or phenazinium residues at their 3'-terminus and their interaction with DNA within mammalian cells.FEBS Lett. Aug. 28, 1989;254(1-2): 129-32.*
Hosono, et al. (1995, Biochim. Biophys Acta., v.1244:339-44).*
Alahari, et al. (1996, Mol. Pharma., v.50:808-19).*
Re. 5466786, BI, Buhr et al., Apr. 7, 1998.
[No Author Listed] RedChip Small-Cap Investor Conference. RXI Pharmaceuticals (Nasdaq RXII). Jun. 16, 2009 Presentation. 22 pages.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.

(Continued)

*Primary Examiner* — Maury A Audet
(74) *Attorney, Agent, or Firm* — Wolf, Greenfield & Sacks, P.C.

(57) ABSTRACT

Neutral lipid formulations for nucleic acid delivery are provided according to the invention. The neutral lipid formulations include hydrophobically modified polynucleotides and fat mixtures. Methods of using the neutral lipid formulations are also provided.

15 Claims, 38 Drawing Sheets

Specification includes a Sequence Listing.

(56) References Cited

U.S. PATENT DOCUMENTS

| | | |
|---|---|---|
| 5,264,562 A | 11/1993 | Matteucci |
| 5,284,656 A | 2/1994 | Platz et al. |
| 5,354,844 A | 10/1994 | Beug et al. |
| 5,356,633 A | 10/1994 | Woodle et al. |
| 5,395,619 A | 3/1995 | Zalipsky et al. |
| 5,405,939 A | 4/1995 | Suhadolnik et al. |
| 5,407,609 A | 4/1995 | Tice et al. |
| 5,416,016 A | 5/1995 | Low et al. |
| 5,416,203 A | 5/1995 | Letsinger |
| 5,417,978 A | 5/1995 | Tani et al. |
| 5,432,272 A | 7/1995 | Benner |
| 5,451,569 A | 9/1995 | Wong et al. |
| 5,453,496 A | 9/1995 | Caruthers et al. |
| 5,459,127 A | 10/1995 | Felgner et al. |
| 5,459,255 A | 10/1995 | Cook et al. |
| 5,466,786 A | 11/1995 | Buhr et al. |
| 5,469,854 A | 11/1995 | Unger et al. |
| 5,470,967 A | 11/1995 | Huie et al. |
| 5,486,603 A | 1/1996 | Buhr |
| 5,489,677 A | 2/1996 | Sanghvi et al. |
| 5,491,133 A | 2/1996 | Walder et al. |
| 5,495,009 A | 2/1996 | Matteucci et al. |
| 5,512,295 A | 4/1996 | Kornberg et al. |
| 5,512,439 A | 4/1996 | Homes et al. |
| 5,514,786 A | 5/1996 | Cook et al. |
| 5,525,465 A | 6/1996 | Haralambidis |
| 5,527,528 A | 6/1996 | Allen et al. |
| 5,532,130 A | 7/1996 | Alul |
| 5,534,259 A | 7/1996 | Zalipsky et al. |
| 5,539,082 A | 7/1996 | Nielsen et al. |
| 5,539,083 A | 7/1996 | Cook et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,561,225 A | 10/1996 | Maddry et al. |
| 5,574,142 A | 11/1996 | Meyer, Jr. et al. |
| 5,578,718 A | 11/1996 | Cook et al. |
| 5,580,575 A | 12/1996 | Unger et al. |
| 5,580,731 A | 12/1996 | Chang et al. |
| 5,580,972 A | 12/1996 | Tu et al. |
| 5,583,020 A | 12/1996 | Sullivan |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,595,756 A | 1/1997 | Bally et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,025 A | 8/1997 | Szoka, Jr. et al. |
| 5,661,134 A | 8/1997 | Cook et al. |
| 5,663,312 A | 9/1997 | Chaturvedula |
| 5,670,633 A | 9/1997 | Cook et al. |
| 5,672,662 A | 9/1997 | Harris et al. |
| 5,674,683 A | 10/1997 | Kool |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,780,607 A | 7/1998 | Goodnow, Jr. et al. |
| 5,789,416 A | 8/1998 | Lum et al. |
| 5,792,847 A | 8/1998 | Buhr et al. |
| 5,808,023 A | 9/1998 | Sanghvi et al. |
| 5,808,036 A | 9/1998 | Kool |
| 5,814,014 A | 9/1998 | Elsberry et al. |
| 5,817,781 A | 10/1998 | Swaminathan et al. |
| 5,830,430 A | 11/1998 | Unger et al. |
| 5,830,653 A | 11/1998 | Froehler et al. |
| 5,849,902 A | 12/1998 | Arrow et al. |
| 5,851,548 A | 12/1998 | Dattagupta et al. |
| 5,855,910 A | 1/1999 | Ashley et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,094 A | 12/1999 | Simon et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,025,140 A | 2/2000 | Langel et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,093,180 A | 7/2000 | Elsberry |
| 6,107,094 A | 8/2000 | Crooke |
| 6,111,085 A | 8/2000 | Cook et al. |
| 6,121,437 A | 9/2000 | Guzaev |
| 6,133,229 A | 10/2000 | Gibson et al. |
| 6,153,737 A | 11/2000 | Manoharan et al. |
| 6,207,819 B1 | 3/2001 | Manoharan et al. |
| 6,210,892 B1 | 4/2001 | Bennett et al. |
| 6,221,911 B1 | 4/2001 | Lavin et al. |
| 6,242,594 B1 | 6/2001 | Kelly |
| 6,262,036 B1 | 7/2001 | Arnold, Jr. et al. |
| 6,262,241 B1 | 7/2001 | Cook et al. |
| 6,271,358 B1 | 8/2001 | Manoharan et al. |
| 6,299,895 B1 | 10/2001 | Hammang et al. |
| 6,300,319 B1 | 10/2001 | Manoharan |
| 6,326,358 B1 | 12/2001 | Manoharan |
| 6,331,313 B1 | 12/2001 | Wong et al. |
| 6,331,617 B1 | 12/2001 | Weeks et al. |
| 6,335,434 B1 | 1/2002 | Guzaev et al. |
| 6,344,436 B1 | 2/2002 | Smith et al. |
| 6,346,416 B1 | 2/2002 | Dean et al. |
| 6,355,787 B1 | 3/2002 | Beckvermit et al. |
| 6,358,931 B1 | 3/2002 | Cook et al. |
| 6,372,499 B1 | 4/2002 | Midoux et al. |
| 6,378,526 B1 | 4/2002 | Bowman et al. |
| 6,379,965 B1 | 4/2002 | Boutin |
| 6,395,474 B1 | 5/2002 | Buchardt et al. |
| 6,395,492 B1 | 5/2002 | Manoharan et al. |
| 6,397,849 B1 | 6/2002 | Bowman et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,436,427 B1 | 8/2002 | Hammang et al. |
| 6,440,943 B1 | 8/2002 | Cook et al. |
| 6,444,806 B1 | 9/2002 | Veerapanani et al. |
| 6,465,628 B1 | 10/2002 | Ravikumar et al. |
| 6,476,205 B1 | 11/2002 | Buhr et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,559,279 B1 | 5/2003 | Manoharan et al. |
| 6,656,730 B1 | 12/2003 | Manoharan |
| 6,673,611 B2 | 1/2004 | Thompson et al. |

(56) References Cited

U.S. PATENT DOCUMENTS

| | | |
|---|---|---|
| 6,683,167 B2 | 1/2004 | Metelev et al. |
| 6,794,137 B2 | 9/2004 | Blumenberg |
| 6,815,432 B2 | 11/2004 | Wheeler et al. |
| 6,849,726 B2 | 2/2005 | Usman et al. |
| 6,858,225 B2 | 2/2005 | Semple et al. |
| 6,887,906 B1 | 5/2005 | Teng et al. |
| 7,041,824 B2 | 5/2006 | Bordon-Pallier et al. |
| 7,044,945 B2 | 5/2006 | Sand |
| 7,056,704 B2 | 6/2006 | Tuschl et al. |
| 7,078,196 B2 | 7/2006 | Tuschl et al. |
| 7,108,721 B2 | 9/2006 | Huckle et al. |
| 7,148,342 B2 | 12/2006 | Tolentino et al. |
| 7,205,297 B2 | 4/2007 | Beauchamp et al. |
| 7,405,274 B2 | 7/2008 | Lin et al. |
| 7,432,250 B2 | 10/2008 | Crooke |
| 7,521,431 B2 | 4/2009 | Reich et al. |
| 7,538,095 B2 | 5/2009 | Fire et al. |
| 7,560,438 B2 | 7/2009 | Fire et al. |
| 7,579,186 B1 | 8/2009 | Sakamoto et al. |
| 7,595,387 B2 | 9/2009 | Leake et al. |
| 7,605,251 B2 | 10/2009 | Tan et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 7,838,507 B2 | 11/2010 | Shepard et al. |
| 8,110,674 B2 | 2/2012 | Manoharan et al. |
| 8,193,334 B2 * | 6/2012 | Radovic-Moreno et al. ............... 536/24.5 |
| 8,202,845 B2 | 6/2012 | Drumm et al. |
| 8,263,569 B2 | 9/2012 | Baulcombe et al. |
| 8,268,794 B2 | 9/2012 | Nakajima et al. |
| 8,329,671 B2 | 12/2012 | Gu et al. |
| 8,470,792 B2 | 6/2013 | Frost et al. |
| 8,664,189 B2 | 3/2014 | Khvorova et al. |
| 8,796,443 B2 * | 8/2014 | Khvorova ............ C12N 15/111 536/23.1 |
| 8,815,818 B2 | 8/2014 | Samarsky et al. |
| 9,074,211 B2 * | 7/2015 | Woolf et al. |
| 9,080,171 B2 | 7/2015 | Khvorova et al. |
| 9,095,504 B2 | 8/2015 | Libertine et al. |
| 9,175,289 B2 * | 11/2015 | Khvorova ............ C12N 15/111 |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 2002/0049173 A1 | 4/2002 | Bennett et al. |
| 2002/0081736 A1 | 6/2002 | Conroy et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0027780 A1 | 2/2003 | Hardee et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0148979 A1 | 8/2003 | Sosnowski et al. |
| 2003/0153524 A1 | 8/2003 | Hinton et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2004/0009938 A1 | 1/2004 | Manoharan et al. |
| 2004/0014956 A1 | 1/2004 | Woolf et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0072785 A1 | 4/2004 | Wolff et al. |
| 2004/0102618 A1 | 5/2004 | Crooke et al. |
| 2004/0137471 A1 | 7/2004 | Vickers et al. |
| 2004/0162235 A1 | 8/2004 | Trubetskoy et al. |
| 2004/0167090 A1 | 8/2004 | Manoharan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0219520 A1 | 11/2004 | Mirkin et al. |
| 2004/0229266 A1 | 11/2004 | Tuschl et al. |
| 2004/0235031 A1 | 11/2004 | Schultz et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0008617 A1 | 1/2005 | Chen et al. |
| 2005/0020521 A1 | 1/2005 | Rana |
| 2005/0032733 A1 * | 2/2005 | McSwiggen et al. ........... 514/44 |
| 2005/0037496 A1 | 2/2005 | Rozema et al. |
| 2005/0042227 A1 | 2/2005 | Zankel et al. |
| 2005/0064595 A1 | 3/2005 | MacLachlan et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0175682 A1 | 8/2005 | Heyes et al. |
| 2005/0181382 A1 | 8/2005 | Zamore et al. |
| 2005/0222071 A1 | 10/2005 | Duranton et al. |
| 2005/0239731 A1 | 10/2005 | McSwiggen et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2005/0265957 A1 | 12/2005 | Monahan et al. |
| 2005/0281781 A1 | 12/2005 | Ostroff |
| 2006/0008910 A1 | 1/2006 | MacLachlan et al. |
| 2006/0009409 A1 | 1/2006 | Woolf |
| 2006/0025363 A1 | 2/2006 | Breitenbach et al. |
| 2006/0035344 A1 | 2/2006 | Pachuk et al. |
| 2006/0069050 A1 * | 3/2006 | Rana ............... C12N 15/111 514/44 A |
| 2006/0127891 A1 | 6/2006 | McSwiggen et al. |
| 2006/0142228 A1 | 6/2006 | Ford et al. |
| 2006/0160766 A1 | 7/2006 | Cheung |
| 2006/0178324 A1 | 8/2006 | Hadwiger et al. |
| 2006/0178327 A1 | 8/2006 | Yeung |
| 2006/0188506 A1 | 8/2006 | Cheung |
| 2006/0234970 A1 | 10/2006 | Jimenez |
| 2006/0240093 A1 | 10/2006 | MacLachlan et al. |
| 2007/0020623 A1 | 1/2007 | Petersohn et al. |
| 2007/0031844 A1 * | 2/2007 | Khvorova ............ A61K 31/713 435/6.11 |
| 2007/0032441 A1 | 2/2007 | McSwiggen et al. |
| 2007/0166734 A1 | 7/2007 | Bhat et al. |
| 2007/0173473 A1 | 7/2007 | McSwiggen et al. |
| 2007/0173476 A1 * | 7/2007 | Leake ............... C12N 15/111 514/44 A |
| 2007/0231392 A1 | 10/2007 | Wagner et al. |
| 2007/0269889 A1 | 11/2007 | Leake et al. |
| 2008/0038296 A1 | 2/2008 | Brahmbhatt et al. |
| 2008/0071068 A1 | 3/2008 | Oba et al. |
| 2008/0085869 A1 | 4/2008 | Yamada et al. |
| 2008/0107694 A1 | 5/2008 | Trogden et al. |
| 2008/0125386 A1 * | 5/2008 | Rana et al. ............... 514/44 |
| 2008/0152654 A1 | 6/2008 | Reich |
| 2008/0152661 A1 | 6/2008 | Rozema et al. |
| 2008/0311040 A1 | 12/2008 | Berry et al. |
| 2009/0012021 A1 | 1/2009 | Sood et al. |
| 2009/0023216 A1 | 1/2009 | Woolf |
| 2009/0131360 A1 | 5/2009 | Woolf et al. |
| 2009/0171075 A1 | 7/2009 | Li |
| 2009/0182136 A1 | 7/2009 | Wengel et al. |
| 2009/0186802 A1 | 7/2009 | Alluis et al. |
| 2009/0202520 A1 | 8/2009 | Lupher, Jr. et al. |
| 2009/0208564 A1 | 8/2009 | Li et al. |
| 2009/0239814 A1 | 9/2009 | Manoharan et al. |
| 2009/0239934 A1 | 9/2009 | Schmitt-Milas |
| 2009/0247608 A1 * | 10/2009 | Manoharan ...... A61K 47/48092 514/44 A |
| 2009/0306005 A1 | 12/2009 | Bhanot et al. |
| 2010/0010082 A1 | 1/2010 | Chong et al. |
| 2010/0040656 A1 | 2/2010 | Franklin et al. |
| 2010/0069620 A1 | 3/2010 | Zon |
| 2010/0136695 A1 | 6/2010 | Woolf |

(56) References Cited

U.S. PATENT DOCUMENTS

| | | | |
|---|---|---|---|
| 2010/0196482 A1* | 8/2010 | Radovic-Moreno et al. | 514/44 A |
| 2011/0021605 A1 | 1/2011 | Schulte et al. | |
| 2011/0039914 A1 | 2/2011 | Pavco et al. | |
| 2011/0054004 A1 | 3/2011 | Mustoe et al. | |
| 2011/0237522 A1* | 9/2011 | Khvorova et al. | 514/20.9 |
| 2011/0237648 A1 | 9/2011 | Khvorova et al. | |
| 2011/0251258 A1 | 10/2011 | Samarsky et al. | |
| 2011/0263680 A1 | 10/2011 | Khvorova et al. | |
| 2012/0016005 A1 | 1/2012 | Samarsky et al. | |
| 2012/0040459 A1 | 2/2012 | Khvorova et al. | |
| 2012/0059046 A1* | 3/2012 | Woolf et al. | 514/44 A |
| 2012/0065243 A1 | 3/2012 | Woolf et al. | |
| 2013/0131141 A1 | 5/2013 | Khvorova et al. | |
| 2013/0131142 A1 | 5/2013 | Libertine et al. | |
| 2013/0197055 A1 | 8/2013 | Kamens et al. | |
| 2014/0113950 A1 | 4/2014 | Khvorova et al. | |
| 2014/0315974 A1 | 10/2014 | Khvorova et al. | |
| 2014/0364482 A1 | 12/2014 | Khvorova et al. | |
| 2016/0244765 A1 | 8/2016 | Khvorova et al. | |
| 2016/0304873 A1 | 10/2016 | Wolfson et al. | |
| 2016/0304875 A1 | 10/2016 | Cauwenbergh et al. | |
| 2016/0319278 A1 | 11/2016 | Khvorova et al. | |
| 2016/0355808 A1 | 12/2016 | Khvorova et al. | |
| 2016/0355826 A1 | 12/2016 | Khvorova et al. | |
| 2017/0009239 A1 | 1/2017 | Khvorova et al. | |
| 2017/0022501 A1 | 1/2017 | Dean et al. | |
| 2017/0051288 A1 | 2/2017 | Byrne et al. | |
| 2017/0051290 A1 | 2/2017 | Byrne et al. | |
| 2017/0067056 A1 | 3/2017 | Khvorova et al. | |
| 2017/0137823 A1 | 5/2017 | Kamens et al. | |

FOREIGN PATENT DOCUMENTS

| | | |
|---|---|---|
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | 4 095 895 B2 | 9/2004 |
| JP | 2009-519033 | 5/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 98/14172 A1 | 4/1998 |
| WO | WO 99/13915 A1 | 3/1999 |
| WO | WO 00/03683 A2 | 1/2000 |
| WO | WO 03/012052 A2 | 2/2003 |
| WO | WO 2003/064626 A2 | 8/2003 |
| WO | WO 2003/087367 A2 | 10/2003 |
| WO | WO 2003/087368 A2 | 10/2003 |
| WO | WO 2004/064760 A2 | 8/2004 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/019453 A2 | 3/2005 |
| WO | WO 2005/024033 A2 | 3/2005 |
| WO | WO 2005/079533 A2 | 9/2005 |
| WO | WO 2005/097992 A2 | 10/2005 |
| WO | WO 2006/007372 A2 | 1/2006 |
| WO | WO 2006/019430 A2 | 2/2006 |
| WO | WO 2006/039656 A2 | 4/2006 |
| WO | WO 2006/065601 A2 | 6/2006 |
| WO | WO 2006/113679 A2 | 10/2006 |
| WO | WO 2006/128141 A2 | 11/2006 |
| WO | WO 2007/021142 A1 | 2/2007 |
| WO | WO 2007/030167 A1 | 3/2007 |
| WO | WO 2007/050643 A2 | 5/2007 |
| WO | WO 2007/069068 A2 | 6/2007 |
| WO | WO 2007/089607 A2 | 8/2007 |
| WO | WO 2008/021157 A1 | 2/2008 |
| WO | WO 2008/036825 A2 | 3/2008 |
| WO | WO 2008/109353 A1 | 9/2008 |
| WO | WO 2008/125908 A2 | 10/2008 |
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/126933 A2 | 10/2009 |
| WO | WO 2010/006237 A2 | 1/2010 |
| WO | WO 2010/011346 A1 | 1/2010 |
| WO | WO 2010/027830 A2 | 3/2010 |
| WO | WO 2010/027831 A1 | 3/2010 |
| WO | WO 2010/027832 A1 | 3/2010 |
| WO | WO 2010/042281 A2 | 4/2010 |
| WO | WO 2010/135207 A1 | 11/2010 |
| WO | WO 2011/109698 A1 | 9/2011 |

OTHER PUBLICATIONS

Akinc et al., Development of lipidoid-siRNA formulations for systemic delivery to the liver. Mol Ther. May 2009;17(5):872-9. doi: 10.1038/mt.2009.36. Epub Mar. 3, 2009.

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.

Aleckovic et al., RNAi at Oxford. J RNAi Gene Silencing. May 27, 2008;4(1):266-8.

Baigude et al., Design and creation of new nanomaterials for therapeutic RNAi. ACS Chem Biol. Apr. 24, 2007;2(4):237-41.

Beier et al., Kinetics of particle uptake in the domes of Peyer's patches. Am J Physiol. Jul. 1998;275(1 Pt 1):G130-7.

Bongartz et al., Improved biological activity of antisense oligonucleotides conjugated to a fusogenic peptide. Nucleic Acids Res. Nov. 1994 11;22(22):4681-8.

Boussif et al., Optimized galenics improve in vitro gene transfer with cationic molecules up to 1000-fold. Gene Ther. Dec. 1996;3(12):1074-80.

Chui et al., Visualizing a correlation between siRNA localization, cellular uptake, and RNAi in living cells. Chem Biol. Aug. 2004;11(8):1165-75.

Chu et al., Potent RNAi by short RNA triggers. RNA. 2008;14:1714-9.

Clark et al., Exploiting M cells for drug and vaccine delivery. Adv Drug Deliv Rev. Aug. 23, 2001;50(1-2):81-106.

Clark et al., Targeting polymerised liposome vaccine carriers to intestinal M cells. Vaccine. Oct. 12, 2001;20(1-2):208-17.

Crombez et al., A non-covalent peptide-based strategy for siRNA delivery. Biochem Soc Trans. Feb. 2007;35(Pt 1):44-6. Review.

De Smidt et al., Association of antisense oligonucleotides with lipoproteins prolongs the plasma half-life and modifies the tissue distribution. Nucleic Acids Res. Sep. 11, 1991;19(17):4695-700.

Diebold et al., Mannose receptor-mediated gene delivery into antigen presenting dendritic cells. Somat Cell Mol Genet. Nov. 2002;27(1-6):65-74. Review.

Fajac et al., Uptake of plasmid/glycosylated polymer complexes and gene transfer efficiency in differentiated airway epithelial cells. J Gene Med. 2003;5(1):38-48.

Felgner et al., Lipofection: a highly efficient, lipid-mediated DNA-transfection procedure. Proc Natl Acad Sci U S A. Nov. 1987;84(21):7413-7.

Flanagan et al., A cytosine analog that confers enhanced potency to antisense oligonucleotides. Proc Natl Acad Sci U S A. Mar. 30, 1999;96(7):3513-8.

Floch et al., Cationic phosphonolipids as non viral vectors for DNA transfection in hematopoietic cell lines and CD34+ cells. Blood Cells Mol Dis. 1997;23(1):69-87.

(56) References Cited

OTHER PUBLICATIONS

Florence, The oral absorption of micro- and nanoparticulates: neither exceptional nor unusual. Pharm Res. Mar. 1997;14(3):259-66.
Frank-Kamenetsky et al., Therapeutic RNAi targeting PCSK9 acutely lowers plasma cholesterol in rodents and LDL cholesterol in non-human primates. Proc Natl Acad Sci U S A. Aug. 19, 2008;105(33):11915-20. doi: 10.1073/pnas.0805434105. Epub Aug. 11, 2008.
Fritz et al., Gene transfer into mammalian cells using histone-condensed plasmid DNA. Hum Gene Ther. Aug. 1, 1997;7(12):1395-404.
Fuhrhop et al., Bolaamphiphiles with mannose- and tetraalkylammonium head groups as coatings for nucleic acids and possible reagents for transfections. Chem Phys Lipids. 1987;43(3):193-213.
Funhoff et al., Endosomal escape of polymeric gene delivery complexes is not always enhanced by polymers buffering at low pH. Biomacromolecules. Jan.-Feb. 2004;5(1):32-9.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Goldman et al., In vitro and in vivo gene delivery mediated by a synthetic polycationic amino polymer. Nat Biotechnol. May 1997;15(5):462-6.
Gottschalk et al., A novel DNA-peptide complex for efficient gene transfer and expression in mammalian cells. Gene Ther. May 1996;3(5):448-57.
Grosse et al., In vivo gene delivery in the mouse lung with lactosylated polyethylenimine, questioning the relevance of in vitro experiments. J Control Release. Dec. 8, 2008;132(2):105-12. Epub Sep. 4, 2008.
Haensler et al., Polyamidoamine cascade polymers mediate efficient transfection of cells in culture. Bioconjug Chem. Sep.-Oct. 1993;4(5):372-9.
Hashimoto et al., Gene transfer by DNA/mannosylated chitosan complexes into mouse peritoneal macrophages. Biotechnol Lett. Jun. 2006;28(11):815-21. Epub May 31, 2006.
Hope et al., Cationic lipids, phosphatidylethanolamine and the intracellular delivery of polymeric, nucleic acid-based drugs (review). Mol Membr Biol. 1998; Jan.-Mar.;15(1):1-14.
Huang et al., Lipitoids—novel cationic lipids for cellular delivery of plasmid DNA in vitro. Chem Biol. Jun. 1998;5(6):345-54.
Ihre et al., Fast and convenient divergent synthesis of aliphatic ester dendrimers by anhydride coupling. J Am Chem Soc. Jun. 27, 2001;123(25):5908-17.
Jaschke et al., Automated Incorporation of Polyethylene Glycol into Synthetic Oligonucleotides, Tetra. Lett. Jan. 1993;34(2) :301-304.
Jiang et al., Mannosylated chitosan-graft-polyethylenimine as a gene carrier for Raw 264.7 cell targeting. Int J Pharm. Jun. 2007 22;375(1-2):133-9. Epub Apr. 5, 2009.
Kamata et al., Amphiphilic peptides enhance the efficiency of liposome-mediated DNA transfection. Nucleic Acids Res. Feb. 11, 1994;22(3):536-7.
Kawasaki et al., Uniformly modified 2'-deoxy-2'-fluoro phosphorothioate oligonucleotides as nuclease-resistant antisense compounds with high affinity and specificity for RNA targets. J Med Chem. Apr. 2, 1993;36(7):831-41.
Kichler, Gene transfer with modified polyethylenimines J Gene Med. Feb. 2004;6 Suppl 1:S3-10. Review.
Kim et al., Systemic and specific delivery of small interfering RNAs to the liver mediated by apolipoprotein A-I. Mol Ther. Jun. 2007;15(6):1145-52. Epub Apr. 17, 2007.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. RNA. May 2004;10(5):766-71.
Legendre et al., Dioleoylmelittin as a novel serum-insensitive reagent for efficient transfection of mammalian cells. Bioconjug Chem. Jan.-Feb. 1997;8(1):57-63.
Lemaitre et al., Specific antiviral activity of a poly(L-lysine)-conjugated oligodeoxyribonucleotide sequence complementary to vesicular stomatitis virus N protein mRNA initiation site. Proc Natl Acad Sci U S A. Feb. 1987;84(3):648-52.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Surface-modified LPD nanoparticles for tumor targeting. Ann N Y Acad Sci. Oct. 2006;1082:1-8.
Liang et al., Oligonucleotide delivery: a cellular prospective. Pharmazie. Aug. 1999;54(8):559-66.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Medarova et al., In vivo imaging of siRNA delivery and silencing in tumors. Nat Med. Mar. 2007;13(3):372-7. Epub Feb. 25, 2007.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Milhem et al, Polyamidoamine Starburst dendrimers as solubility enhancers. Int J Pharm. Mar. 20, 2000;197(1-2):239-41.
Mistry et al., Recombinant HMG1 protein produced in Pichia pastoris: a nonviral gene delivery agent. Biotechniques. Apr. 1997;22(4):718-29.
Murphy et al., A combinatorial approach to the discovery of efficient cationic peptoid reagents for gene delivery. Proc Natl Acad Sci U S A. Feb. 17, 1998;95(4):1517-22.
Nakase et al., Biodegradable microspheres targeting mucosal immune-regulating cells: new approach for treatment of inflammatory bowel disease. J Gastroenterol. Mar. 2003;38 Suppl 15:59-62.
Oberhauser et al., Effective incorporation of 2'-O-methyl-oligoribonucleotides into liposomes and enhanced cell associationthrough modification with thiocholesterol. Nucleic Acids Res. Feb. 11, 1992;20(3):533-8.
Olejnik et al., Photocleavable biotin phosphoramidite for 5'-end-labeling, affinity purification and phosphorylation of synthetic oligonucleotides. Nucleic Acids Res. Jan. 15, 1996;24(2):361-6.
Opalinska et al., Nucleic-acid therapeutics: basic principles and recent applications. Nat Rev Drug Discov. Jul. 2002;1(7):503-14.
Park et al., Mannosylated polyethylenimine coupled mesoporous silica nanoparticles for receptor-mediated gene delivery. Int J Pharm. Jul. 9, 2008;359(1-2):280-7. Epub Apr. 12, 2008.
Rozema et al., Dynamic PolyConjugates for targeted in vivo delivery of siRNA to hepatocytes. Proc Natl Acad Sci U S A. Aug. 7, 2007; 104(32): 12982-12987.
Rump et al., Preparation of conjugates of oligodeoxynucleotides and lipid structures and their interaction with low-density lipoprotein. Bioconjug Chem. May-Jun. 1998;9(3):341-9.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Schaniel et al., Delivery of short hairpin RNAs—triggers of gene silencing—into mouse embryonic stem cells. Nat Methods. May 2006;3(5):397-400.
Schell et al., Uptake of polynucleotides by mammalian cells. XIV. Stimulation of the uptake of polynucleotides by poly(L-lysine). Biochim Biophys Acta. Mar. 27, 1974;340(3):323-33.

(56) References Cited

OTHER PUBLICATIONS

Smith et al., Pulmonary deposition and clearance of aerosolized alpha-1-proteinase inhibitor administered to dogs and to sheep. J Clin Invest. Oct. 1989;84(4):1145-54.

Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.

Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.

Soutschek et al., Therapeutic silencing of an endogenous gene by systemic administration of modified siRNAs. Nature. Nov. 11, 2004;432(7014):173-8.

Sun et al., Asymmetric RNA duplexes mediate Rna interference in mammalian cells. Nat Biotechnol. Dec. 2008;26(12):1379-82. doi: 10.1038/nbt.1512. Epub Nov. 23, 2008.

Takanashi et al., Therapeutic silencing of an endogenous gene by siRNA cream in an arthritis model mouse. Gene Ther. Aug. 2009;16(8):982-9. doi:10.1038/gt.2009.66. Epub May 28, 2009.

Tan et al., Quantum-dot based nanoparticles for targeted silencing of HER2/neu gene via RNA interference. Biomaterials. Mar. 2007;28(8):1565-71. Epub Dec. 11, 2006.

Tang et al., In vitro gene delivery by degraded polyamidoamine dendrimers. Bioconjug Chem. Nov.-Dec. 1997;7(6):703-14.

Van Der Lubben et al., Transport of chitosan microparticles for mucosal vaccine delivery in a human intestinal M-cell model. J Drug Target. Sep. 2002;10(6):449-56.

Vlassov et al., Transport of oligonucleotides across natural and model membranes. Biochim Biophys Acta. Jun. 29, 1994;1197(2):95-108.

Wadhwa Peptide-mediated gene delivery: influence of peptide structure on gene expression. Bioconjug Chem. Jan.-Feb. 1997;8(1):81-8.

Wagner et al., DNA-binding transferrin conjugates as functional gene-delivery agents: synthesis by linkage of polylysine or ethidium homodimer to the transferrin carbohydrate moiety. Bioconjug Chem. Jul.-Aug. 1991;2(4):226-31.

Wolfrum et al., Mechanisms and optimization of in vivo delivery of lipophilic siRNAs. Nat Biotechnol. Oct. 2007;25(10):1149-57. Epub Sep. 16, 2007.

Wu et al., Receptor-mediated in vitro gene transformation by a soluble DNA carrier system. J Biol Chem. Apr. 5, 1987;262(10):4429-32.

Wu et al., Durable protection from Herpes Simplex Virus-2 transmission following intravaginal application of siRNAs targeting both a viral and host gene. Cell Host Microbe. Jan. 22, 2009;5(1):84-94. doi:10.1016/j.chom.2008.12.003.

Wyman et al., Design, synthesis, and characterization of a cationic peptide that binds to nucleic acids and permeabilizes bilayers. Biochemistry. Mar. 11, 1997;36(10):3008-17.

Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.

Zhou et al., Lipophilic polylysines mediate efficient DNA transfection in mammalian cells. Biochim Biophys Acta. May 31, 1991;1065(1):8-14.

Zhou et al., Controlled release of PEI/DNA complexes from mannose-bearing chitosan microspheres as a potent delivery system to enhance immune response to HBV DNA vaccine. J Control Release. Aug. 28, 2007;121(3):200-7. Epub May 25, 2007.

Zimmermann et al., RNAi-mediated gene silencing in non-human primates. Nature. May 4, 2006;441(7089):111-4. Epub Mar. 26, 2006.

[No Author Listed], RXI Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

Bertrand et al., Comparison of antisense oligonucleotides and siRNAs in cell culture and in vivo. Biochem Biophys Res Commun. Aug. 30, 2002;296(4):1000-4.

Braasch et al., RNA interference in mammalian cells by chemically-modified RNA. Biochemistry. Jul. 8, 2003;42(26):7967-75.

Brown et al., RNAi off-targeting: Light at the end of the tunnel. J RNAi Gene Silencing. Jul. 28, 2006;2(2):175-7.

Chiu et al., siRNA function in RNAi: a chemical modification analysis. RNA. Sep. 2003;9(9):1034-48.

Choung et al., Chemical modification of siRNAs to improve serum stability without loss of efficacy. Biochem Biophys Res Commun. Apr. 14, 2006;342(3):919-27.

Czauderna et al., Structural variations and stabilising modifications of synthetic siRNAs in mammalian cells. Nucleic Acids Res. Jun. 1, 2003;31(11):2705-16.

Elbashir et al., Duplexes of 21-nucleotide RNAs mediate RNA interference in cultured mammalian cells. Nature. May 24, 2001;411(6836):494-8.

Elbashir et al., Functional anatomy of siRNAs for mediating efficient RNAi in Drosophila melanogaster embryo lysate. EMBO J. Dec. 3, 2001;20(23):6877-88.

Fedorov et al., Off-target effects by siRNA can induce toxic phenotype. RNA. Jul. 2006;12(7):1188-96. Epub May 8, 2006.

Ferentz et al., Disulfide-crosslinked oligonucleotides. Journal of the American Chemical Society. 1991;113 (10): 4000-4002.

Jackson et al., Position-specific chemical modification of siRNAs reduces "off-target" transcript silencing. RNA. Jul. 2006;12(7):1197-1205. Epub May 8, 2006.

Kim et al., Synthetic dsRNA Dicer substrates enhance RNAi potency and efficacy. Nat Biotechnol. Feb. 2005;23(2):222-6. Epub Dec. 26, 2004.

Lee et al., Contributions of 3'-overhang to the dissociation of small interfering RNAs from the PAC domain: molecular dynamics simulation study. J Mol Graph Model. Mar. 2007;25(6):784-93. Epub Jul. 11, 2006.

Leuschner et al., Cleavage of the siRNA passenger strand during RISC assembly in human cells. EEMBO Reports 2006;7(3):314-20.

Macrae et al., Structure of Dicer and mechanistic implications for RNAi. Cold Spring Harb Symp Quant Biol. 2006;71:73-80.

Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.

Murchison et al., Characterization of Dicer-deficient murine embryonic stem cells. Proc Natl Acad Sci U S A. Aug. 23, 2005;102(34):12135-40. Epub Aug. 12, 2005.

Overhoff et al., Phosphorothioate-stimulated uptake of short interfering RNA by human cells. EMBO Rep. Dec. 2005;6(12):1176-81.

Parrish et al., Functional anatomy of a dsRNA trigger: differential requirement for the two trigger strands in RNA interference. Mol Cell. Nov. 2000;6(5):1077-87.

Rajeev et al., 2'-modified-2-thiothymidine oligonucleotides. Org Lett. Aug. 21, 2003;5(17):3005-8.

Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.

Schell et al., Stimulation of the uptake of polynucleotides by poly(L-lysine). Biochim Biophys Acta. Mar. 27, 1974;340(3):323-33.

Seela et al., Oligodeoxyribonucleotides containing 1,3-propanediol as nucleoside substitute. Nucleic Acids Res. Apr. 10, 1987;15(7):3113-29.

Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

[No Author Listed] RXI Pharmaceuticals Completes Apthera Acquisition. Press Release. BusinessWire. Apr. 14, 2011. 2 pages.

[No Author Listed] RXI Pharmaceutical Corporation. Ex 99.1. OTC: RXII. Mar. 2013. 38 pages.

(56) References Cited

OTHER PUBLICATIONS

Augustyns et al., Incorporation of hexose nucleoside analogues into oligonucleotides: synthesis, base-pairing properties and enzymatic stability. Nucleic Acids Res. Sep. 25, 1992;20(18):4711-6.

Bunnell et al., Targeted delivery of antisense oligonucleotides by molecular conjugates. Somat Cell Mol Genet. Nov. 1992;18(6):559-69.

Byrne et al., Novel hydrophobically modified asymmetric RNAi compounds (sd-rxRNA) demonstrate robust efficacy in the eye. J Ocul Pharmacol Ther. Dec. 2013;29(10):855-64. doi: 10.1089/jop.2013.0148. Epub Nov. 1, 2013.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Distler et al., Imatinib mesylate reduces production of extracellular matrix and prevents development of experimental dermal fibrosis. Arthritis Rheum. Jan. 2007;56(1):311-22.

Dziadzio et al., N-terminal connective tissue growth factor is a marker of the fibrotic phenotype in scleroderma. QJM. Jul. 2005;98(7):485-92. Epub Jun. 13, 2005.

Fisher et al., Intracellular disposition and metabolism of fluorescently-labeled unmodified and modified oligonucleotides microinjected into mammalian cells. Nucleic Acids Res. Aug. 11, 1993;21(16):3857-65.

Guo et al., Toll-like receptor 2 siRNA suppresses corneal inflammation and attenuates Aspergillus fumigatus keratitis in rats. Immunol Cell Biol. Mar. 2012;90(3):352-7. doi: 10.1038/icb.2011.49. Epub Jun. 7, 2011.

Hao et al., Electrically assisted delivery of macromolecules into the corneal epithelium. Exp Eye Res. Dec. 2009;89(6):934-41. doi: 10.1016/j.exer.2009.08.001. Epub Aug. 12, 2009.

Hao et al., Gene delivery to cornea. Brain Res Bull. Feb. 15, 2010;81(2-3):256-61. doi: 10.1016/j.brainresbull.2009.06.011. Epub Jun. 26, 2009. Review.

Hinton et al., Novel growth factors involved in the pathogenesis of proliferative vitreoretinopathy. Eye (Lond). Jul. 2002;16(4):422-8.

Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.

Ito et al., Expression of connective tissue growth factor in human renal fibrosis. Kidney Int. Apr. 1998;53(4):853-61.

Leask et al., Insights into the molecular mechanism of chronic fibrosis: the role of connective tissue growth factor in scleroderma. J Invest Dermatol. Jan. 2004;122(1):1-6.

Li et al., A new approach of delivering siRNA to the cornea and its application for inhibiting herpes simplex keratitis. Curr Mol Med. 2014;14(9):1215-25. Database Embase Abstract only. Accession No. EMB-2015893176.

Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.

Rozners et al., Expanding functionality of RNA: synthesis and properties of RNA containing imidazole modified tandem G-U wobble base pairs. Chem Commun (Camb). Dec. 14, 2005;(46):5778-80.

Sato et al., Serum levels of connective tissue growth factor are elevated in patients with systemic sclerosis: association with extent of skin sclerosis and severity of pulmonary fibrosis. J Rheumatol. Jan. 2000;27(1):149-54.

Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008.01.002.

Sisco et al., Antisense inhibition of connective tissue growth factor (CTGF/CCN2) mRNA limits hypertrophic scarring without affecting wound healing in vivo. Wound Repair Regen. Sep.-Oct. 2008;16(5):661-73. doi: 10.1111/j.1524-475X.2008.00416.x.

Snead et al., RNA interference trigger variants: getting the most out of RNA for RNA interference-based therapeutics. Nucleic Acid Ther. Jun. 2012;22(3):139-46. doi: 10.1089/nat.2012.0361. Review.

Sriram et al., Reduction of corneal scarring in rabbits by targeting the TGFB1 pathway with a triple siRNA combination. Adv Biosci Biotechnol. Jan. 1, 2013;4(10):47-55.

Sriram et al., Triple combination of siRNAs targeting TGFβ1, TGFβR2, and CTGF enhances reduction of collagen I and smooth muscle actin in corneal fibroblasts. Invest Ophthalmol Vis Sci. Dec. 17, 2013;54(13):8214-23. doi: 10.1167/iovs.13-12758.

Toyono et al., Angiopoietin-like protein 2 is a potent hemangiogenic and lymphangiogenic factor in corneal inflammation. Invest Ophthalmol Vis Sci. Jun. 26, 2013;54(6):4278-85. doi: 10.1167/iovs.12-11497.

Vermeulen et al., The contributions of dsRNA structure to Dicer specificity and efficiency. RNA. May 2005;11(5):674-82. Epub Apr. 5, 2005.

Bartzatt, Cotransfection of nucleic acid segments by Sendai virus envelopes. Biotechnol Appl Biochem. Feb. 1989;11(1):133-5.

Bergan et al., Electroporation enhances c-myc antisense oligodeoxynucleotide efficacy. Nucleic Acids Res. Jul. 25, 1993;21(15):3567-73.

Bjergarde et al., Solid phase synthesis of oligodeoxyribonucleoside phosphorodithioates from thiophosphoramidites. Nucleic Acids Res. Nov. 11, 1991;19(21):5843-50.

Caruthers et al., Chemical and biochemical studies with dithioate DNA. Nucleosides & Nucleotides. 1991;10(1-3):47-59.

Constantinides et al., Formulation and intestinal absorption enhancement evaluation of water-in-oil microemulsions incorporating medium-chain glycerides. Pharm Res. Oct. 1994;11(10):1385-90.

Debart et al., Chemical modifications to improve the cellular uptake of oligonucleotides. Curr Top Med Chem. 2007;7(7):727-37.

Dykxhoorn et al., The silent treatment: siRNAs as small molecule drugs. Gene Ther. Mar. 2006;13(6):541-52.

Ho et al., Preparation of microemulsions using polyglycerol fatty acid esters as surfactant for the delivery of protein drugs. J Pharm Sci. Feb. 1996;85(2):138-43.

Martins et al., Sterol side chain length and structure affect the clearance of chylomicron-like lipid emulsions in rats and mice. J Lipid Res. Feb. 1998;39(2):302-12.

Reichhart et al., Splice-activated UAS hairpin vector gives complete RNAi knockout of single or double target transcripts in Drosophila melanogaster. Genesis. Sep.-Oct. 2002;34(1-2):160-4.

Shen, Advances in the development of siRNA-based therapeutics for cancer. IDrugs. Aug. 2008;11(8):572-8.

Shi, Mammalian RNAi for the masses. Trends Genet. Jan. 2003;19(1):9-12.

Sui et al., A DNA vector-based RNAi technology to suppress gene expression in mammalian cells. Proc Natl Acad Sci U S A. Apr. 16, 2002;99(8):5515-20.

Tomari et al., Perspective: machines for RNAi. Genes Dev. Mar. 1, 2005;19(5):517-29.

Uhlmann et al., Antisense oligonucleotides: a new therapeutic principle. Chem Rev. 1990;90(4):543-84.

Wagner et al., Transferrin-polycation-DNA complexes: the effect of polycations on the structure of the complex and DNA delivery to cells. Proc Natl Acad Sci U S A. May 15, 1991;88(10):4255-9.

Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.

U.S. Appl. No. 13/636,755, filed Sep. 24, 2012, Khvorova et al.

PCT/US2009/005251, Jan. 18, 2010, Invitation to Pay Additional Fees.

PCT/US2009/005251, Apr. 16, 2010, International Search Report and Written Opinion.

PCT/US2009/005251, Mar. 31, 2011, International Preliminary Report on Patentability.

* cited by examiner

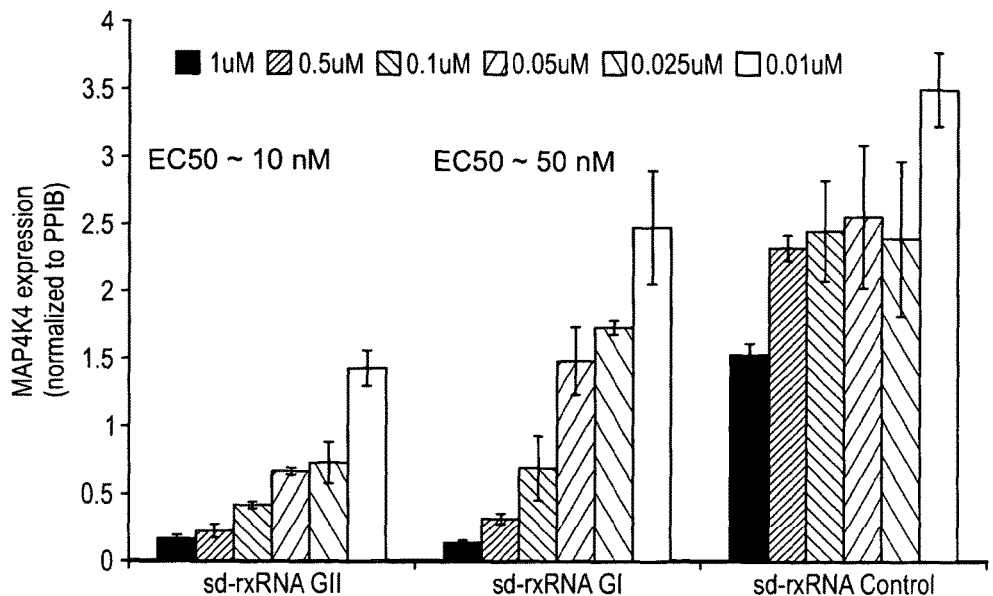
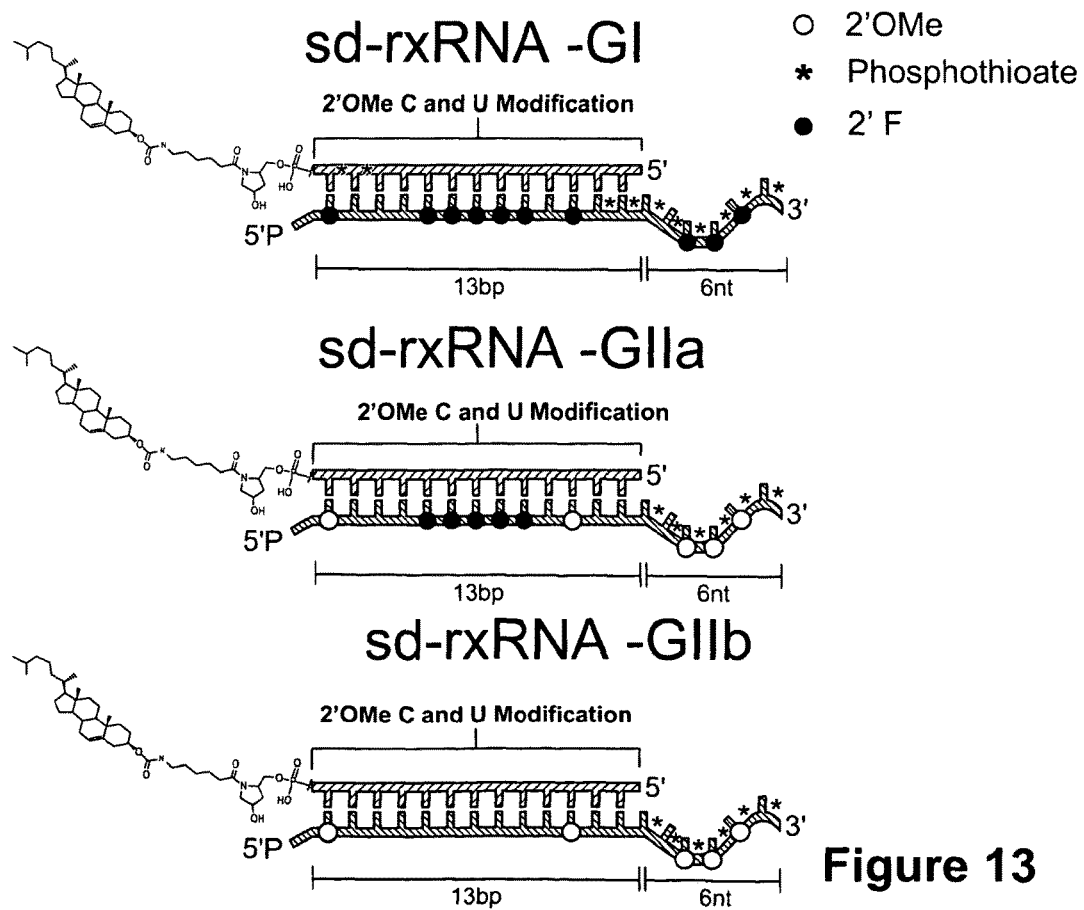
Figure 13 rxRNA$^{ori}$ 25mer with cholesterol based on Map4k4 lead (11546)
- SS: 5' -P.mC.mU.mU.mU.mG.mA.mA.mG.mA.mG.mU.mU.C.U.G.mU.mG.
  mG.mA.mA.mG.mU.mC.mU.mA-Chol-3'
- AS: 5' -U.A.G.A.C.U.U.C.C.A.C.A.G.A.A.C.U.C.U.U.C.A.A.A.G-3' AND    5'-
  U.A.G.A.C.U.U.C.C.A.C.A.G.A.A.C.U.C.U*U*C*A*A*A*G-3'

Antagomir-122 (Stoffel paper)
- 5' -mA*mC*mA.mA.mA.mC.mA.mC.mC.mA.mU.mU.mG.mU.mC.mA.mC.
  mA.mC.mU*mC*mC*mA*-Chol-3' sd-rxRNA with lipid tail in place of cholesterol
- SS based off 12474 with lipid tail in place of cholesterol
      5'-mC.mU.G.mU.G.G.A.A.G.mU.mC.mU.A.-Fatty Acid-3'
- Duplex with AS 12755)

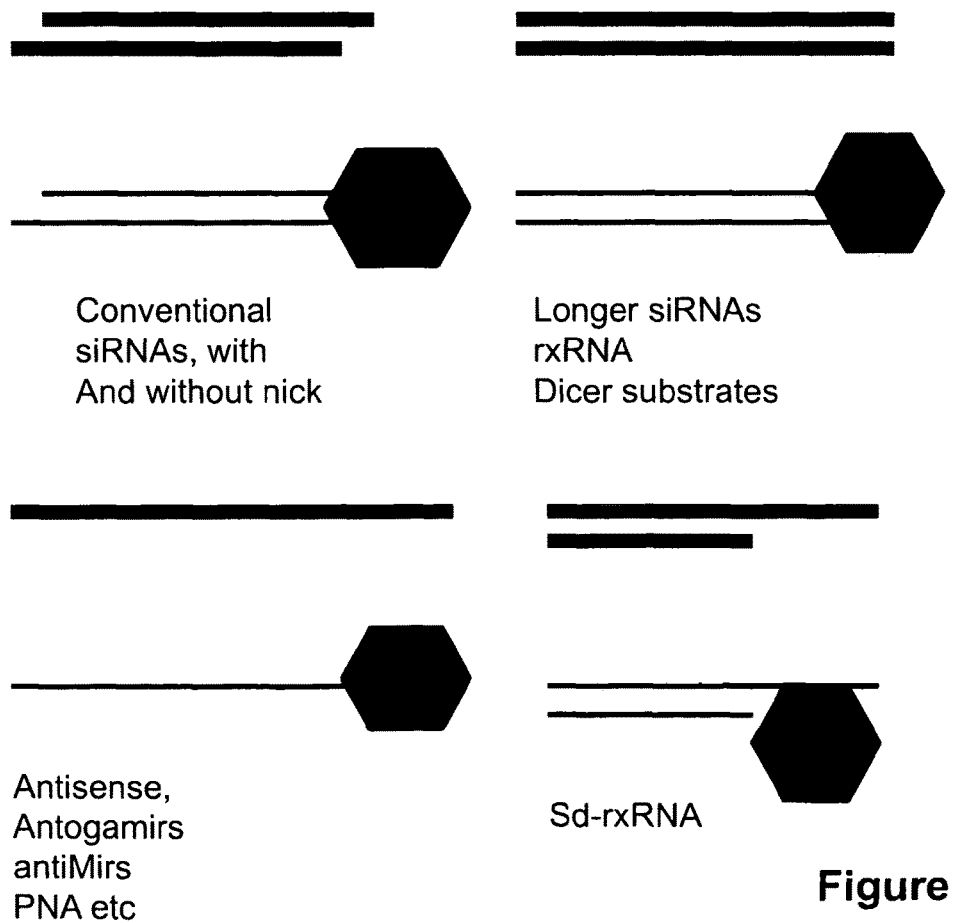

Figure 14

A
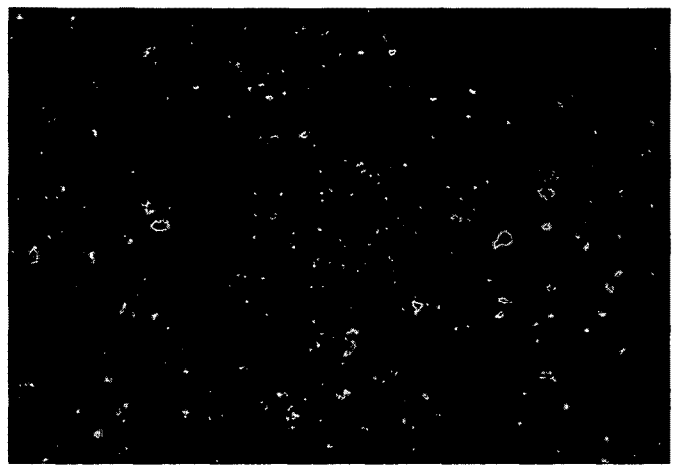
1:10 RNA:Lipid,
50:0:50 DOPC:DOPE:Chol
B
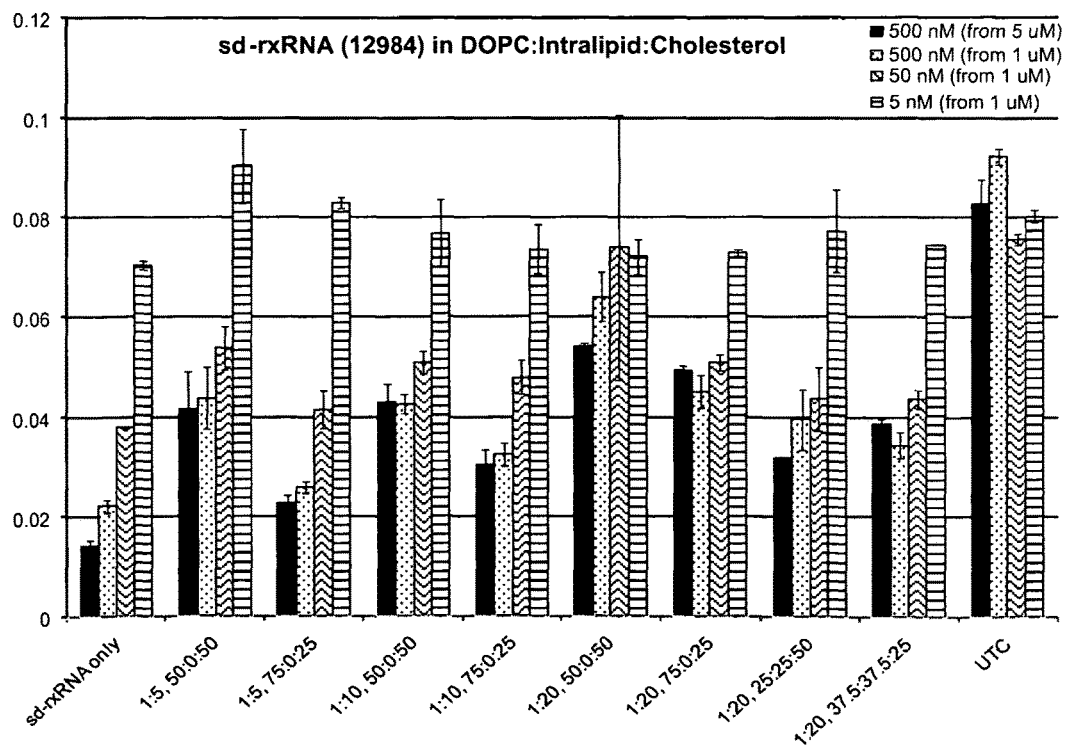
Figure 24

Figure 26

| RNA:Lipid | DOPC:Chol | Peak 1 Size (nm) | | Peak 2 Size (nm) | | Zeta Potential (mV) | |
|---|---|---|---|---|---|---|---|
| 1:5 | 50:50 | 401 | ±36 | 95 | ±7 | -15 | ±5 |
| 1:10 | 25:75 | 242 | ±14 | 64 | ±3 | -25 | ±2 |
| 1:10 | 50:50 | 66 | ±10 | - | - | -12 | ±3 |
| 1:10 | 75:25 | 71 | ±10 | - | - | -9 | ±3 |
| 1:20 | 50:50 | 121 | ±5 | - | - | -8 | ±1 |

Figure 28

| Material | Supplier | Natural or Synthetic | Category | Ordered | Amount |
|---|---|---|---|---|---|
| Intralipid, 20% | Sigma | | | 6/15/2009 | 100 mL |
| DOPC (1,2-Dioleoyl-sn-Glycero-3-phosphocholine) | Avanti | Synthetic | Phospholipid | 6/18/2009 | 1 g |
| DOPE (1,2-Dioleoyl-sn-Glycero-3-phosphoethanolamine) | Avanti | Synthetic | Phospholipid | 6/18/2009 | 1 g |
| Cholesterol | Avanti | Natural | Sterol | 6/18/2009 | 1 g |
| Egg PC (L-alpha-phosphatidylcholine) | Avanti | Natural | Phospholipid | 6/29/2009 | 25 mg |
| Egg PE (L-alpha-phosphatidylethanolamine) | Avanti | Natural | Phospholipid | 6/29/2009 | 25 mg |
| Egg PA (L-alpha-phosphatidic acid (sodium salt)) | Avanti | Natural | Phospholipid | 6/29/2009 | 25 mg |
| DLPC (1,2-dilinoleoyl-sn-glycero-3-phosphocholine) | Avanti | Synthetic | Phospholipid | 6/29/2009 | 25 mg |
| DSPC (1,2-distearoyl-sn-glycero-3-phosphocholine) | Avanti | Synthetic | Phospholipid | 6/29/2009 | 25 mg |
| DOPA (1,2-dioleoyl-sn-glycero-3-phosphate (sodium salt)) | Avanti | Synthetic | Phospholipid | 6/29/2009 | 25 mg |
| Egg SM (Sphingomyelin) | Avanti | Natural | Shingolipid | 6/29/2009 | 25 mg |
| Egg Sphingosine | Avanti | Natural | Shingolipid | 6/29/2009 | 5 mg |
| 16:0 DG (1,2-dipalmitoyl-sn-glycerol) | Avanti | Synthetic | Neutral Lipid | 6/29/2009 | 25 mg |
| 18:1 DG (1-2-dioleoyl-sn-glycerol) | Avanti | Synthetic | Neutral Lipid | 6/29/2009 | 25 mg |
| Retinol (Vitamin A) | Sigma | Synthetic | Vitamin | 6/29/2009 | 25 mg |
| Tocopherol (Vitamin E) | Sigma | Synthetic | Vitamin | 6/29/2009 | 5 g |
| Cholecalciferol (Vitamin D) | Sigma | Synthetic | Vitamin | 6/29/2009 | 1 g |
| Cardiolipin sodium salt from bovine heart | Sigma | Natural | Phospholipid | 6/29/2009 | 10 mg |
| 1a,25-Dihydroxyvitamin D3 (Calcitriol) | Sigma | Synthetic | Vitamin | 6/29/2009 | 0.1 mg |
| 16:0 Ethylene Glycol (1,2-dipalmitoyl ethylene glycol) | Avanti | Synthetic | Neutral Lipid | 7/1/2009 | 10 mg |
| 18:1 Ethylene Glycol (1-2-dioleoyl ethylene glycol) | Avanti | Synthetic | Neutral Lipid | 7/1/2009 | 10 mg |
| Oleic Acid | Sigma | | | 7/1/2009 | 1 g |
| Stearic Acid | Sigma | | | 7/1/2009 | 1 g |
| Cholesteryl oleate | Sigma | | | 7/1/2009 | 100 mg |
| Cholesteryl stearate | Sigma | | | 7/1/2009 | 5 g |
| Glyceryl trioleate | Sigma | | | 7/1/2009 | 1 g |
| Glyceryl tristearate | Sigma | | | 7/1/2009 | 5 g |
| Soybean oil | Sigma | | | 7/1/2009 | 1 L |

Figure 37
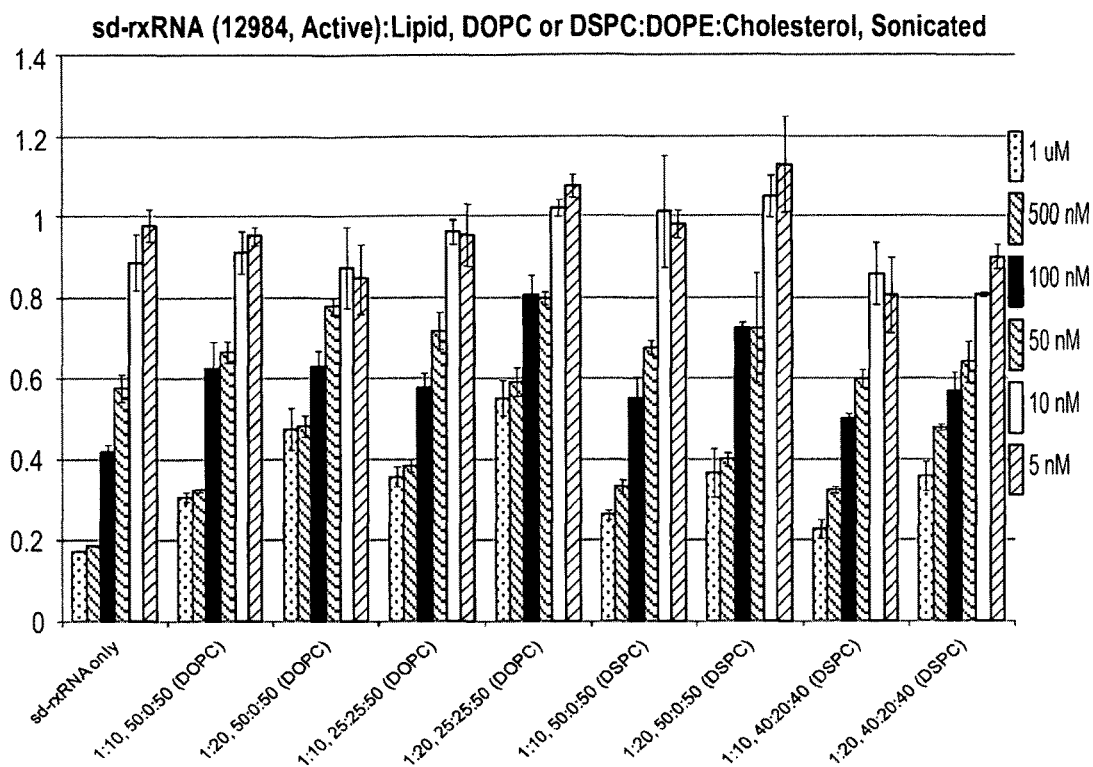
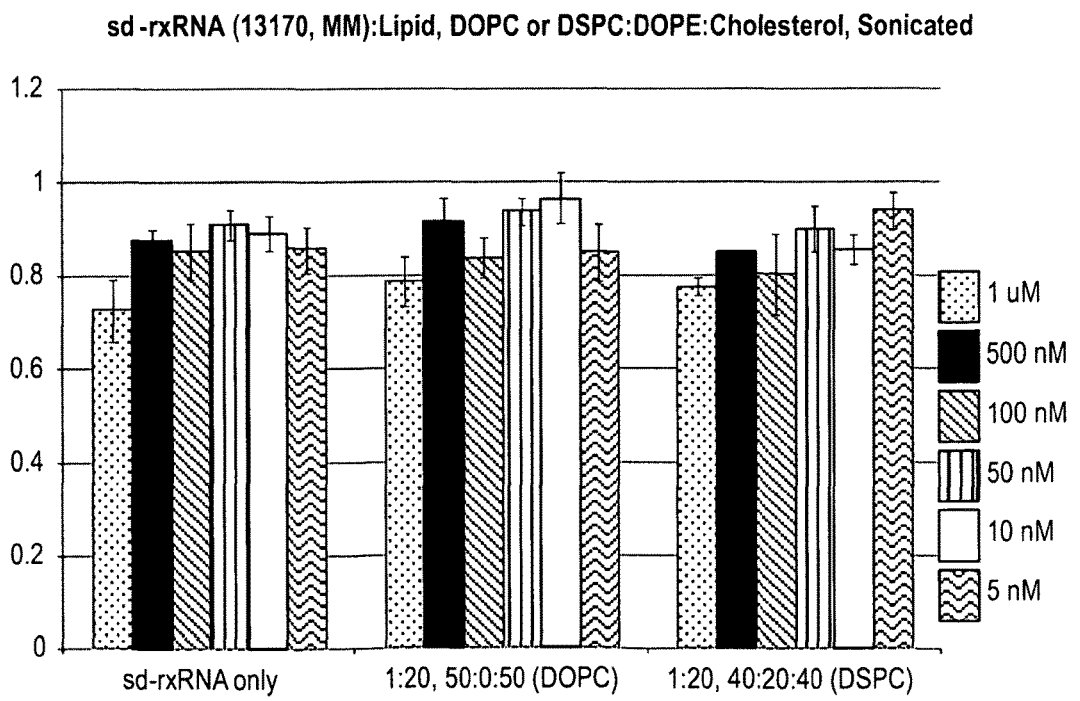

Figure 38
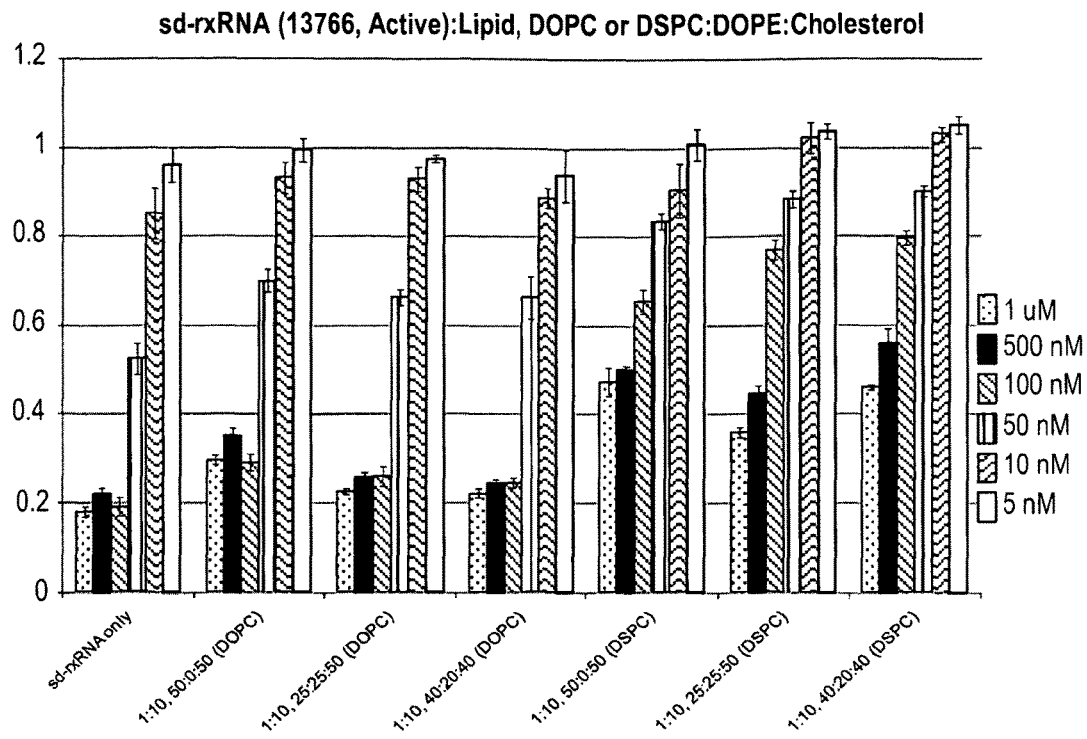
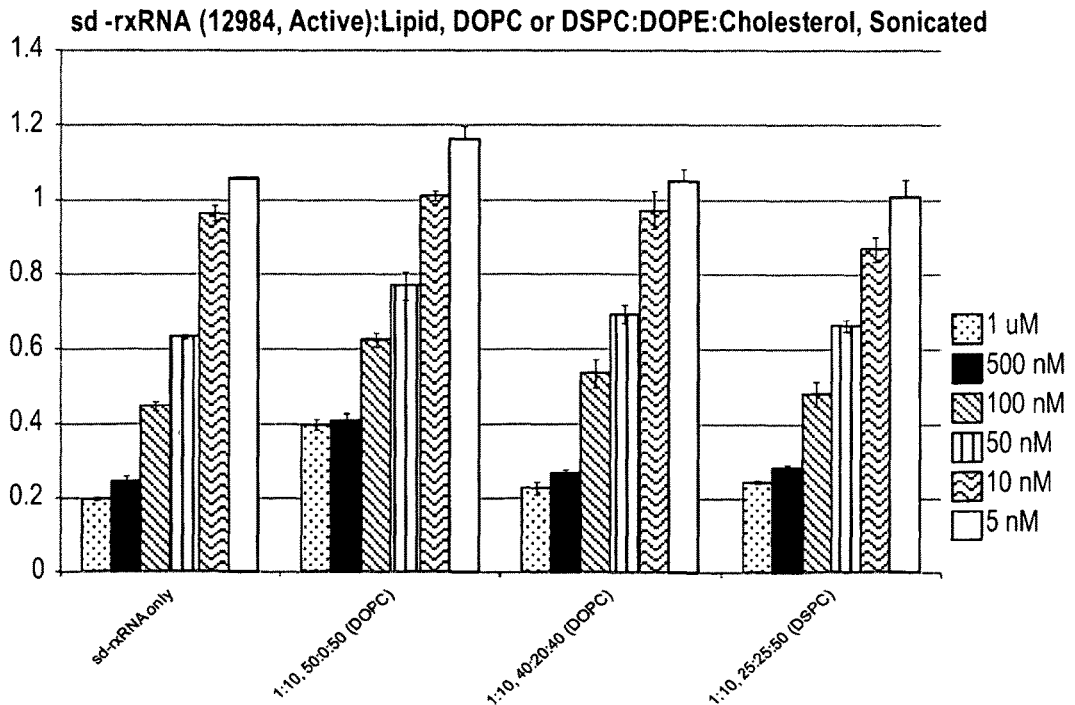

NEUTRAL NANOTRANSPORTERS

RELATED APPLICATIONS

This application is a national stage filing under 35 U.S.C § 371 of international application PCT/US2009/005251, filed Sep. 22, 2009, which was published under PCT Article 21(2) in English, and claims the benefit under 35 U.S.C. § 119(e) of U.S. provisional application Ser. No. U.S. 61/192, 954, entitled "Chemically Modified Nucleotides and Methods of Using the Same," filed on Sep. 22, 2008, U.S. 61/149,946, entitled "Minimum Length Triggers of RNA Interference," filed on Feb. 4, 2009, and U.S. 61/224,031, entitled "Minimum Length Triggers of RNA Interference," filed on Jul. 8, 2009, the disclosure of each of which is incorporated by reference herein in its entirety.

FIELD OF INVENTION

This invention pertains to non-charged lipid formulations for nucleic acid delivery.

BACKGROUND OF INVENTION

Liposome-based formulations are widely used for nucleic acid delivery. Most commercially available lipid or liposome formulations contain at least one positively charged lipid. It has been assumed that the presence of this positively charged lipid is essential for obtaining a high degree of nucleic acid loading and enhancement of liposome fusogenic properties. Several screens have been performed previously to identify optimal positively charged lipid chemistries but all the formulations that have been developed are characterized by the major issues of high levels of toxicity. In fact, in vivo limited therapeutic indexes have been reported for liposome formulations containing positively charged lipids at concentrations only slightly higher than concentrations required to achieve silencing. It would be of great benefit to develop non-toxic delivery vehicles for nucleic acids.

SUMMARY OF INVENTION

Described herein is a novel approach to nucleic acid delivery which enables efficient loading of nucleic acids into neutral fat formulations generating a new class of delivery vehicles. The nucleic acid molecule is modified to increase its hydrophobicity and is mixed with neutral fat formulation, producing efficient encapsulation of nucleic acid molecules in neutral lipid particles. Methods and compositions described herein have widespread applications for in vivo delivery of nucleic acids.

A composition is provided according to an aspect of the invention. The composition includes a hydrophobic modified polynucleotide; a neutral fatty mixture; and optionally a cargo molecule. The hydrophobic modified polynucleotide and the neutral fatty mixture form a micelle. In one embodiment the polynucleotide is RNA, such as single stranded or double stranded RNA.

In another embodiment the composition is a pharmaceutical composition and includes a pharmaceutically acceptable carrier. In yet another embodiment the composition is sterile.

The neutral fatty mixture is one or more fats which form a non-toxic mixture. In some embodiments the neutral fatty mixture includes a DOPC (dioleoylphosphatidylcholine) and/or a DSPC (distearoylphosphatidylcholine). In another embodiments the neutral fatty mixture further includes a sterol, such as, for instance, cholesterol. In yet other embodiments the neutral fatty mixture includes 20% of a fatty acid derivative of choline. The neutral fatty mixture may also include 20% sterol. In some embodiments the composition includes at least 20% DOPC and at least 20% cholesterol.

The hydrophobic portion of the hydrophobic modified polynucleotide may be covalently or non-covalently linked to the polynucleotide. In some embodiments the hydrophobic portion of the hydrophobic modified polynucleotide is a sterol, such as, for instance, a cholesterol, a cholesteryl and/or modified cholesteryl residue. In other embodiments the hydrophobic portion of the hydrophobic modified polynucleotide is one or more of bile acids, cholic acid or taurocholic acid, deoxycholate, oleyl litocholic acid, oleoyl cholenic acid, glycolipids, phospholipids, sphingolipids, isoprenoids, vitamins, saturated fatty acids, unsaturated fatty acids, fatty acid esters, triglycerides, pyrenes, porphyrines, Texaphyrine, adamantine, acridines, biotin, coumarin, fluorescein, rhodamine, Texas-Red® (sulforhodamine 101), digoxygenin, dimethoxytrityl, t-butyldimethylsilyl, t-butyldiphenylsilyl, cyanine dyes (e.g. Cy3 or Cy5), Hoechst 33258® (Phenol, 4-[5-(4-methyl-1-piperazinyl)[2,5'-bi-1H-benzimidazol]-2'-yl]-, trihydrochloride) dye, psoralen, and ibuprofen. In yet other embodiments the hydrophobic portion of the hydrophobic modified polynucleotide is a polycationic molecule, such as, for instance, protamine, arginine rich peptides, and/or spermine.

The composition optionally includes a cargo molecule such as a lipid, a peptide, vitamin, and/or a small molecule. In some embodiments the cargo molecule is a commercially available fat emulsions available for a variety of purposes selected from the group consisting of parenteral feeding. In some embodiments the commercially available fat emulsion is an intralipid or a nutralipid. In other embodiments the cargo molecule is a fatty acid mixture containing more then 74% of linoleic acid, a fatty acid mixture containing at least 6% of cardiolipin, or a fatty acid mixture containing at least 74% of linoleic acid and at least 6% of cardiolipin. In another embodiment the cargo molecule is a fusogenic lipid, such as for example, DOPE, and preferably is at least 10% fusogenic lipid In some embodiments the polynucleotide includes chemical modifications. For instance it may be at least 40% modified.

In other embodiments the polynucleotide is an isolated double stranded nucleic acid molecule having a guide strand, wherein the guide strand is 16-28 nucleotides long and has complementarity to a target gene, wherein the 3' terminal 10 nucleotides of the guide strand include at least two phosphate modifications, and wherein the guide strand has a 5' phosphate modification and includes at least one 2' O-methyl modification or 2'-fluoro modification, and a passenger strand, wherein the passenger strand is 8-28 nucleotides long and has complementarity to the guide strand, wherein the passenger strand is linked to the hydrophobic molecule, wherein the guide strand and the passenger strand form the double stranded nucleic acid molecule.

In yet another embodiment the polynucleotide is an isolated double stranded nucleic acid molecule having a guide strand and a passenger strand, wherein the guide strand is from 16-29 nucleotides long and is substantially complementary to a target gene, wherein the passenger strand is from 8-14 nucleotides long and has complementarity to the guide strand, and wherein the guide stand has at least two chemical modifications.

The polynucleotide in other embodiments is an isolated double stranded nucleic acid molecule having a guide strand and a passenger strand, wherein the guide strand is from 16-29 nucleotides long and is substantially complementary to a target gene, wherein the passenger strand is from 8-14 nucleotides long and has complementarity to the guide strand, and wherein the guide stand has a single stranded 3' region that is 5 nucleotides or longer.

In yet another embodiment the polynucleotide is an isolated double stranded nucleic acid molecule having a guide strand and a passenger strand, wherein the guide strand is from 16-25 nucleotides long and is substantially complementary to a target gene, wherein the passenger strand is from 16-25 nucleotides long and has complementarity to the guide strand, and wherein the double stranded nucleic acid molecule optionally has 3' overhangs.

The polynucleotide in other embodiments is an isolated double stranded nucleic acid molecule having a guide strand and a passenger strand, wherein the guide strand is from 24-29 nucleotides long and is substantially complementary to a target gene, wherein the passenger strand is from 24-29 nucleotides long and has complementarity to the guide strand, and wherein the double stranded nucleic acid molecule optionally has 3' overhangs.

The polynucleotide in some embodiments is an isolated single stranded nucleic acid molecule of 16-29 nucleotides in length and is substantially complementary to a target gene.

The polynucleotide may be for instance an antisense ODN, an antagomir, an antiMirs, or a PNA.

In some embodiments the ratio of neutral fatty mixture to polynucleotide is 1:5.

In other embodiments the composition is composed of about 50% cargo molecule.

The composition may have a particle size of 10-140 nm.

In preferred embodiments the composition is free of cationic lipids.

A composition of a hydrophobic modified polynucleotide; and a neutral fatty mixture is provided in other aspects of the invention. The hydrophobic modified polynucleotide and the neutral fatty mixture form a micelle and wherein between 40-100% of the nucleotides of the polynucleotide are chemically modified nucleotides.

An isolated single stranded polynucleotide having at least one phosphorothioate bond and one base modified with 4-pyril, 2-pyril is provided in other aspects of the invention. In some embodiments all ribose moieties of the polynucleotide are modified. In other embodiments at least 40% of nucleotides of the polynucleotide are chemically modified.

An isolated hydrophobic modified polynucleotide having a sterol-type molecule attached to a polynucleotide, wherein the sterol-type molecule has a polycarbon chain length of 3-7 or 9-18 carbons is provided in other aspects of the invention. In some embodiments the sterol-type molecule has a polycarbon chain length of 7.

In another aspect the invention is a method for delivering an polynucleotide to a cell, by contacting a cell with a composition or a polynucleotide of the invention to deliver the polynucleotide to the cell. The method may be performed in vitro or in vivo.

A method of inducing RNAi in a cell is provided according to other aspects of the invention. The method involves contacting a cell with a composition or a polynucleotide of the invention, wherein the polynucleotide has at least a region of sequence correspondence to a target gene and wherein the polynucleotide induces RNAi of mRNA of the target gene.

A method of inducing RNAi in a subject by administering to a subject an effective amount for inducing RNAi of mRNA of a target gene, a composition or a polynucleotide of the invention is provided in other aspects. The polynucleotide has at least a region of sequence correspondence to the target gene. In some embodiments the subject is a human. In other embodiments the target gene is PPIB, MAP4K4, and/or SOD1.

A method is also provided, in which alteration of lipid content and ratio of the composition of the invention is used to alter pharmacokinetic behavior and tissue distribution of polynucleotides.

In another aspect the invention is a method for delivering a polynucleotide to a target tissue of a subject, by administering to a subject a composition of the invention wherein the composition includes a fatty acid in the neutral fatty mixture or cargo molecule associated with targeting to the target tissue in order to deliver the polynucleotide to the target tissue. In one embodiment the target tissue is cardiomyocytes and the lipid is optionally cardiolipin or linoleic acid. In other embodiments the target tissue is lung, fat or liver.

A method is also provided, in which alteration of lipid content and ratio of the composition of the invention is used to optimize pharmacokinetic behavior and tissue distribution of polynucleotides to cardiomyocytes.

A method is also provided, in which alteration of lipid content and ratio of the composition of the invention is used to alter pharmacokinetic behavior and tissue distribution of polynucleotides to fat tissue.

A method is also provided, in which alteration of lipid content and ratio of the composition of the invention is used to alter pharmacokinetic behavior and tissue distribution of polynucleotides to lung tissue.

A method is also provided, in which alteration of lipid content and ratio of the composition of the invention is used to alter pharmacokinetic behavior and tissue distribution of polynucleotides to liver.

In other aspects the invention is a method of inducing RNAi in a subject by administering to a subject an effective amount for inducing RNAi of mRNA of a target gene, a composition or a polynucleotide of the invention, wherein the polynucleotide has at least a region of sequence correspondence to the target gene, wherein the step of administering is systemic, intravenous, intraperitoneal, intradermal, topical, intranasal, inhalation, oral, intramucosal or intraocular.

The invention in other aspects is an isolated hydrophobic modified polynucleotide having a polynucleotide, wherein the polynucleotide is double stranded RNA, attached to a hydrophobic molecule, wherein the hydrophobic molecule is attached to a base, a ribose or a backbone of a non-terminal nucleotide and wherein the isolated double stranded nucleic acid molecule comprises a guide strand and a passenger strand, wherein the guide strand is from 16-29 nucleotides long and is substantially complementary to a target gene, wherein the passenger strand is from 8-14 nucleotides long and has complementarity to the guide strand. In some embodiments the hydrophobic molecule is attached to the guide strand of the double stranded RNA. In other embodiments the 3' terminal 10 nucleotides of the guide strand include at least two phosphate modifications, and wherein the guide strand has a 5' phosphate modification and includes at least one 2' O-methyl modification or 2'-fluoro modification. In yet other embodiments the hydrophobic molecule is attached to the passenger strand of the double stranded RNA.

In another aspect the invention is an isolated hydrophobic modified polynucleotide having a polynucleotide non-covalently complexed to a hydrophobic molecule, wherein the hydrophobic molecule is a polycationic molecule. The polycationic molecule is protamine, arginine rich peptides, and/or spermine in some embodiments.

In yet another aspect the invention is an isolated hydrophobic modified polynucleotide having a polynucleotide, wherein the polynucleotide is double stranded RNA, directly complexed to a hydrophobic molecule without a linker, wherein the hydrophobic molecule is not cholesterol.

Thus, the present invention provides in some aspects and embodiments asymmetric dsRNA molecules. In one embodiment, dsRNA binding domain type proteins are utilized to mask the negative charges of a polynucleotide duplex as a way to facilitate cellular entry for conventional siRNAs and asymmetric dsRNAs. In another embodiment, protamine or other arginine rich peptides are used to mask the negative charges of a polynucleotide duplex as a way to facilitate cellular entry of conventional siRNAs and asymmetric dsRNAs. In another embodiment, spermine (or spermidine type moieties) are used to mask the negative charges of a polynucleotide duplex as a way to facilitate cellular entry of conventional siRNAs and asymmetric dsRNAs.

The present invention in other aspects provides asymmetric dsRNAs molecules, where one or both polynucleotides contain nucleotides where the 5'-position contains hydrophobic modifications selected from the group consisting of (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, and the like. In a particular embodiment, the asymmetric dsRNA molecule may be in combination with PS modifications. In another particular embodiment, at least 40% of the asymmetric dsRNA molecule may be chemically-modified.

The present invention also provides single stranded RISC entering and RISC inhibiting modalities, containing hydrophobic modifications. In one embodiment, the single stranded polynucleotides include a combination of phosphorothioates hydrophobicly modified nucleotides and at least 40% of moiety is chemically modified with or without a conjugate. The chemical modification may increase nucleotide hydrophobicity in order to optimize RISC single stranded substrate entry or optimize substrate based inhibition of preloaded RISC complex. While the chemistry of the compounds stays the same, the chemical modification pattern may favor either RISC entry or substrate inhibition The present invention also provides a group of sterol type molecules with an extended position 17 attached poly-hydrocarbon tail. In one embodiment, the poly-hydrocarbon tail is 8, 9, 11 or more carbons. In a particular embodiment, the poly-hydrocarbon tail is less than 8 or more than 9 carbons. The chain may be branched. The chain may also be attached through a 3' or 5' or intermolecular linker. In a particular embodiment, at least 40% of the nucleotides are modified. In another particular embodiment, the duplex region contains at least two mismatches.

The present invention also provides methods of utilizing fat emulsions to alter the pharmacokinetic and/or tissue distribution via hydrophobicly modified polynucleotides. In one embodiment, a polynucleotide with increased hydrophobicity is provided in combination with an intralipid type formulation. In a particular embodiment, increased hydrophobicity is achieved by attaching a sterol type modalities, one or more lipids, and/or making one or more chemical modifications. In a particular embodiment, the intralipid type formulation contains more then 74% linoleic acid. In another particular embodiment, a sterol type molecule with a position 17 chain longer than 9 carbons in attached in combination with the use of one or more intralipid type formulations.

The present invention also provides a method of altering the intralipid composition in order to alter the tissue distribution of the polynucleotides of the present invention. In one embodiment, a polynucleotide with a sterol type molecule with a position 17 chain longer than 9 carbons in combination with intralipid formulation containing more then 7% of cardiolipin is provided. In a particular embodiment, the intralipid formulation contains more than 74% of linoleic acid. In another particular embodiment, polynucleotides are provided with sterol type molecules with a position 17 chain longer than 9 carbons, with at least 40% of nucleotides being chemically modified in combination with intralipid formulation containing more then 74% of linoleic acid and 7% of cardiolipin.

Use of any of the compositions of the invention for inhibiting expression of a target gene or an miRNA is also provided as an aspect of the invention.

A method for manufacturing a medicament of any of the compositions of the invention for inhibiting expression of a target gene in order to treat a disease is also provided.

A composition of an isolated polynucleotide of the invention for inhibiting expression of a target gene or an miRNA is also provided as an aspect of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

FIG. 1A depicts adsRNA with extended guide or passenger strands; FIG. 1B depicts adsRNA with length variations of a cell penetrating polynucleotide; FIG. 1C depicts adsRNA with 3' and 5' conjugates; FIG. 1D depicts adsRNAs with mismatches.

FIG. 7A depicts an adsRNA molecule; FIG. 7B depicts an siRNA molecule of approximately 17-30 by long; FIG. 7C depicts a RISC entering strand; FIG. 7D depicts a substrate analog strand. Chemical modification patterns, as depicted in FIG. 7, can be optimized to promote desired function.

FIG. 11A depicts a polynucleotide with a hydrophobic conjugate; FIG. 11B depicts linoleic acid; FIG. 11C depicts a micelle formed from a mixture of polynucleotides containing hydrophobic conjugates combined with fatty acids.

FIG. 13 presents a graph and schematics of RNAi compounds showing the chemical/structural composition of highly effective sd-rxRNA compounds. Highly effective compounds were found to have the following characteristics: antisense strands of 17-21 nucleotides, sense strands of 10-15 nucleotides, single-stranded regions that contained 2-12 phosphorothioate modifications, preferentially 6-8 phosphorothioate modifications, and sense strands in which the majority of nucleotides were 2'OMe modified, with or without phosphorothioate modification. Any linker chemistry can be used to attach these molecules to hydrophobic moieties such as cholesterol at the 3' end of the sense strand. Version GIIa-b of these RNA compounds demonstrate that elimination of 2'F content has no impact on efficacy.

FIG. 14 presents a schematic demonstrating nucleic acids that can be formulated using methods described herein. Nucleic acids compatible with methods associated with the invention can include, for example, traditional siRNA, longer siRNAs (24-29), single stranded oligos, antisense, antogamirs and sd-rxRNA. The nucleic acid molecule is modified such that its hydrophobicity is substantially increased. This can be achieved by modifying bases, sugars or nucleic acid backbone or/and by linking a hydrophobic molecule to the nucleic acid. The hydrophobic molecule can be attached anywhere in the compound and can include, for example, a fatty acid, sterol, vitamin, small molecule or peptide. The hydrophobic molecule can be covalently or non covalently attached.

FIG. 21 also demonstrates that complexes are formed at different oligonucleotide concentrations, with higher concentrations favoring more efficient complex formation.

FIG. 24 presents a fluorescent image and a graph. FIG. 24A demonstrates that neutral lipid based formulations enter cells (HeLa) and effectively silence genes. FIG. 24B demonstrates that the oligonucleotide/lipid ratio and formulation composition affects the level of silencing. Significantly, no toxicity was observed even at 1 uM concentration. This lack of toxicity is a significant improvement over positively charge traditional formulations (i.e., lipofectamine) which exhibit a drastic toxicity at a much lower dose range. This data demonstrates that neutral fat/oligonucleotide formulations are non toxic or have highly reduced toxicity relative to previously described positively charged formulations, and have a wider therapeutic index.

FIG. 26 presents a table describing the peak sizes and zeta potential of RNA:Lipid and DOPC:Chol complexes.

FIG. 28 shows a panel of lipids used for formulation preparations.

FIG. 37 is a bar graph of data demonstrating efficient cellular uptake and lack of toxicity for variety of neutral fat formulations FIG. 38 is a bar graph of data demonstrating that different type of hydrophobic oligonucleotides work better with different type of neutral formulations. For example 13766 was more efficacious in a presence of DOPC based formulations comparer to DSPC based formulation, while 12884 has better efficacy in DSPC based formulations as compare to DOPC based formulations. The 12884 has additional hydrophobic molecule attached to the 5' end of the passenger strand in addition to conventional sd-rxRNA structures described previously.

DETAILED DESCRIPTION

Figure 1:
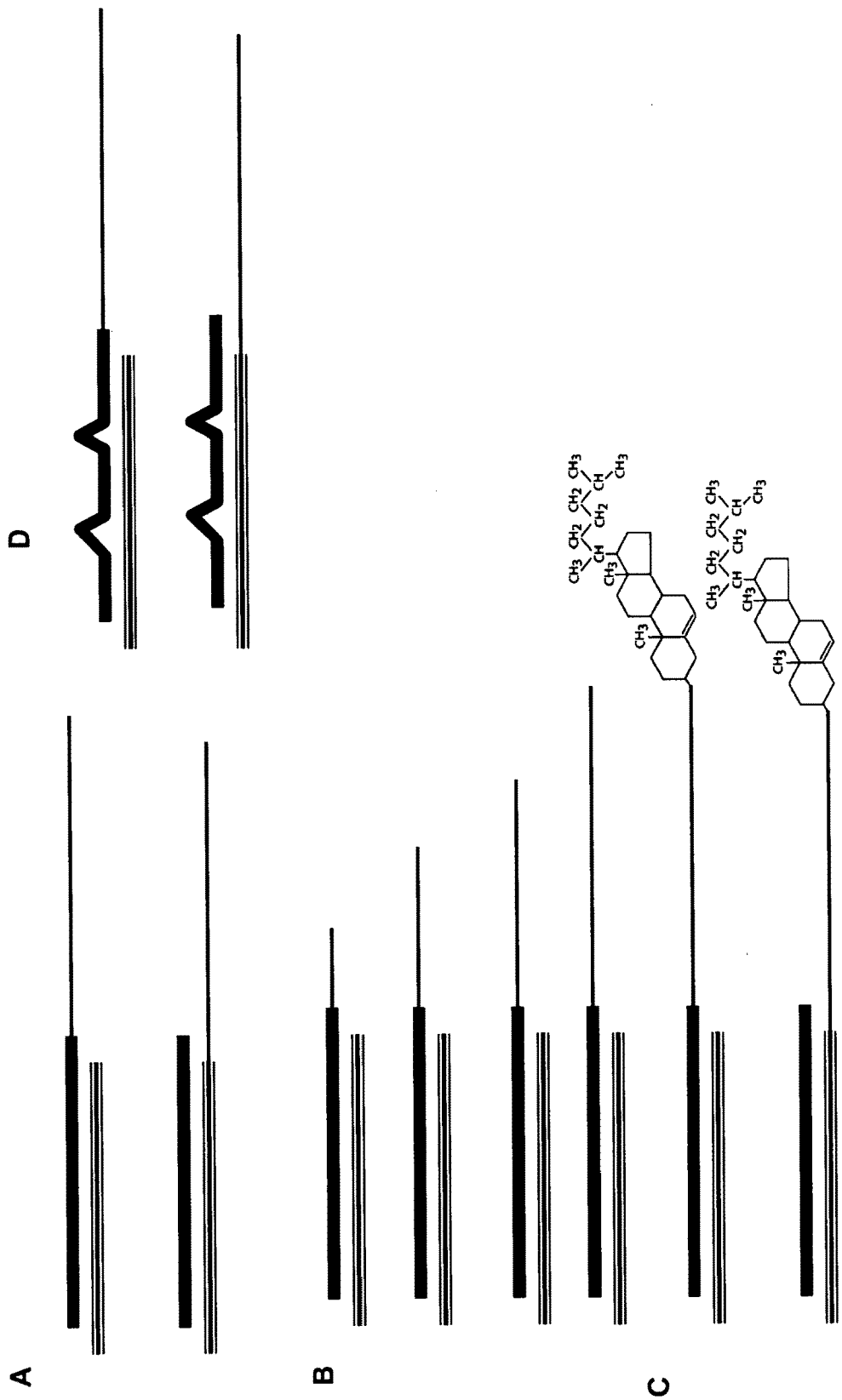
FIG. 1 is a schematic depicting proposed structures of asymmetric double stranded RNA molecules (adsRNA). Bold lines represent sequences carrying modification patterns compatible with RISC loading. Striped lines represent polynucleotides carrying modifications compatible with passenger strands. Plain lines represent a single stranded polynucleotide with modification patterns optimized for cell interaction and uptake.

Neutral fat-based formulations for the efficient delivery of oligonucleotides is disclosed herein. Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

The compositions provided herein are referred to as neutral nanotransporters because they enable quantitative oligonucleotide incorporation into non-charged lipids mixtures. The lack of toxic levels of cationic lipids in the neutral nanotransporter compositions of the invention is an important feature.

The neutral nanotransporters compositions of the invention enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid, peptide, vitamin, polymer or small molecule can also be included in the composition. This composition, where part of the formulation is build into the oligonucleotide itself enables efficient encapsulation of oligonucleotide in neutral lipid particles. Any oligonucleotides may be used in the compositions of the invention, For example, the oligonucleotides may be RNA, DNA, single stranded, double stranded etc. As shown in the examples several sd-rxRNA compounds as well as non-sd-rxRNA compounds have been synthesized and formulated according to the invention.

One of several unexpected observations associated with the invention was that oligonucleotides could effectively be incorporated in a lipid mixture that was free of cationic lipids and that such a composition could effectively deliver the therapeutic oligonucleotide to a cell in a manner that it is functional. Another unexpected observation was the high level of activity observed when the fatty mixture is composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation. The prior art demonstrated only a 1-5% oligonucleotide encapsulation with non-charged formulations, which is not sufficient to get to a desired amount of in vivo efficacy. Compared to the prior art using neutral lipids the level of oligonucleotide delivery to a cell was quite unexpected.

As shown in the Examples below stable particles ranging in size from 50 to 140 nm were formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

Compositions

The compositions of the invention include a hydrophobic modified polynucleotide, a neutral fatty mixture, and optionally a cargo molecule. A "hydrophobic modified polynucleotide" as used herein is a polynucleotide (described below) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoylc- holenic, palmityl, heptadecyl, myrisityl, bile acids, cholic acid or taurocholic acid, deoxycholate, oleyl litocholic acid, oleoyl cholenic acid, glycolipids, phospholipids, sphingo- lipids, isoprenoids, such as steroids, vitamins, such as vitamin E, fatty acids either saturated or unsaturated, fatty acid esters, such as triglycerides, pyrenes, porphyrines, Texaphyrine, adamantine, acridines, biotin, coumarin, fluorescein, rhodamine, Texas-Red® (sulforhodamine 101), digoxygenin, dimethoxytrityl, t-butyldimethylsilyl, t-butyldiphenylsilyl, cyanine dyes (e.g. Cy3 or Cy5), Hoechst 33258™ (Phenol, 4-[5-(4-methyl-1-piperazinyl)[2,5'-bi-1H-benzimidazol]-yl]-, trihydrochloride) dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' or 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17

For purposes of the present invention, the term "sterol type molecules", refers or steroid alcohols, which are similar in structure to sterols. The main difference is the structure of the ring and number of carbons in a position 17 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Figure 9:
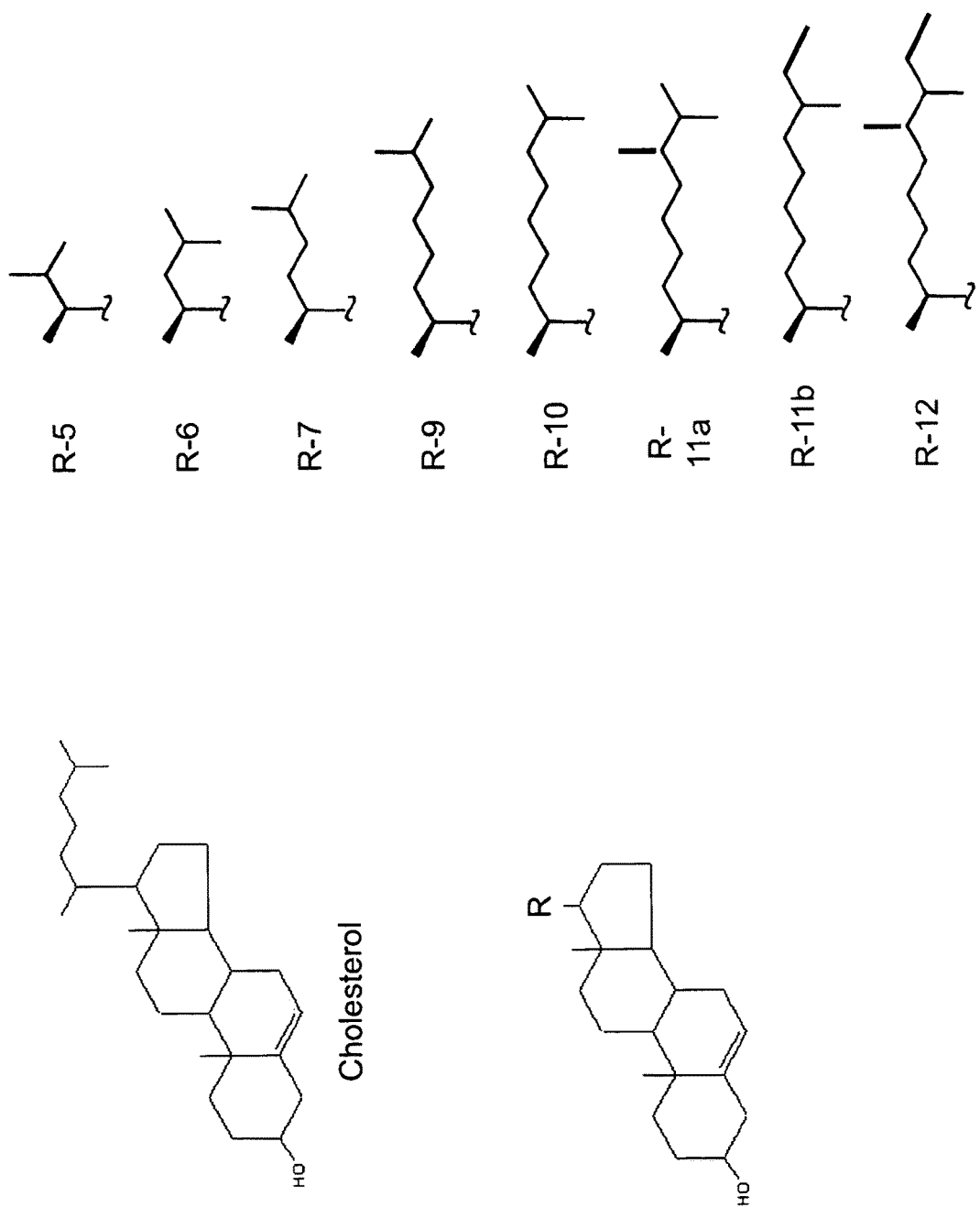
FIG. 9 is a schematic depicting examples of sterol-like structures, with variations in the size of the polycarbon chains attached at position 17.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. FIG. 9 demonstrates that there is a correlation between plasma clearance, liver uptake and the length of the polycarbon chain. Such conjugates may have significantly better in vivo efficacy, in particular delivery to liver. These types of molecules are expected to work at concentrations 5 to 9 fold lower then oligonucleotides conjugated to conventional cholesterols.

Figure 4:
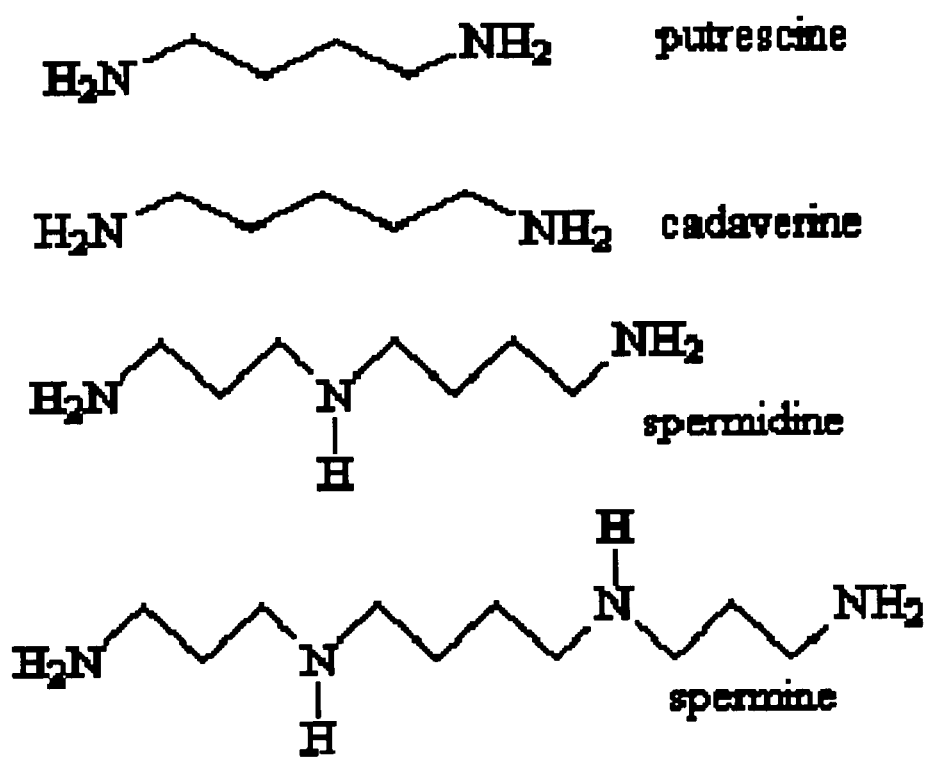
FIG. 4 is a schematic depicting positively charged chemicals that might be used for polynucleotide charge blockage.
Figure 5:
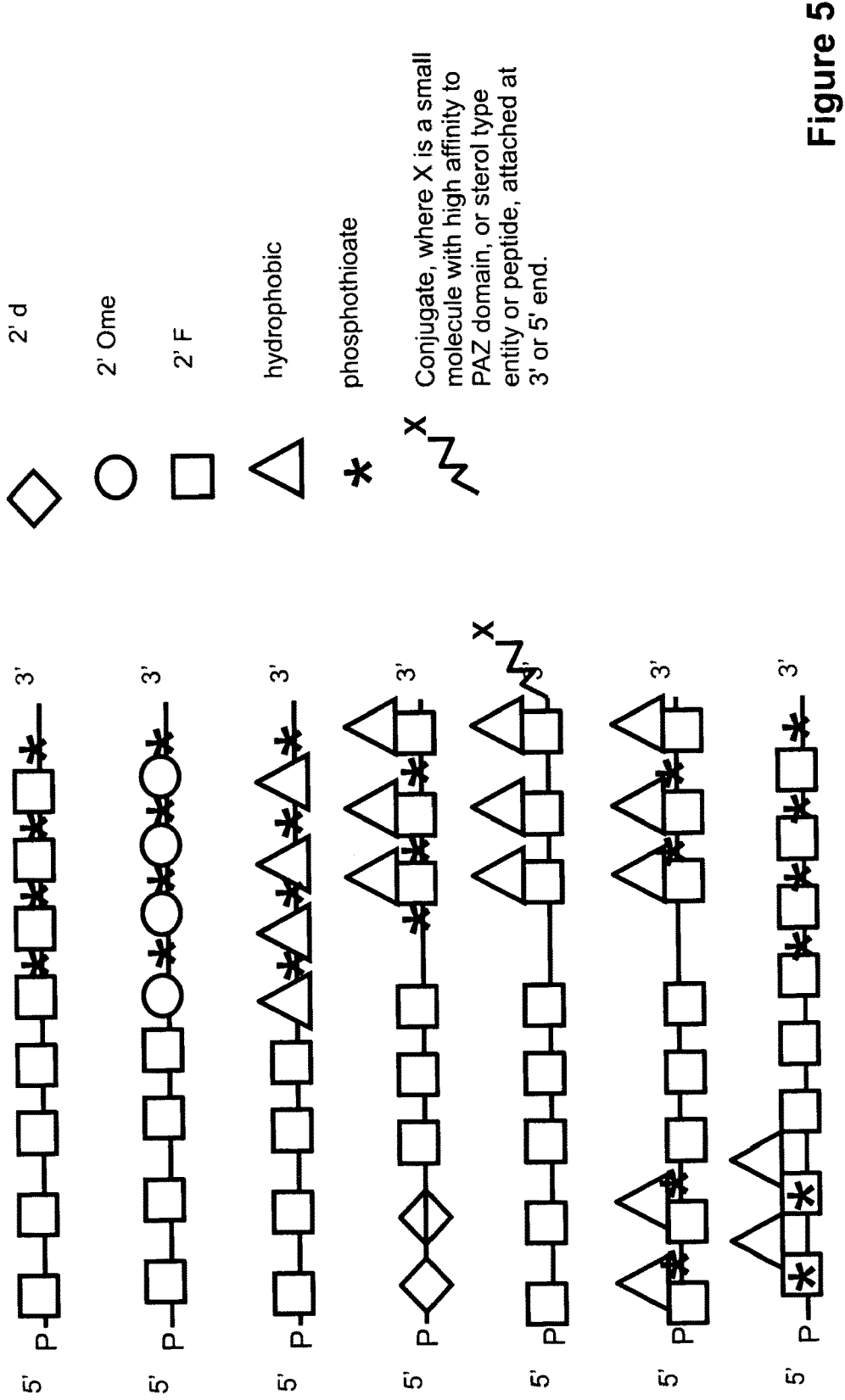
FIG. 5 is a schematic depicting examples of structural and chemical compositions of single stranded RISC entering polynucleotides. The combination of one or more modifications including 2'd, 2'Ome, 2'F, hydrophobic and phosphorothioate modifications can be used to optimize single strand entry into the RISC.

Alternatively the polynucleotide may be bound to a protein, peptide or positively charged chemical that functions as the hydrophobic molecule. Examples are shown in FIG. 4. The proteins may be selected from the group consisting of protamine, dsRNA binding domain, and arginine rich peptides. Exemplary positively charged chemicals include spermine, sperm idine, cadaverine, and putrescine (FIG. 5).

In another embodiment hydrophobic molecule conjugates may demonstrate even higher efficacy when it is combined with optimal chemical modification patterns of the polynucleotide, containing but not limited to hydrophobic modifications.

Figure 8:
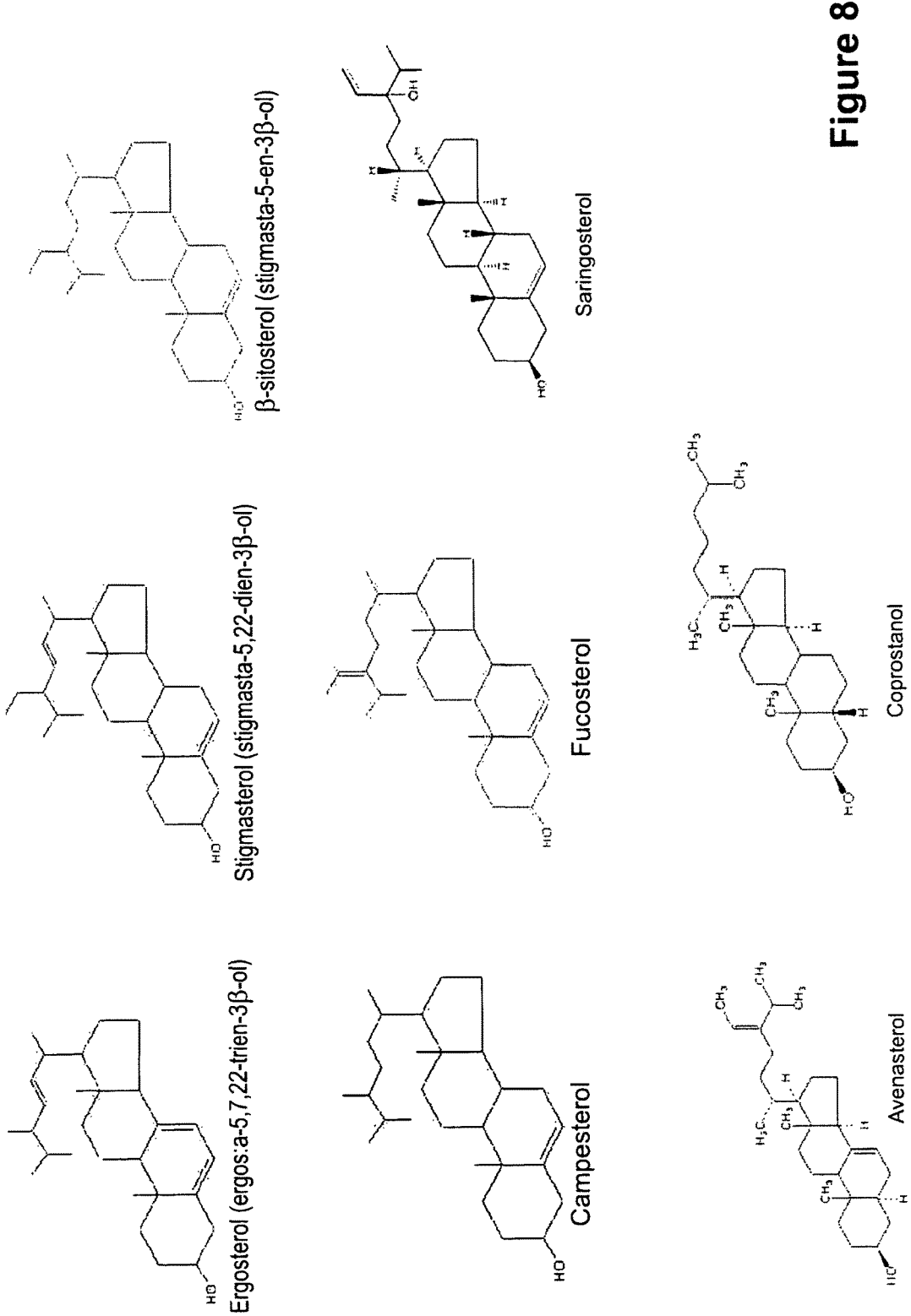
FIG. 8 is a schematic depicting examples of naturally occurring phytosterols with a polycarbon chain that is longer than 8, attached at position 17. More than 250 different types of phytosterols are known.

In another embodiment the sterol type molecule may be a naturally occurring PhytoSterols such as those shown in FIG. 8. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Figure 21:
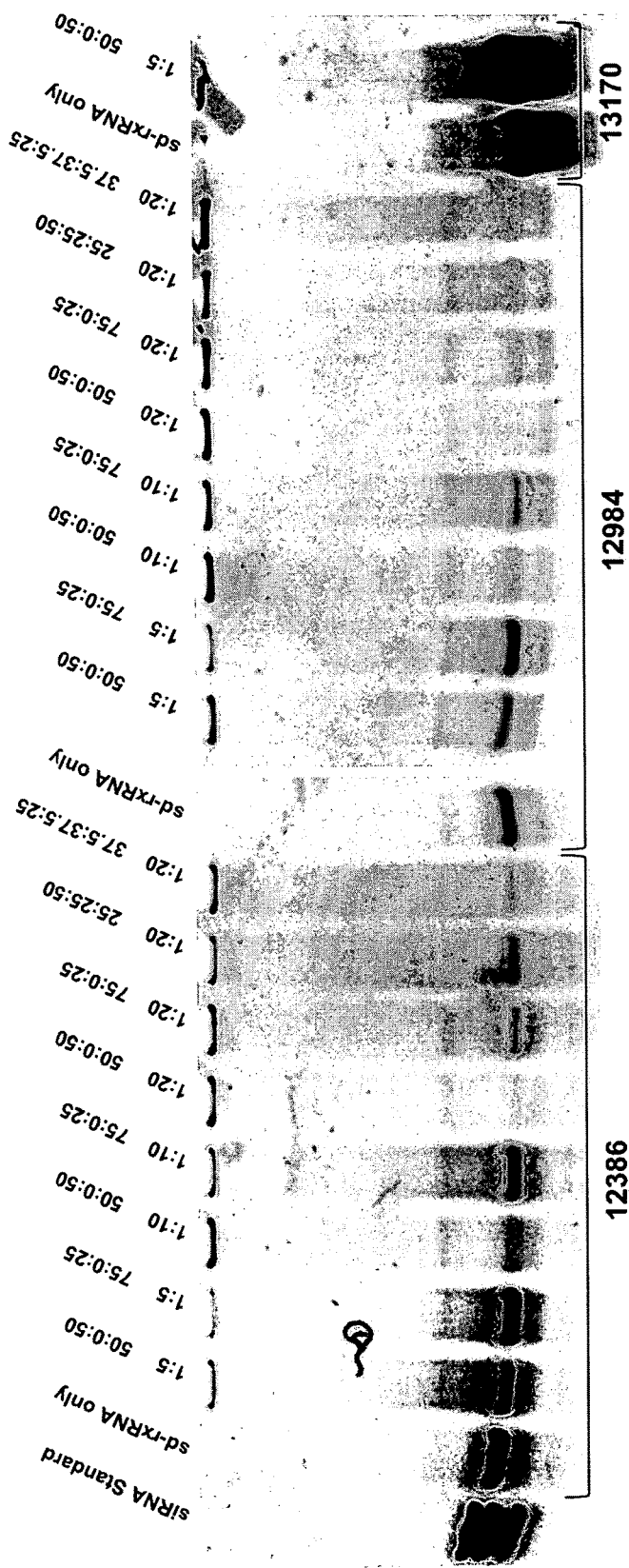
FIG. 21 presents gels demonstrating that various additional compounds (lipids, peptides, small molecules) might be encapsulated into the particle as long as formulation comprises at least 20% of DOPC/Cholesterol-type compounds. The demonstrated cargo lipid is intralipid. Variation in the identity, amounts and ratios of cargo lipids will affect cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds.
Figure 22:
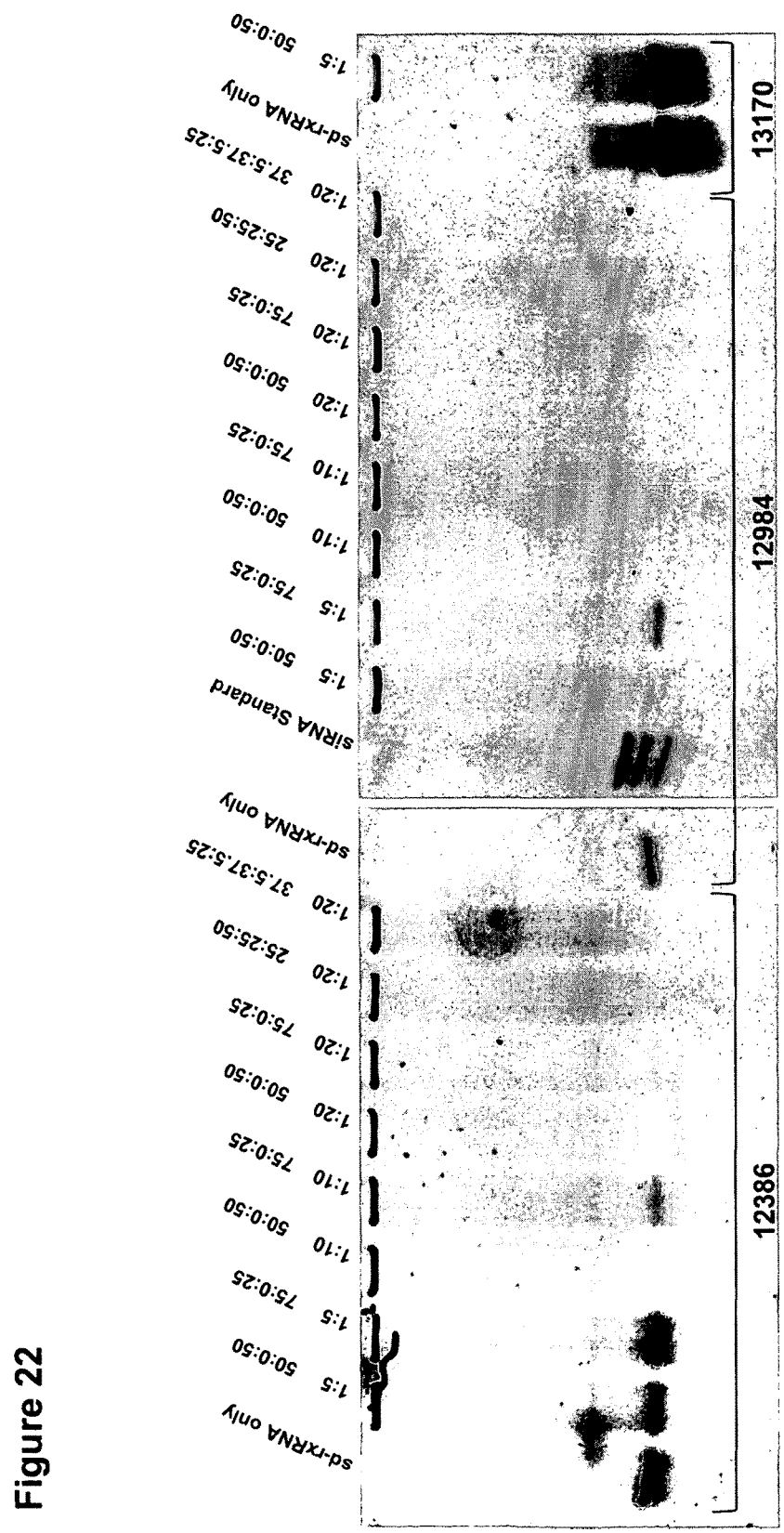
FIG. 22 presents gels demonstrating that more efficient complex formation is observed at higher oligonucleotide concentrations.

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. Complexes are formed at different oligonucleotide concentrations, with higher concentrations favoring more efficient complex formation (FIGS. 21-22).

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

Figure 12:
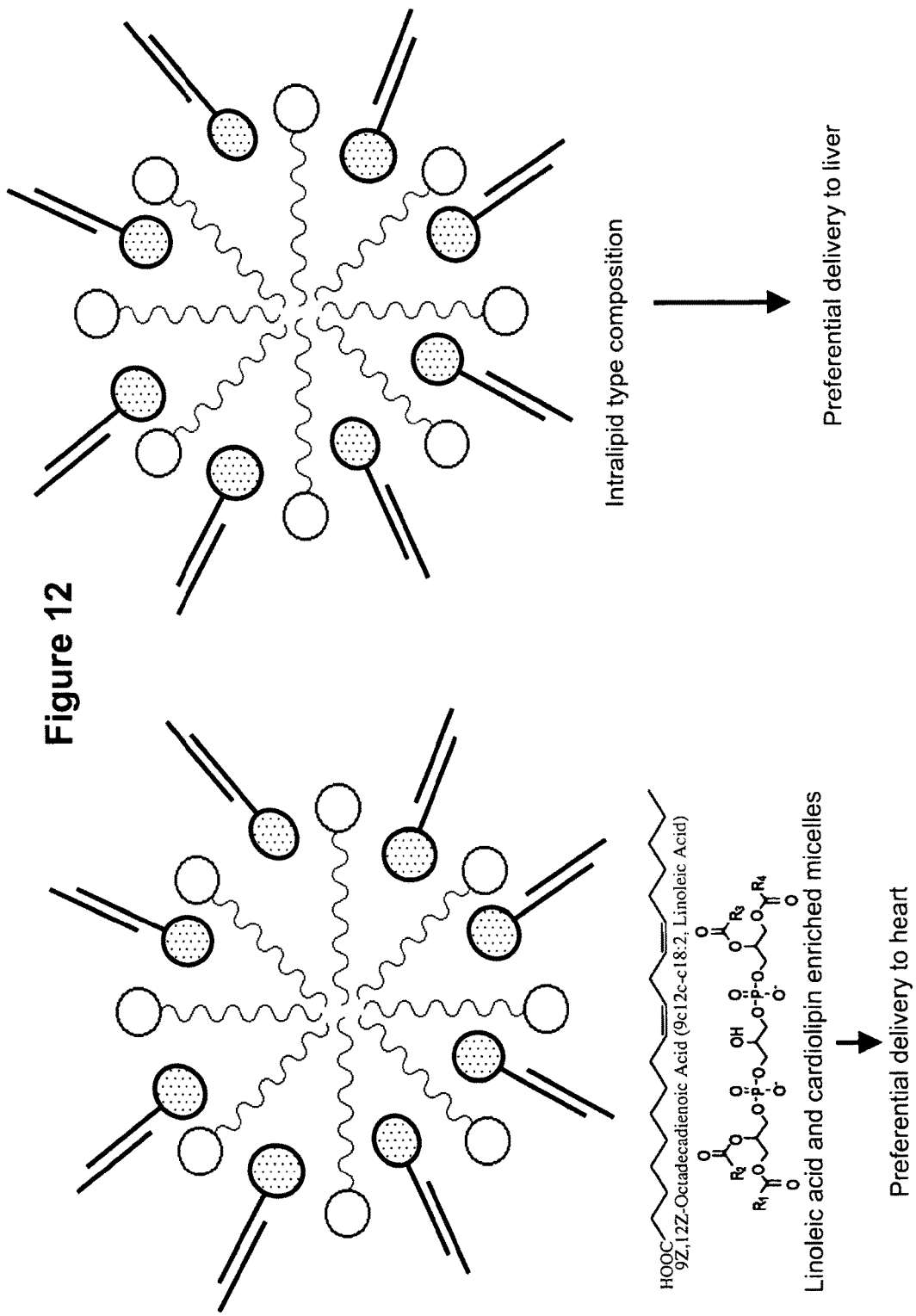
FIG. 12 is a schematic depicting how alteration in lipid composition can affect pharmacokinetic behavior and tissue distribution of hydrophobically modified and/or hydrophobically conjugated polynucleotides. In particular, use of lipid mixtures enriched in linoleic acid and cardiolipin results in preferential uptake by cardiomyocites.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues (FIG. 12).

In another embodiment the fat emulsions of the cargo molecule contain more then 70% of Linoleic acid (C18H32O2) and/or cardiolipin are used for specifically delivering RNAi to heart muscle.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

For purposes of the present invention, the term, "polynucleotide" includes any molecule that is an organic polymer molecule composed of nucleotide monomers covalently bonded in a chain. DNA (deoxyribonucleic acid) and RNA (ribonucleic acid) are examples of polynucleotides. For purposes of the present invention, the term "polynucleotide" is used synonymously with oligonucleotide and nucleic acid. "Nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Polynucleotides include any such primers, probes, and/or oligomer fragments. Polynucleotides, include polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. The term polynucleotide includes any type of nucleic acid and/or oligonucleotide. These terms refer only to the primary structure of the molecule. Thus, these terms include double- and single-stranded DNA, as well as triple-, double- and single-stranded RNA. Exemplary RNA molecules include RNAi, siRNA, miRNA and siRNA inhibitors, single stranded substrates for RISC assembly and the like. Some of these examples will be discussed in more detail below. Such discussion is exemplary only and is non-limiting.

For purposes of the present invention, the term "deoxynucleotide" refers to a nucleotide or polynucleotide lacking an OH group at the 2' or 3' position of a sugar moiety with appropriate bonding and/or 2',3' terminal dideoxy, instead having a hydrogen bonded to the 2' and/or 3' carbon.

For purposes of the present invention, the terms "deoxyribonucleotide" and "DNA" refer to a nucleotide or polynucleotide comprising at least one ribosyl moiety that has an H at its 2' position of a ribosyl moiety instead of an OH.

For purposes of the present invention, the term "gene" is defined to include both transcribed and non-transcribed elements. Thus, for instance, a gene can include any non-transcribed enhancer and/or promoter (i.e. genomic DNA) that plays a role in determining the level, timing, or tissue specificity of expression of a particular mRNA transcript or non-coding RNA. In addition, the 5' UTR, ORF, 3' UTR, introns, as well as non-coding RNAs such as miRNAs, piRNAs, tRNAs, rRNAs, and more, are included as elements of a gene.

The hydrophobic modified nucleotide may be an siRNA which includes conventional siRNAs, sd-rxRNAs, asymmetric dsRNAs, single stranded RISC entering polynucleotides, and single stranded RISC inhibiting polynucleotides.

Aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

For purposes of the present invention, the phrase "guide strand" as used herein, refers to a polynucleotide or region of a polynucleotide that is substantially (i.e., 80% or more) or 90% complementary to a target nucleic acid of interest and is capable of efficient loading into the RISC complex. A guide strand may be single stranded or part of a duplex and may be comprised of a polynucleotide region that is RNA, DNA or chimeric RNA/DNA. For example, an antisense strand may be complementary, in whole or in part, to a molecule of messenger RNA, an RNA sequence that is not mRNA or sequence of DNA that is either coding or non-coding. The guide strand can be modified with a diverse group of small molecules and/or conjugates and one of the embodiments is related to use of chemical modifications, which improve activity of single stranded guide strands.

For purposes of the present invention, the phrase "passenger strand" or "sense strand" refers to a polynucleotide or region that has the same nucleotide sequence, in whole or in part, as a target nucleic acid such as a messenger RNA or a sequence of DNA. When a sequence is provided, by convention, unless otherwise indicated, it is the sense strand (or region), and the presence of the complementary antisense strand (or region) is implicit. In is also implied that the passenger strand is a second non-essential part of the duplex responsible for promotion of RISC entry and the one, which will be lost after initial RISC loading.

For example, double-stranded RNA (dsRNA), for instance, may be formulated according to the methods of the invention. In one embodiment, the invention provides a dsRNA molecule such as a conventional siRNA. Conventional ds siRNA can include a duplex structure of between 18 and 25 basepairs (e.g., 21 base pairs). In some embodiments, the dsRNAs include at least one strand that is at least 21 nt long. In other embodiments, the dsRNAs include at least one strand that is at least 15, 16, 17, 18, 19, 20, or more contiguous nucleotides. In conventional siRNA, at least one end of the dsRNA has a single-stranded nucleotide overhang of 1 to 4, generally 1 or 2 nucleotides. Generally, the single-stranded overhang is located at the 3'-terminal end of the antisense strand or, alternatively, at the 3'-terminal end of the sense strand. The dsRNA may also have a blunt end, generally located at the 5'-end of the antisense strand.

The dsRNA may be cross-linked in some embodiments. Chemical linking of the two separate dsRNA strands may be achieved by any of a variety of well-known techniques, for example by introducing covalent, ionic or hydrogen bonds; hydrophobic interactions, van der Waals or stacking interactions; by means of metal-ion coordination, or through use of purine analogues. Such chemically linked dsRNAs are suitable for packaging in the association complexes described herein. Generally, the chemical groups that can be used to modify the dsRNA include, without limitation, methylene blue; bifunctional groups, generally bis-(2-chloroethyl)amine; N-acetyl-N'-(p-glyoxylbenzoyl)cystamine; 4-thiouracil; and psoralen. In one embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, Biochem. (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is generally formed by triple-helix bonds.

dsRNA formulated according to the invention also includes sd-rxRNA. sd-rxRNA refers to a class of RNA molecules described in a PCT application filed on even date entitled "Minimum length triggers of RNA Interference" as well as the provisional applications to which the instant application claims priority, each of which is incorporated by reference. Briefly, sd-rxRNA are asymmetric nucleic acid molecules with a double stranded region of a minimal length such as 8-14 nucleotides, are effective in silencing gene expression. Molecules with such a short double stranded region have not previously been demonstrated to be effective in mediating RNA interference. It had previously been assumed that that there must be a double stranded region of 19 nucleotides or greater. The molecules described herein are optimized through chemical modification, and in some instances through attachment of hydrophobic conjugates. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

For purposes of the present invention, the phrase "silencing" is defined as an RNAi-mediated or antisense mediated reduction in gene expression that can be measured by any number of methods including PCR-based methods, Northern blot analysis, Branched DNA, western blot analysis, and other art recognized techniques.

For purposes of the present invention, the term "siRNA" and the phrase "short interfering RNA" refer to unimolecular nucleic acids and to nucleic acids comprised of two separate strands that are capable of performing RNAi and that have a duplex region that is from about 18 to about 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

For purposes of the present invention, the phrase "RNA interference" and the term "RNAi" are synonymous and refer to the process by which a single, double, or tripartite molecule (e.g. an siRNA, an shRNA, an miRNA, a piRNA) exerts an effect on a biological process by interacting with one or more components of the RNAi pathway including but not limited to Drosha, RISC, Dicer, etc. The process includes, but is not limited to, gene silencing by degrading mRNA, attenuating translation, interactions with tRNA, rRNA, hnRNA, cDNA and genomic DNA, inhibition of as well as methylation of DNA with ancillary proteins. In addition, molecules that modulate RNAi (e.g. siRNA, piRNA, or miRNA inhibitors) are included in the list of molecules that enhance the RNAi pathway (Tomari, Y. et al. Genes Dev. 2005, 19(5):517-29).

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

For purposes of the present invention, the term "mismatch" includes a situation in where Watson-Crick base pairing does not take place between a nucleotide of a sense strand and a nucleotide of an antisense strand. An example of a mismatch would be an A across from a G, a C across from an A, a U across from a C, an A across from an A, a G across from a G, a C across from a C, and so on. Mismatches are also meant to include an basic residue across from a nucleotide or modified nucleotide, an acyclic residue across from a nucleotide or modified nucleotide, a gap, or an unpaired loop. In its broadest sense, a mismatch as used herein includes any alteration at a given position which decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

For purposes of the present invention, the term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G, G to U), or in any other manner that allows for the formation of stable duplexes. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. Perfect complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other.

Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

In contrast to single-stranded polynucleotides, duplex polynucleotides have been difficult to deliver to a cell as they have rigid structures and a large number of negative charges which makes membrane transfer difficult. Unexpectedly, it was found that the polynucleotides of the present invention, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

Single stranded modified and non modified RNA, DNA molecules may also be formulated according to the methods of the invention. An example of a single stranded polynucleotide that may be formulated according to the invention is those ODN described in PCT/US2009/004326. Briefly, these ssRNA can form double stranded structures based on internal interactions or on interactions with identical sequences. For instance they may include two identical single-stranded polynucleotides, each of the single-stranded polynucleotide comprising a 5'-stem sequence having a 5'-end, a 3'-stem sequence having a 3'-end, and a linker sequence linking the 5'-stem sequence and the 3'-stem sequence, wherein: (1) the 5'-stem sequence of a first single-stranded polynucleotide hybridize with the 3'-stem sequence of a second single-stranded polynucleotide to form a first double-stranded stem region; (2) the 5'-stem sequence of the second single-stranded polynucleotide hybridize with the 3'-stem sequence of the first single-stranded polynucleotide to form a second double-stranded stem region; and, (3) the linker sequences of the first and the second single-stranded polynucleotides form a loop or bulge connecting the first and the second double-stranded stem regions, wherein the 5'-stem sequence and at least a portion of the linker sequence form a guide sequence complementary to a transcript (such as an mRNA or a non-coding RNA) of a target gene.

Single stranded RNA molecules also include for instance microRNAs (miRNAs). MicroRNAs are small noncoding RNA molecules that are capable of causing post-transcriptional silencing of specific genes in cells such as by the inhibition of translation or through degradation of the targeted mRNA. A miRNA can be completely complementary or can have a region of noncomplementarity with a target nucleic acid, consequently resulting in a "bulge" at the region of non-complementarity. The region of noncomplementarity (the bulge) can be flanked by regions of sufficient complementarity, preferably complete complementarity to allow duplex formation. Preferably, the regions of complementarity are at least 8 to 10 nucleotides long (e.g., 8, 9, or 10 nucleotides long). A miRNA can inhibit gene expression by repressing translation, such as when the microRNA is not completely complementary to the target nucleic acid, or by causing target RNA degradation, which is believed to occur only when the miRNA binds its target with perfect complementarity. The invention also can include double-stranded precursors of miRNAs that may or may not form a bulge when bound to their targets.

A miRNA or pre-miRNA can be 16-100 nucleotides in length, and more preferably from 16-80 nucleotides in length. Mature miRNAs can have a length of 16-30 nucleotides, preferably 21-25 nucleotides, particularly 21, 22, 23, 24, or 25 nucleotides. MicroRNA precursors can have a length of 70-100 nucleotides and have a hairpin conformation. MicroRNAs can be generated in vivo from pre-miRNAs by enzymes called Dicer and Drosha that specifically process long pre-miRNA into functional miRNA.

Single Stranded DNA molecules include for instance antisense-oligonucleotides. The single-stranded oligonucleotides featured in the invention include antisense nucleic acids. An "antisense" nucleic acid includes a nucleotide sequence that is complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. Accordingly, an antisense nucleic acid can form hydrogen bonds with a sense nucleic acid target. Given a coding strand sequence (e.g., the sequence of a sense strand of a cDNA molecule), antisense nucleic acids can be designed according to the rules of Watson and Crick base pairing. The antisense nucleic acid molecule can be complementary to a portion of the coding or noncoding region of an RNA, e.g., a pre-mRNA or mRNA. For example, the antisense oligonucleotide can be complementary to the region surrounding the translation start site of a pre-mRNA or mRNA, e.g., the 5'UTR. An antisense oligonucleotide can be, for example, about 10 to 25 nucleotides in length (e.g., 11, 12, 13, 14, 15, 16, 18, 19, 20, 21, 22, 23, or 24 nucleotides in length). An antisense oligonucleotide can also be complementary to a miRNA or pre-miRNA.

An antisense nucleic acid can be constructed using chemical synthesis and/or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and target nucleic acids, e.g., phosphorothioate derivatives and acridine substituted nucleotides can be used. Other appropriate nucleic acid modifications are described herein. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense agent can include ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme, e.g., RNAse H. Degradation of the target RNA prevents translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAseH activity is desired.

Another example of a nucleic acid is a decoy-oligonucleotide, e.g., a decoy RNA. A decoy nucleic acid resembles a natural nucleic acid, but is modified in such a way as to inhibit or interrupt the activity of the natural nucleic acid. For example, a decoy RNA can mimic the natural binding domain for a ligand. The decoy RNA therefore competes with natural binding target for the binding of a specific ligand. The natural binding target can be an endogenous nucleic acid, e.g., a pre-miRNA, miRNA, premRNA, mRNA or DNA.

Aptamer are also oligonucleotides which may be formulated according to the methods of the invention. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand. An aptamer can contain any of the modifications described herein.

Antagomirs, which are single stranded, double stranded, partially double stranded and hairpin structured chemically modified oligonucleotides that target a microRNA, are also useful according to the invention. An antagomir may be for instance at least 8 or more contiguous nucleotides substantially complementary to an endogenous miRNA and more particularly agents that include 12 or more contiguous nucleotides substantially complementary to a target sequence of an miRNA or pre-miRNA nucleotide sequence. Preferably, an antagomir featured in the invention includes a nucleotide sequence sufficiently complementary to hybridize to a miRNA target sequence of about 12 to 25 nucleotides, preferably about 15 to 23 nucleotides. An antagomir that is substantially complementary to a nucleotide sequence of an miRNA can be delivered to a cell or a human to inhibit or reduce the activity of an endogenous miRNA, such as when aberrant or undesired miRNA activity, or insufficient activity of a target mRNA that hybridizes to the endogenous miRNA, is linked to a disease or disorder.

For purposes of the present invention, the term asymmetric dsRNA (adsRNA) refers to a duplex, where the length of one strand is substantially higher then the other. As a result, there is an additional single stranded region extending from a duplex. The chemical modification patterns for different regions of the asymmetric dsRNA can be different. For purposes of the present invention, the term "overhang" refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. In a conventional siRNA molecule the overhand length generally doesn't exceed 5 bases in length.

For purposes of the present invention, the term "duplex" refers to a region of double-stranded structure formed by two antiparallel polynucleotide strands as a result of base-pairing between the strands. A duplex may be formed between two separate polynucleotides, or the strands may be contained with a single polynucleotide sequence e.g. a hairpin structure where the "loop" portion of the hairpin allows the two strands to adopt an antiparallel configuration relative to each other.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

For purposes of the present invention, the term "modification pattern" refers to chemical modification pattern, which is found to be optimal for a particular application. The chemical modification pattern enables generalization of chemical principles for many different sequences. Usually, chemical modification pattern is link to easier functional position or both sequence and functional position. The 2'F modification of every C and U in the guide strand of the duplex, is considered to be an acceptable chemical modification pattern for a guide strand. Another example, is fully Omethyl modified oligo with several phosphorothioates on the ends is an acceptable chemical modification pattern for miRNA inhibitors.

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alkoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($—OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxylcarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}(CR'R'')_{0-3}H$, $(CR'R'')_{0-3}S(O)_{0-2}R'$, $(CR'R'')_{0-3O}(CR'R'')_{0-3}H$, $(CR'R'')_{0-3}COR'$, $(CR'R'')_{0-3}CO_2R'$, or $(CR'R'')_{0-3O}R'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—$(PO^{2-})$—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

Another type of conjugates that can be attached to the end (3' or 5' end), the loop region, or any other parts of the miniRNA might include a sterol, sterol type molecule, peptide, small molecule, protein, etc. In some embodiments, a miniRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

Some of the preferred chemical modifications described herein are believed to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. FIG. 5 provides some non-limiting examples of the chemical modification patterns which may be beneficial for achieving single stranded polynucleotide efficacy inside the cell. The chemical modification patterns may include combination of ribose, backbone, hydrophobic nucleoside and conjugate type of modifications. In addition, in some of the embodiments, the 5' end of the single polynucleotide may be chemically phosphorylated.

Figure 6:
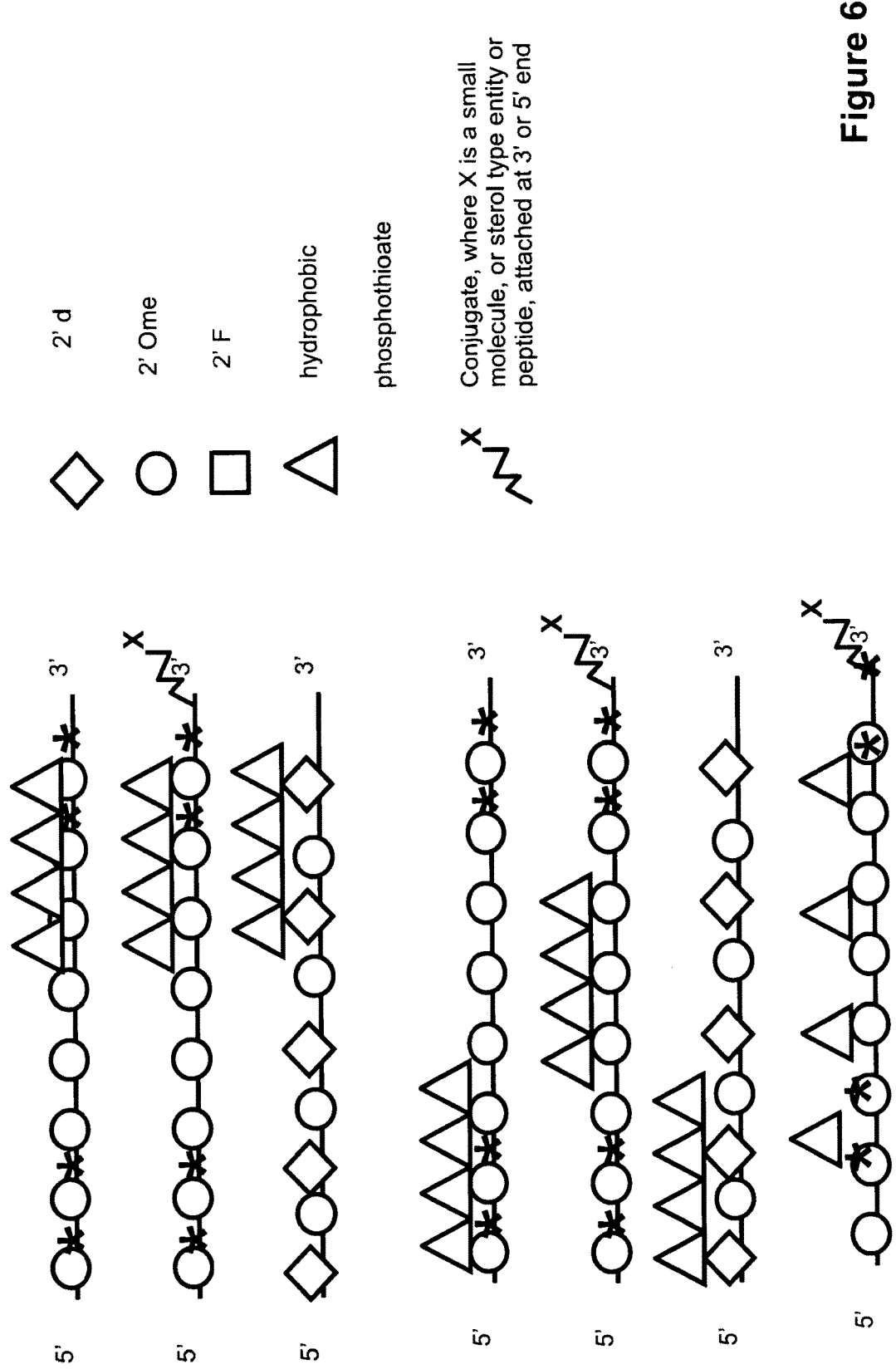
FIG. 6 is a schematic depicting examples of structural and chemical composition of RISC substrate inhibitors. Combinations of one or more chemical modifications can be used to mediate efficient uptake and efficient binding to preloaded RISC complex.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. FIG. 6 provides some non-limiting examples of the chemical modification patterns that may be beneficial for achieving single stranded polynucleotide efficacy inside the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp),asymmetric duplexed polynucleotides, and the like. Polynucleotides may be modified with wide variety of chemical modification patterns, including 5' end, ribose, backbone and hydrophobic nucleoside modifications.

In certain embodiments, the modified RNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

For purposes of the present invention, modified bases refer to nucleotide bases such as, for example, adenine, guanine, cytosine, thymine, and uracil, xanthine, inosine, and queuosine that have been modified by the replacement or addition of one or more atoms or groups. Some Examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine.

In another embodiment, chemical modifications of the first or second polynucleotide include, but not limited to, 5' position modification of Uridine and Cytosine (4-pyridyl, 2-pyridyl, indolyl, phenyl($C_6H_5OH$); tryptophanyl(C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet. 2003 Jan. 19:9; Reichhart J M et al. Genesis. 2002. 34(1-2):1604, Yu et al. 2002. Proc. Natl. Acad. Sci. USA 99:6047; Sui et al. 2002. Proc. Natl. Acad. Sci. USA 99:5515) viruses, polyamine or polycation conjugates using compounds such as polylysine, protamine, or Ni, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the miniRNA of the invention may be delivered by using various beta-glucan containing particles, such as those described in US 2005/0281781 A1, WO 2006/007372, and WO 2007/050643 (all incorporated herein by reference). In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Such beta-glucan based delivery system may be formulated for oral delivery, where the orally delivered beta-glucan/miniRNA constructs may be engulfed by macrophages or other related phagocytic cells, which may in turn release the miniRNA constructs in selected in vivo sites. Alternatively or in addition, the miniRNA may changes the expression of certain macrophage target genes.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. Biochimica et *Biophysica Acta* 1197:95-108).

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Moreover, the present invention provides for administering the subject oligonucleotides with an osmotic pump providing continuous infusion of such oligonucleotides, for example, as described in Ratajczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a subject in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$)mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a subject, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of subject body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimen may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or other-wise increase inhibition of the target gene.

Nucleic acid may be directly introduced into the cell (i.e., intracellularly); or introduced extracellularly into a cavity, interstitial space, into the circulation of an organism, introduced orally or by inhalation, or may be introduced by bathing a cell or organism in a solution containing the nucleic acid. Vascular or extravascular circulation, the blood or lymph system, and the cerebrospinal fluid are sites where the nucleic acid may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

Another use for the nucleic acids of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable nucleic acid of the invention which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Assays of Oligonucleotide Stability

In some embodiments, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol. Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease SI mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H.1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

The target RNA cleavage reaction achieved using the siRNAs of the invention is highly sequence specific. Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10. Additionally, numerous commercial entities, such as Dharmacon, and Invitrogen provide access to algorithms on their website. The Whitehead Institute also offers a free siRNA Selection Program. Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA may be defined functionally as a nucleotide sequence (or oligonucleotide sequence) that is capable of hybridizing with a portion of the target gene transcript. Examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), metabolic, viral diseases (i.e., HIV, Hepatitis C, flu), miRNA disorders, and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for inhibiting or preventing in a subject, a disease or condition associated with an aberrant or unwanted target gene expression or activity, by administering to the subject a nucleic acid of the invention. If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays known in the art. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the methods of the invention involve contacting a cell capable of expressing target gene with a nucleic acid of the invention that is specific for the target gene or protein (e.g., is specific for the mRNA encoded by said gene or specifying the amino acid sequence of said protein) such that expression or one or more of the activities of target protein is modulated. These methods can be performed in vitro (e.g., by culturing the cell with the agent), in vivo (e.g., by administering the agent to a subject), or ex vivo. The subjects may be first treated with a priming agent so as to be more responsive to the subsequent RNAi therapy if desired. As such, the present invention provides methods of treating a subject afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Thus the therapeutic agents of the invention can be administered to subjects to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons.

Figure 11:
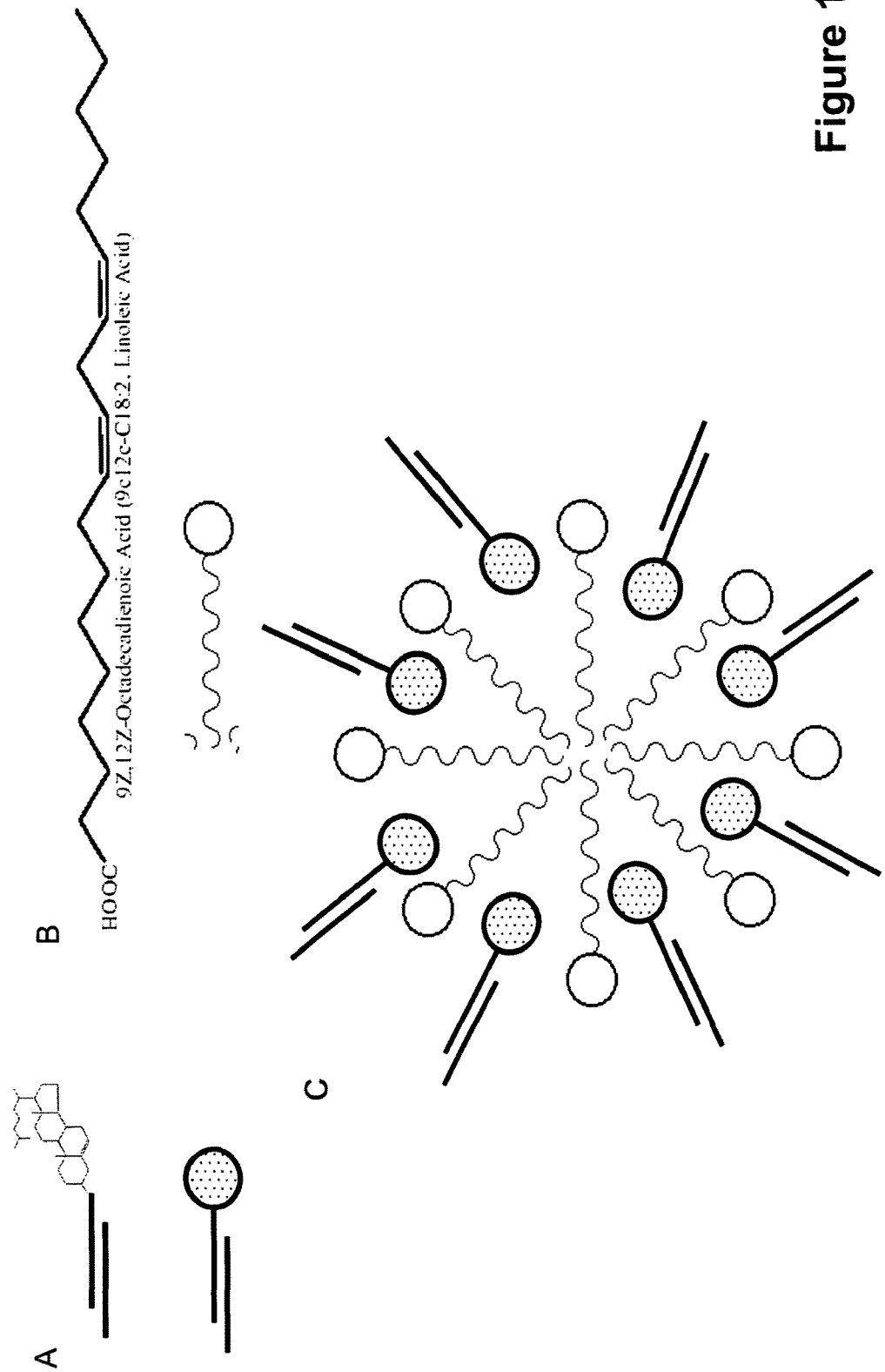
FIG. 11 is a schematic depicting micelle formation.

Thus, the present invention provides compositions and methods to provide polynucleotides in vivo by (1) synthesizing a polynucleotide, which contains hydrophobic entities (2) mixing this hydrophobicly modified polynucleotide with a fat emulsion to form micelles; and (3) administering the micelle to the patient or animal, for example intravenously, subcutaneously, topically, via catheter locally or orally (FIG. 11).

Nucleic acid molecules, or compositions comprising nucleic acid molecules, described herein may be used for delivery to any tissue or target. An example of a tissue or target is skin. The following exemplary discussion relates to use of the compositions of the invention for delivery of polynucleotides to the skin. The discussion is exemplary only and is not intended to limit the type of delivery or target useful according to the invention.

The compositions of the invention may be used for example to promote wound healing (including chronic wounds such as ulcers), and/or for prevention, reduction or inhibition of scarring, and/or promotion of re-epithelialisation of wounds. Such molecules may also be used for treatment or prevention of diseases, disorders or conditions such as treatment of cleft lip and palate (for example in conjunction with surgical repair of such conditions), reduction or inhibition of scarring and accelerated healing of tendons, and promotion of epithelial regeneration at sites of epithelial damage. In some aspects, nucleic acid molecules associated with the invention may also be used in treatment and/or prevention of fibrotic disorders, including pulmonary fibrosis, liver cirrhosis, scleroderma and glomerulonephritis, lung fibrosis, liver fibrosis, skin fibrosis, muscle fibrosis, radiation fibrosis, kidney fibrosis, proliferative vitreoretinopathy and uterine fibrosis.

A therapeutically effective amount of a nucleic acid molecule described herein may in some embodiments be an amount sufficient to bring about promotion of wound healing and/or inhibition of scarring and/or promotion of epithelial regeneration. The extent of promotion of wound healing and/or inhibition of scarring, or epithelial regeneration will in some instances be determined by, for example, a doctor or clinician. A suitable assessment of the extent of promotion of wound healing and/or the inhibition of scarring, or promotion of epithelial regeneration, may in some instances be determined by the doctor or clinician.

The ability of nucleic acid molecules associated with the invention to promote the healing of wounds may in some instances be measured with reference to properties exhibited by treated wounds. As used herein, a "treated wound" refers to a wound exposed to a therapeutically effective amount of a medicament such as a nucleic acid molecule of the invention, or a wound which has received treatment in accordance with the methods of the invention. In some instances, promotion of the healing of treated wounds may be indicated by an increased rate of epithelialisation as compared to control wounds. A molecule that is effective in accelerating the healing of wounds may in some instances be a molecule that promotes a more rapid re-constitution of a functional epithelial layer over a wounded area than would otherwise be the case. Promotion of healing of treated wounds can also in some embodiments be indicated by decreased width of a wound compared to control wounds at comparable time points.

As used herein, promotion of wound healing can encompass any increase in the rate of healing of a treated wound as compared with the rate of healing occurring in a control-treated or untreated wound. In some instances, promotion of wound healing may be assessed with respect to either comparison of the rate of re-epithelialisation achieved in treated and control wounds, or comparison of the relative width of treated and control wounds at comparable time points. In some aspects, a molecule that promotes wound healing may be a molecule that, upon administration, causes the wound to exhibit an increased rate of re-epithelialisation and/or a reduction of width compared to control wounds at comparable time points. In some embodiments, the promotion of wound healing may give rise to a rate of wound healing that is 5%, 10%, 20%, 30%, 40%, 50%, 60%, 70%, 80%, 90% or 100% greater than the rate occurring in control wounds.

Methods and compositions associated with the invention may be used for treatment of wounds of subjects that may otherwise be prone to defective, delayed or otherwise impaired re-epithelialisation, such as dermal wounds in the aged. Other non-limiting examples of conditions or disorders in which wound healing is associated with delayed or otherwise impaired re-epithelialisation include subjects suffering from diabetes, subjects with polypharmacy (for example as a result of old age), post-menopausal women, subjects susceptible to pressure injuries (for example paraplegics), subjects with venous disease, clinically obese subjects, subjects receiving chemotherapy, subjects receiving radiotherapy, subjects receiving steroid treatment, and immuno-compromised subjects. In some instances, defective re-epithelialisation response can contributes to infections at the wound site, and to the formation of chronic wounds such as ulcers.

In some aspects, chronic wounds exhibiting delayed wound healing response may be treated using methods and compositions associated with the invention. As used herein, a wound may be considered chronic if it does not show any healing tendency within approximately eight weeks of formation when subject to appropriate (conventional) therapeutic treatment. Examples of chronic wounds include venous ulcers, diabetic ulcers and decubitus ulcers, however chronic wounds may arise from otherwise normal acute injuries at any time. In some instances, chronic wounds can arise as a result of infection of the wound site, inadequate wound treatment, progressive tissue breakdown caused by venous, arterial, or metabolic vascular disease, pressure, radiation damage, or tumor. In some embodiments, methods associated with the invention may promote the re-epithelialisation of chronic wounds, and may also inhibit scarring associated with wound healing.

Methods associated with the invention are applied to prevention of acute wounds in subjects predisposed to impaired wound healing developing into chronic wounds. In other aspects, methods associated with the invention are applied to promote accelerated wound healing while preventing, reducing or inhibiting scarring for use in general clinical contexts. In some aspects, this can involve the treatment of surgical incisions and application of such methods may result in the prevention, reduction or inhibition of scarring that may otherwise occur on such healing. Such treatment may result in the scars being less noticeable and exhibiting regeneration of a more normal skin structure. In other embodiments, the wound that is treated is not a wound caused by a surgical incision. The wound may be subject to continued care and continued application of medicaments to encourage re-epithelialisation and closure of the wound.

In some aspects, methods associated with the invention may also be used in the treatment of wounds associated with grafting procedures. This can involve treatment at a graft donor site and/or at a graft recipient site. Grafts can in some embodiments involve skin, artificial skin, or skin substitutes. Methods associated with the invention can also be used for promoting epithelial regeneration. As used herein, promotion of epithelial regeneration encompasses any increase in the rate of epithelial regeneration as compared to the regeneration occurring in a control-treated or untreated epithelium. The rate of epithelial regeneration attained can in some instances be compared with that taking place in control-treated or untreated epithelia using any suitable model of epithelial regeneration known in the art. Promotion of epithelial regeneration may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in subjects suffering from epithelial damage.

Some instances where re-epithelialisation response may be defective include conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

In some aspects, methods associated with the invention are used to prevent, reduce or otherwise inhibit scarring. This can be applied to any site within the body and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may change the morphology and organization of collagen fibers and may result in making the scars less visible and blend in with the surrounding skin. As used herein, prevention, reduction or inhibition of scarring encompasses any degree of prevention, reduction or inhibition in scarring as compared to the level of scarring occurring in a control-treated or untreated wound.

Prevention, reduction or inhibition of dermal scarring can be assessed and/or measured with reference to microscopic and/or macroscopic characteristic of a treated scar as compared to the appearance of an untreated scar. As used herein, a "treated scar" refers to a scar formed on healing of a treated wound, whereas an "untreated scar" refers to a scar formed on healing of an untreated wound, or a wound treated with placebo or standard care. Suitable controls for comparison may involve matching of scar age, site, size and subject. Macroscopic assessment of scars may involve examination of parameters such as the color, height, surface texture and stiffness of the scar. In some instances, inhibition or reduction of scarring may be demonstrated when the pigmentation or redness of a treated scar more closely resembles that of unscarred skin than does the pigmentation of an untreated scar. In some instances, inhibition or reduction of scarring may be demonstrated when the height of a treated scar more closely resembles that of unscarred skin than does the height of an untreated scar. In some instances, inhibition or reduction of scarring may be demonstrated when the surface texture of a treated scar more closely resembles that of unscarred skin than does the surface texture of an untreated scar. In some instances inhibition or reduction of scarring may be demonstrated when the stiffness of a treated scar more closely resembles that of unscarred skin than does the stiffness of an untreated scar. An overall assessment of scarring can also be made using, for example, a Visual Analogue Scale or a digital assessment scale.

Microscopic assessment of scars may involve examination of parameters such as thickness of extracellular matrix (ECM) fibers, orientation of ECM fibers, ECM composition of the scar, and cellularity of the scar. In some instances, inhibition or reduction of scarring may be demonstrated when the thickness of ECM fibers in a treated scar more closely resembles the thickness of ECM fibers found in unscarred skin than does the thickness of fibers found in an untreated scar. In some instances, inhibition or reduction of scarring may be demonstrated when the orientation of ECM fibers in a treated scar more closely resembles the orientation of ECM fibers found in unscarred skin than does the orientation of such fibers found in an untreated scar. In some instances, inhibition or reduction of scarring may be demonstrated when the composition of ECM fibers in the dermis of a treated scar more closely resembles the composition of such fibers found in unscarred skin than does the composition found in an untreated scar. In some instances, inhibition or reduction of scarring may be demonstrated when the cellularity of a treated scar more closely resembles the cellularity of unscarred skin than does the cellularity of an untreated scar.

In some aspects, methods associated with the invention are used for cosmetic purposes, particularly when a wound is located at a prominent body site such as the face, neck and hands. Inhibition of scarring at such sites may contribute to improving the cosmetic appearance of the scar. Scarring is also responsible for a number of deleterious effects such as reduction of physical and mechanical function, particularly in the case of contractile scars (such as hypertrophic scars) and/or situations in which scars are formed across joints and alter the mechanical properties of scarred skin. Methods associated with the invention may be used to prevent, reduce or inhibit scarring of wounds covering joints of the body. In other embodiments, methods associated with the invention may be used to promote accelerated wound healing and/or prevent, reduce or inhibit scarring of wounds at increased risk of forming a contractile scar, and/or of wounds located at sites of high skin tension.

In some embodiments, methods associated with the invention can be applied to promoting wound healing and/or preventing, reducing or inhibiting scarring of wounds in which there is an increased risk of pathological scar formation. Pathological scarring, such as hypertrophic scars and keloids, may have more pronounced deleterious effects than normal scarring. For example, wounds of children, such as burns wounds, are also associated with increased hypertrophic scar formation. In some embodiments, methods described herein for promoting accelerated wound healing and/or preventing, reducing or inhibiting scarring are applied to wounds produced by surgical revision of pathological scars.

Aspects of the invention can be applied to wounds caused by burn injuries. Wound healing in response to burn injuries is frequently associated with adverse scarring outcomes, such as the formation of hypertrophic scars. Methods associated with the invention can be applied to treatment of all injuries involving damage to an epithelial layer, such as injuries to the skin in which the epidermis is damaged. Other non-limiting examples of injuries to epithelial tissue include injuries involving the respiratory epithelia, digestive epithelia or epithelia surrounding internal tissues or organs.

In some aspects, methods associated with the invention can also be used prophylactically, for example at sites where no wound exists but where a wound that would otherwise give rise to a scar or chronic wound is to be formed. For example, medicaments in accordance with the invention may be administered to sites that are to undergo wounding as a result of elective procedures such as surgery, or to sites that are believed to be at elevated risk of wounding. In some embodiments, administration of a medicament may occur around the time of wounding, or immediately prior to the forming of a wound, for example in the period up to six hours before wounding, or the medicaments may be administered at an earlier time before wounding, for example up to 48 hours before a wound is formed. One of ordinary skill in the art would be able to determine, based on a number of factors, the most advantageous time-frame, formulation and route of administration in a given context. Some non-limiting examples of factors that could be assessed for optimization include the formulation and route of administration of the selected medicament, the dosage of the medicament to be administered, the size and nature of the wound to be formed, and the biological status of the subject, including factors such as the subject's age, health, and predisposition to healing complications or adverse scarring.

In some aspects, methods associated with the invention can be applied to promote wound healing and/or inhibit scarring after a wound has been formed. Administration can occur at any time up until the healing process has been completed, even if the wound has already partially healed. The timing of administration to promote accelerated wound healing and/or prevent, reduce or inhibit scarring can depend on several factors including the nature of the wound in question, the degree of damage within the wound, and the size of the wounded area. In some embodiments, if the wound is large, administration of a medicament relatively late in the healing response may still be able to promote wound healing and/or prevent, reduce or inhibit scarring. In some embodiments, administration of a medicament may occur within the first 24-48 hours after a wound is formed. However, in other embodiments, administration of a medicaments of the invention may be administered 3, 4, 5, 6, 7, 8, 9, 10 or more than 10 days after wounding. Methods and medicaments of the invention may be administered on one or more occasions as necessary in order to promote accelerated wound healing and/or prevent, reduce or inhibit scarring. For instance therapeutically effective amounts of the medicaments may be administered to a wound as often as required until the healing process has been sufficiently advanced or completed. For example, in some embodiments, the medicaments of the invention may be administered daily or twice daily to a wound for at least the first three days following the formation of the wound.

In some instances, the methods or medicaments of the invention may be administered both before and after formation of a wound. It will be appreciated that the amount of a medicament of the invention that should be applied to a wound depends on a number of factors such as the biological activity and bioavailability of the agent present in the medicament, which depends, among other factors, on the nature of the agent and the mode of administration of the medicament. Other factors in determining a suitable therapeutic amount of a medicament may include the half-life of the agent in the subject being treated; the specific condition to be treated, and characteristics of the subject such as the age of the subject. The frequency of administration will also be influenced by the above-mentioned factors including the half-life of the chosen agent. Typically a cream or ointment containing an agent of the invention may be administered to a target tissue such that the concentration of the agent at a wound is maintained at a level suitable for having a therapeutic effect. In some instances, this may require administration daily or several times daily.

Compositions and medicaments associated with the invention may be administered by any suitable route capable of achieving the desired effect of promoting wound healing and/or preventing, reducing or inhibiting scarring. In some embodiments, the medicaments are administered locally at a wound site. For dermal wounds, agents of the invention may be administered by means of intradermal injection. Accordingly, compositions and medicaments associated with the invention may comprise injectable solutions, and in some instances may be injected, for example, around the margins of a site of epithelial damage or a site likely to be damaged. In some embodiments, compositions and medicaments associated with the invention may also be administered in a topical form to promote accelerated wound healing and/or prevention, reduction or inhibition of scarring. In some embodiments, administration of compositions and medicaments associated with the invention comprise part of an initial treatment of a wound or scar, while in other embodiments, administration of compositions and medicaments associated with the invention comprise follow-up care for a wound or scar.

Target Genes

It should be appreciated that based on the RNAi molecules designed and disclosed herein, one of ordinary skill in the art would be able to design such RNAi molecules to target a variety of different genes depending on the context and intended use. For purposes of promoting wound healing or preventing, reducing or inhibiting scarring, one of ordinary skill in the art would appreciate that a variety of suitable target genes could be identified based at least in part on the known or predicted functions of the genes, and/or the known or predicted expression patterns of the genes. Several non-limiting examples of genes that could be targeted by RNAi molecules for promoting wound healing or preventing, reducing or inhibiting scarring include genes that encode for the following proteins: Transforming growth factor β (TGFβ1, TGFβ2, TGFβ3), Osteopontin, Connective tissue growth factor (CTGF), Platelet-derived growth factor (PDGF), Hypoxia inducible factor-1α (HIF1α), Collagen I and/or III, Prolyl 4-hydroxylase (P4H), Procollagen C-protease (PCP), Matrix metalloproteinase 2, 9 (MMP2, 9), Integrins, Connexin, Histamine H1 receptor, Tissue transglutaminase, Mammalian target of rapamycin (mTOR), HoxB13, VEGF, IL-6, SMAD proteins, Ribosomal protein S6 kinases (RSP6) and Cyclooxygenase-2 (COX-2).

Transforming growth factor β proteins, for which three isoforms exist in mammals (TGFβ1, TGFβ2, TGFβ3), are secreted proteins belonging to a superfamily of growth factors involved in the regulation of many cellular processes including proliferation, migration, apoptosis, adhesion, differentiation, inflammation, immuno-suppression and expression of extracellular proteins. These proteins are produced by a wide range of cell types including epithelial, endothelial, hematopoietic, neuronal, and connective tissue cells. Representative Genbank accession numbers providing DNA and protein sequence information for human TGFβ1, TGFβ2 and TGFβ3 are BT007245, BC096235, and X14149, respectively.

Osteopontin (OPN), also known as Secreted phosphoprotein 1 (SPP1), Bone Sialoprotein 1 (BSP-1), and early T-lymphocyte activation (ETA-1) is a secreted glycoprotein protein that binds to hydroxyapatite. OPN has been implicated in a variety of biological processes including bone remodeling, immune functions, chemotaxis, cell activation and apoptosis. Osteopontin is produced by a variety of cell types including fibroblasts, preosteoblasts, osteoblasts, osteocytes, odontoblasts, bone marrow cells, hypertrophic chondrocytes, dendritic cells, macrophages, smooth muscle, skeletal muscle myoblasts, endothelial cells, and extraosseous (non-bone) cells in the inner ear, brain, kidney, deciduum, and placenta. Representative Genbank accession number providing DNA and protein sequence information for human Osteopontin are NM_000582.2 and X13694.

Connective tissue growth factor (CTGF), also known as Hypertrophic chondrocyte-specific protein 24, is a secreted heparin-binding protein that has been implicated in wound healing and scleroderma. Connective tissue growth factor is active in many cell types including fibroblasts, myofibroblasts, endothelial and epithelial cells. Representative Genbank accession number providing DNA and protein sequence information for human CTGF are NM_001901.2 and M92934.

The Platelet-derived growth factor (PDGF) family of proteins, including several isoforms, are secreted mitogens. PDGF proteins are implicated in wound healing, at least in part, because they are released from platelets following wounding. Representative Genbank accession numbers providing DNA and protein sequence information for human PDGF genes and proteins include X03795 (PDGFA), X02811 (PDGFB), AF091434 (PDGFC), AB033832 (PDGFD).

Hypoxia inducible factor-1α (HIF1α), is a transcription factor involved in cellular response to hypoxia. HIF1α is implicated in cellular processes such as embryonic vascularization, tumor angiogenesis and pathophysiology of ischemic disease. A representative Genbank accession number providing DNA and protein sequence information for human HIF1α is U22431.

Collagen proteins are the most abundant mammalian proteins and are found in tissues such as skin, tendon, vascular, ligature, organs, and bone. Collagen I proteins (such as COL1A1 and COL1A2) are detected in scar tissue during wound healing, and are expressed in the skin. Collagen III proteins (including COL3A1) are detected in connective tissue in wounds (granulation tissue), and are also expressed in skin. Representative Genbank accession numbers providing DNA and protein sequence information for human Collagen proteins include: Z74615 (COL1A1), J03464 (COL1A2) and X14420 (COL3A1).

Prolyl 4-hydroxylase (P4H), is involved in production of collagen and in oxygen sensing. A representative Genbank accession number providing DNA and protein sequence information for human P4H is AY198406.

Matrix metalloproteinase 2, 9 (MMP2, 9) belong to the metzincin metalloproteinase superfamily and are zinc-dependent endopeptidases. These proteins are implicated in a variety of cellular processes including tissue repair. Representative Genbank accession numbers providing DNA and protein sequence information for human MMP proteins are M55593 (MMP2) and J05070 (MMP9).

Integrins are a family of proteins involved in interaction and communication between a cell and the extracellular matrix. Vertebrates contain a variety of integrins including $\alpha_1\beta_1$, $\alpha_2\beta_1$, $\alpha_4\beta_1$, $\alpha_5\beta_1$, $\alpha_6\beta_1$, $\alpha_L\beta_2$, $\alpha_M\beta_2$, $\alpha_{IIb}\beta_3$, $\alpha_v\beta_3$, $\alpha_v\beta_5$, $\alpha_v\beta_6$, $\alpha_6\beta_4$.

Connexins are a family of vertebrate transmembrane proteins that form gap junctions. Several examples of Connexins, with the accompanying gene name shown in brackets, include Cx23 (GJE1), Cx25 (GJB7), Cx26 (GJB2), Cx29 (GJE1), Cx30 (GJB6), Cx30.2 (GJC3), Cx30.3 (GJB4), Cx31 (GJB3), Cx31.1 (GJB5), Cx31.9 (GJC1/GJD3), Cx32 (GJB1), Cx33 (GJA6), Cx36 (GJD2/GJA9), Cx37 (GJA4), Cx39 (GJD4), Cx40 (GJA5), Cx40.1 (GJD4), Cx43 (GJA1), Cx45 (GJC1/GJA7), Cx46 (GJA3), Cx47 (GJC2/GJA12), Cx50 (GJA8), Cx59 (GJA10), and Cx62 (GJA 10).

Histamine H1 receptor (HRH1) is a metabotropic G-protein-coupled receptor involved in the phospholipase C and phosphatidylinositol (PIP2) signaling pathways. A representative Genbank accession number providing DNA and protein sequence information for human HRH1 is Z34897.

Tissue transglutaminase, also called Protein-glutamine gamma-glutamyltransferase 2, is involved in protein cross-linking and is implicated is biological processes such as apoptosis, cellular differentiation and matrix stabilization. A representative Genbank accession number providing DNA and protein sequence information for human Tissue transglutaminase is M55153.

Mammalian target of rapamycin (mTOR), also known as Serine/threonine-protein kinase mTOR and FK506 binding protein 12-rapamycin associated protein 1 (FRAP1), is involved in regulating cell growth and survival, cell motility, transcription and translation. A representative Genbank accession number providing DNA and protein sequence information for human mTOR is L34075.

HoxB13 belongs to the family of Homeobox proteins and has been linked to functions such as cutaneous regeneration and fetal skin development. A representative Genbank accession number providing DNA and protein sequence information for human HoxB13 is U57052.

Vascular endothelial growth factor (VEGF) proteins are growth factors that bind to tyrosine kinase receptors and are implicated in multiple disorders such as cancer, age-related macular degeneration, rheumatoid arthritis and diabetic retinopathy. Members of this protein family include VEGF-A, VEGF-B, VEGF-C and VEGF-D. Representative Genbank accession numbers providing DNA and protein sequence information for human VEGF proteins are M32977 (VEGF-A), U43368 (VEGF-B), X94216 (VEGF-C), and D89630 (VEGF-D).

Interleukin-6 (IL-6) is a cytokine involved in stimulating immune response to tissue damage. A representative Genbank accession number providing DNA and protein sequence information for human IL-6 is X04430.

SMAD proteins (SMAD1-7, 9) are a family of transcription factors involved in regulation of TGFβ signaling. Representative Genbank accession numbers providing DNA and protein sequence information for human SMAD proteins are U59912 (SMAD1), U59911 (SMAD2), U68019 (SMAD3), U44378 (SMAD4), U59913 (SMAD5), U59914 (SMAD6), AF015261 (SMAD7), and BC011559 (SMAD9).

Ribosomal protein S6 kinases (RSK6) represent a family of serine/threonine kinases involved in activation of the transcription factor CREB. A representative Genbank accession number providing DNA and protein sequence information for human Ribosomal protein S6 kinase alpha-6 is AF184965.

Cyclooxygenase-2 (COX-2), also called Prostaglandin G/H synthase 2 (PTGS2), is involved in lipid metabolism and biosynthesis of prostanoids and is implicated in inflammatory disorders such as rheumatoid arthritis. A representative Genbank accession number providing DNA and protein sequence information for human COX-2 is AY462100.

The invention also encompasses diagnostic uses as well as prophylactic, therapeutic and research uses.

Formulations include sterile or non-sterile aqueous or non-aqueous solutions, suspensions, and emulsions.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment, diagnosis, or prophylaxis of a disease.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic or diagnostic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said instructions indicate a dosing regimen for preventing, treating or managing a subject with a disease.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Neutral Nanotransporters for Delivery of Nucleic Acids

Described herein is the development of neutral fat formulations for nucleic acid delivery. Formulations were developed to allow efficient incorporation of nucleic acids into non-charged mixtures, offering the significant advantage of lower toxicity relative to previously described formulations for nucleic acid delivery.

Figure 2:
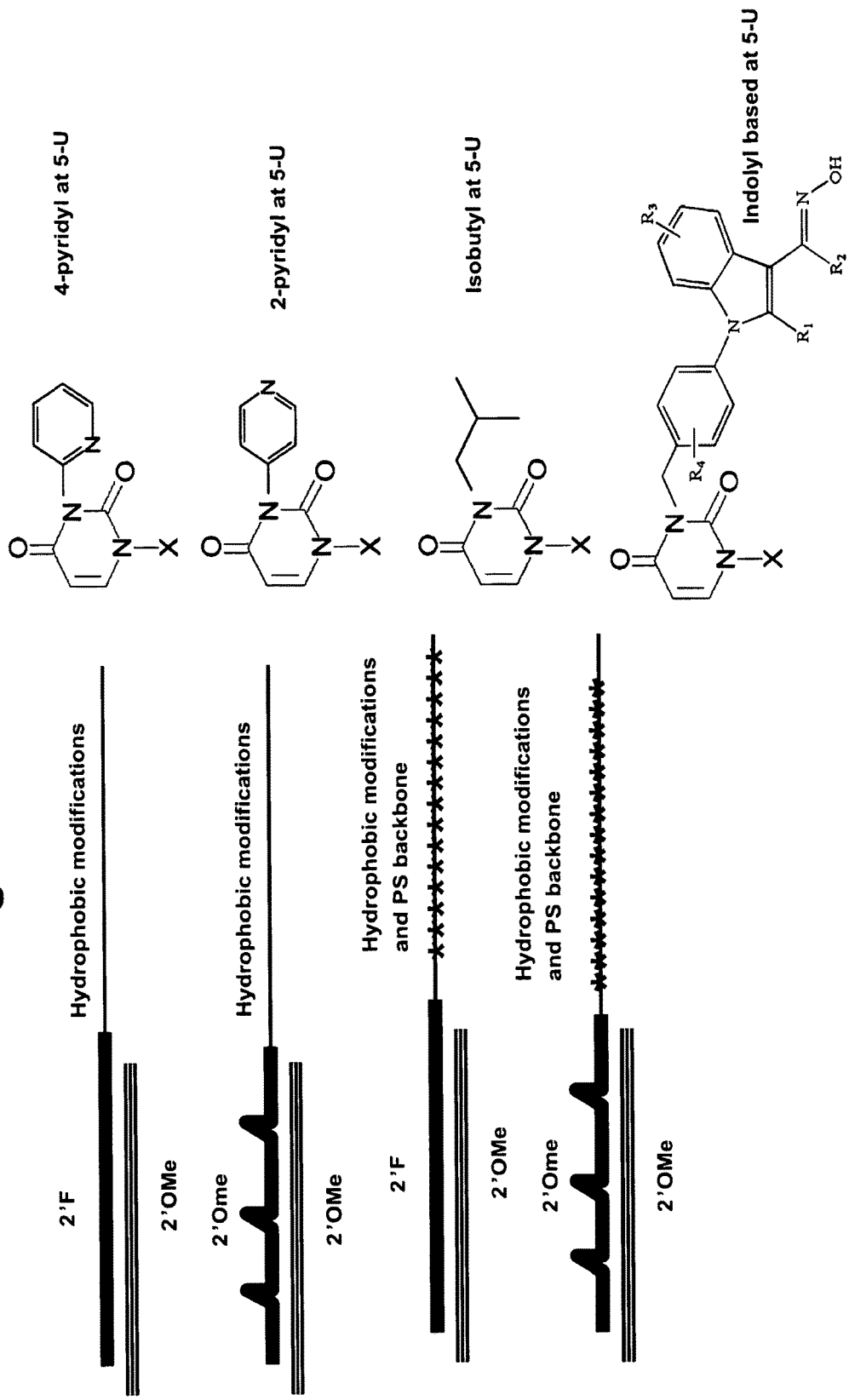
FIG. 2 is a schematic depicting asymmetric dsRNA molecules with different chemical modification patterns. Several examples of chemical modifications that might be used to increase hydrophobicity are shown including 4-pyridyl, 2-pyridyl, isobutyl and indolyl based position 5 uridine modifications.
Figure 3:
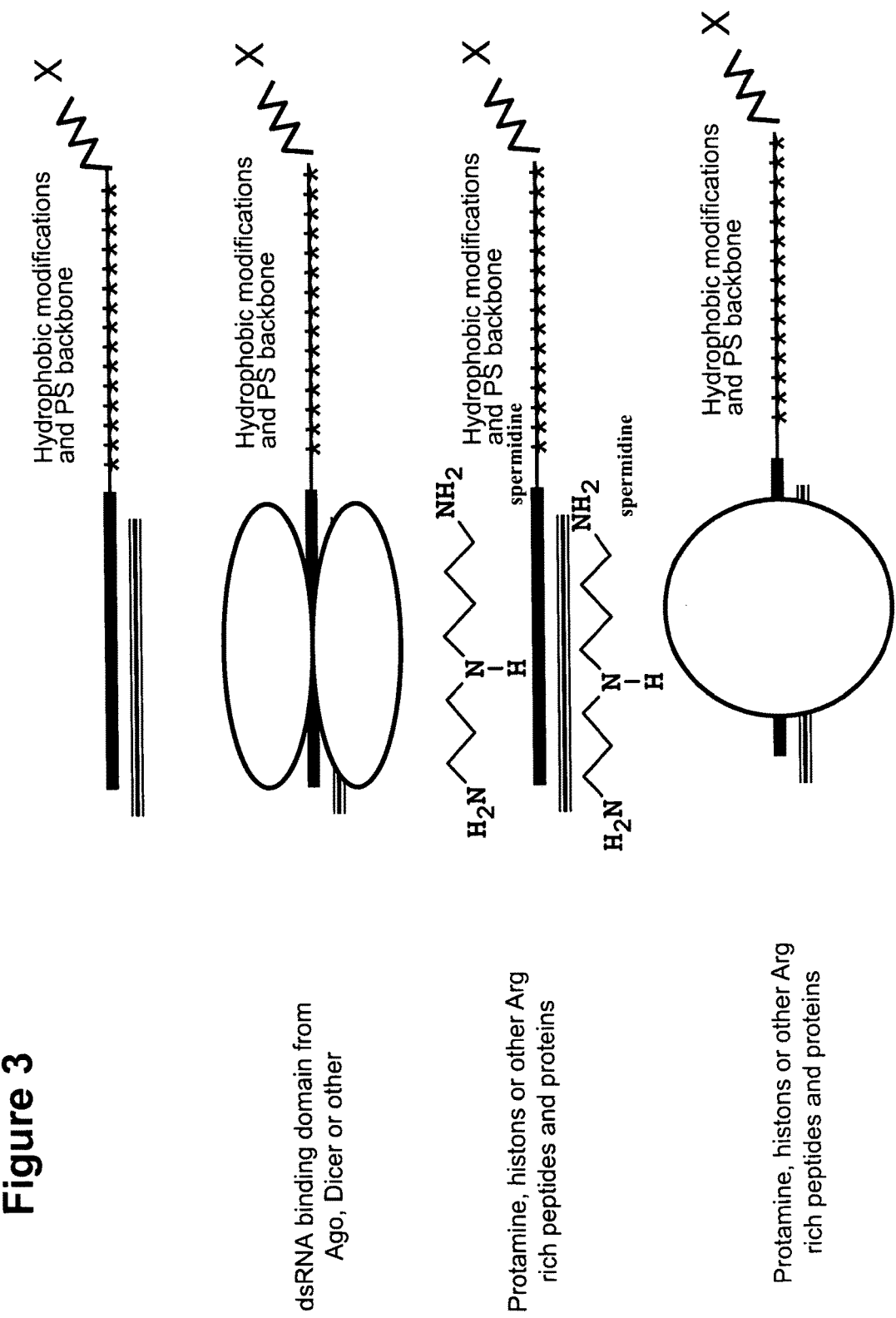
FIG. 3 is a schematic depicting the use of dsRNA binding domains, protamine (or other Arg rich peptides), spermidine or similar chemical structures to block duplex charge to facilitate cellular entry.

The hydrophobicity of nucleic acids can be increased by conjugating them to sterol-type molecules, as shown in a schematic in FIG. 1C. The sterol-type molecule can be conjugated to either strand of the double stranded nucleic acid molecule. FIG. 2 lists several examples of chemical modifications that can be used to increase hydrophobicity including 4-pyridyl, 2-pyridyl, isobutyl and indolyl based position 5 uridine modifications. FIG. 2 also shows a schematic depicting double stranded RNA molecules with a variety of chemical modification patterns including hydrophobic modifications that increase the hydrophobicity of the nucleic acid molecule. Proteins or peptides such as protamine (or other Arg rich peptides), spermidine or other similar chemical structures can also be used to block duplex charge and facilitate cellular entry (FIG. 3). Increased hydrophobicity can be achieved through either covalent or non-covalent modifications. Several positively charged chemicals, which might be used for polynucleotide charge blockage are depicted in FIG. 4.

FIG. 5 depicts single stranded polynucleotides, representing a guide strand in a duplex molecule, with a variety of chemical modifications including 2'd, 2'OMe, 2'F, hydrophobic modifications, phosphorothioate modifications, and attachment of conjugates such as "X" in FIG. 5, where X can be a small molecule with high affinity to a PAZ domain, or sterol-type entity. Similarly, FIG. 6 depicts single stranded polynucleotides, representing a passenger strand in a duplex molecule, with proposed structural and chemical compositions of RISC substrate inhibitors. Combinations of chemical modifications can ensure efficient uptake and efficient binding to preloaded RISC complexes.

Figure 7:
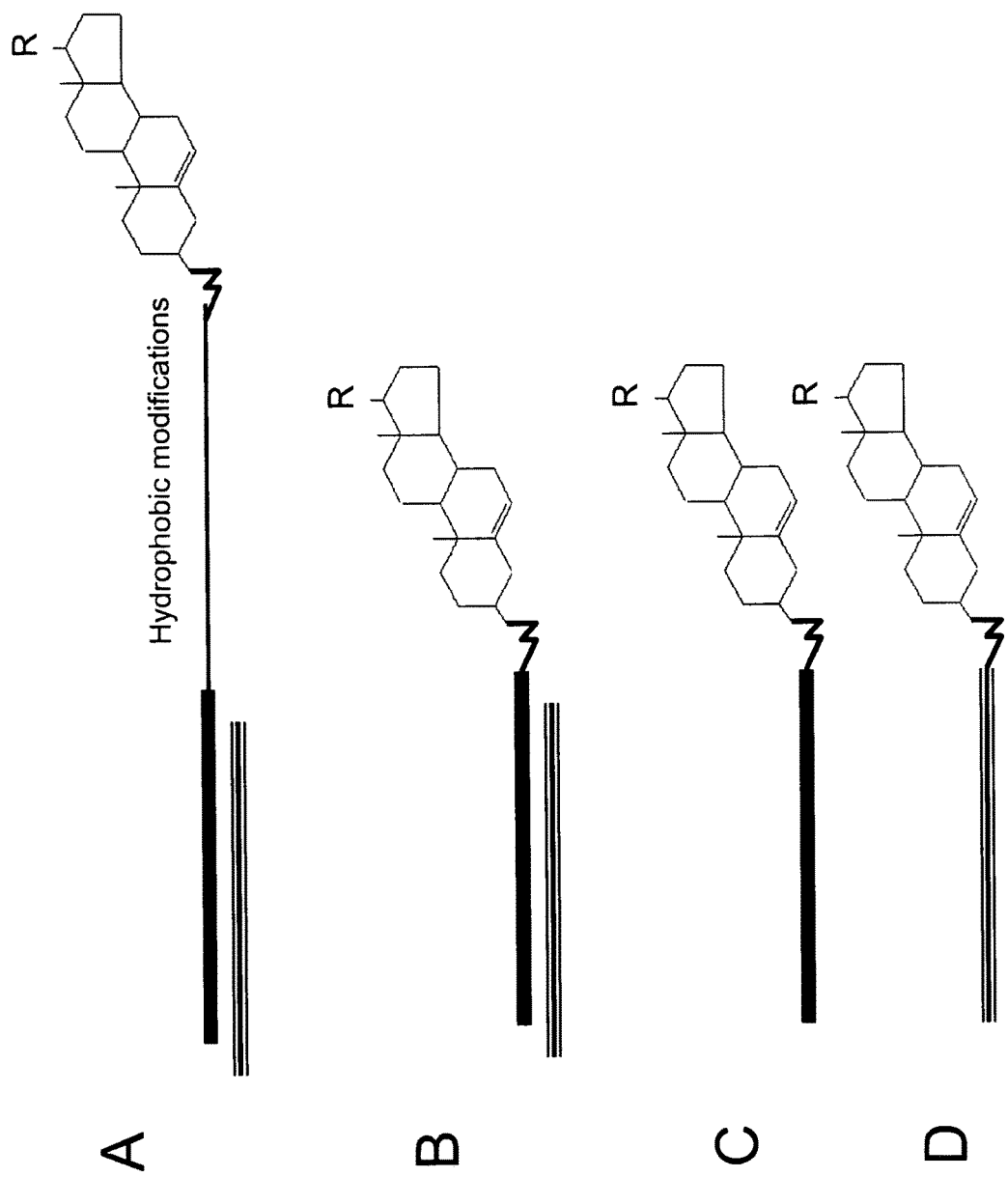
FIG. 7 is a schematic depicting structures of polynucleotides with sterol type molecules attached, where R represent a polycarbonic tail of 9 carbons or longer.
Figure 10:
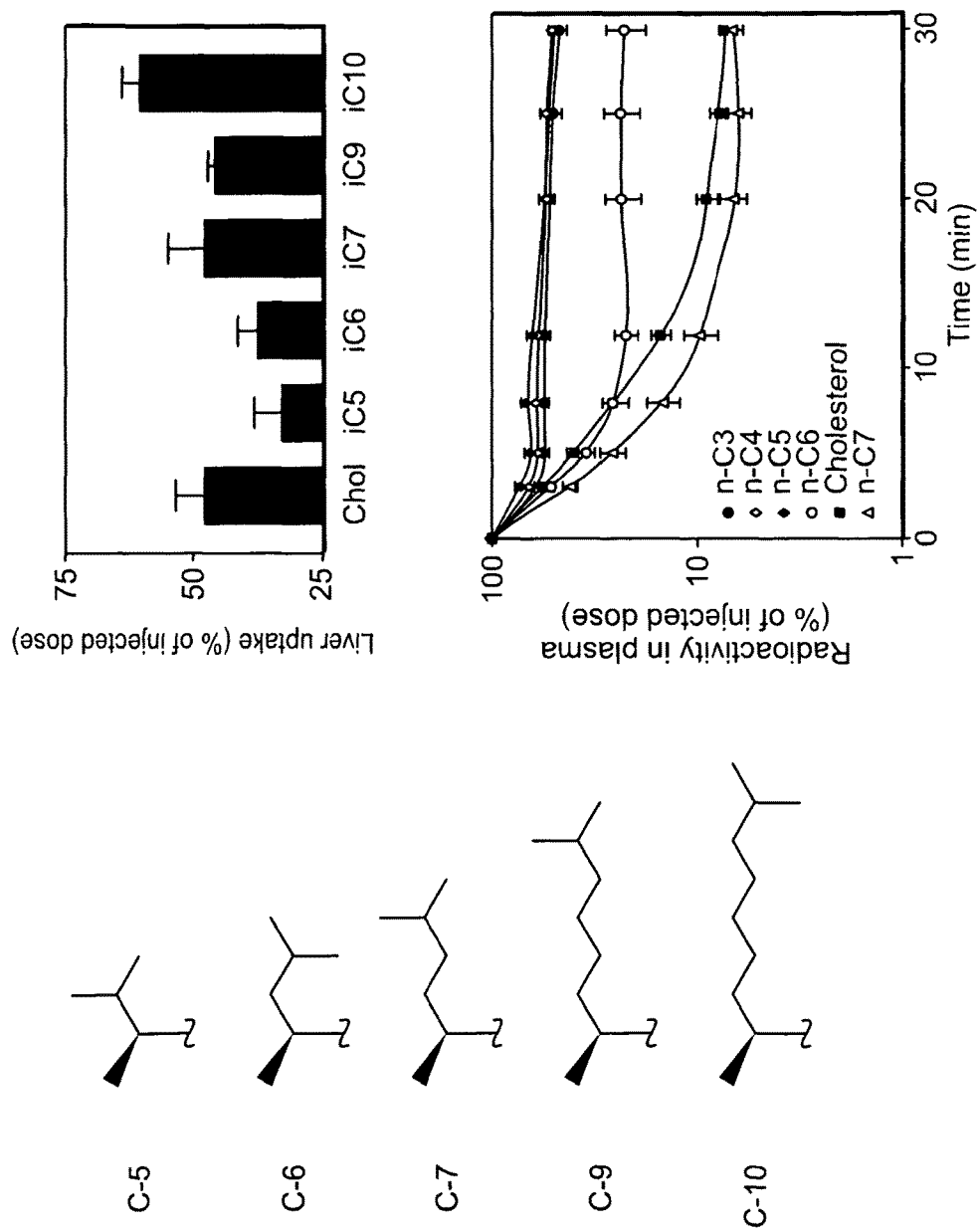
FIG. 10 presents schematics and graphs demonstrating that the percentage of liver uptake and plasma clearance of lipid emulsions containing sterol type molecules is directly affected by the size of the polycarbon chain attached at position 17. This figure is adapted from Martins et al, Journal of Lipid Research (1998).

FIG. 7 depicts structures of polynucleotides, with or without hydrophobic modifications within the polynucleotide, with sterol-type molecules attached. R represents a polycarbonic tail of 9 carbons or longer. FIG. 8 presents examples of naturally occurring phytosterols with a polycarbon chain longer than 8 attached at position 17. More than 250 different types of phytosterols are known. FIG. 9 presents examples of sterol-like structures with variations in the sizes of the polycarbon chains attached at position 17. Optimization of such characteristics can improve uptake properties of the RNAi molecules. FIG. 10 presents data adapted from Martins et al. (J Lipid Research), showing that the percentage of liver uptake and plasma clearance of lipid emulsions containing sterol-type molecules is directly affected by the size of the attached polycarbon chain at position 17. FIG. 11 depicts a micelle formed from a mixture of polynucleotides attached to hydrophobic conjugates and fatty acids. FIG. 12 describes how alteration in lipid composition can affect pharmacokinetic behavior and tissue distribution of hydrophobically modified and/or hydrophobically conjugated polynucleotides. In particular, the use of lipid mixtures that are enriched in linoleic acid and cardiolipin results in preferential uptake by cardiomyocites.

Nucleic acid molecules that are chemically modified and/or conjugated to sterol-type molecules are capable of self-delivery, as demonstrated in FIG. 13. The double stranded RNA molecules depicted in FIG. 13 are called "sd" RNA molecules, meaning "self-delivering" RNA molecules. Three generations of sd-rxRNA molecules were developed: generation I (GI), generation IIa (GIIa) and generation IIb (GIIb), with variations in the chemical modification patterns incorporated. Highly effective compounds were found to have the following characteristics: antisense strands of 17-21 nucleotides, sense strands of 10-15 nucleotides, single-stranded regions that contained 2-12 phosphorothioate modifications, preferentially 6-8 phosphorothioate modifications, and sense strands in which the majority of nucleotides were 2'OMe modified, with or without phosphorothioate modification. As shown in the graph in FIG. 13, these molecules were highly effective in achieving silencing of a target gene. Significantly, any linker chemistry can be used to attach these nucleic acid molecules to hydrophobic moieties such as cholesterol at the 3' end of the sense strand. Version GIIa-b of these RNA compounds demonstrate that elimination of 2'F content, predicted to significantly decrease toxicity, has no impact on efficacy.

Modifications and conjugations described herein, to increase the hydrophobicity of nucleic acid molecules, can be applied to any type of nucleic acid molecule. Several examples of types of nucleic acids that could be formulated and delivered using methods and compositions described herein are presented in FIG. 14 including conventional siRNAs, longer siRNAs single stranded oligos, antisense, antogamirs and sd-rxRNA. The nucleic acid molecule is modified such that its hydrophobicity is substantially increased. This can be achieved by modifying bases, sugars or nucleic acid backbone or/and by linking a hydrophobic molecule to the nucleic acid. The hydrophobic molecule can be attached anywhere in the compound and can include, for example, a fatty acid, sterol, vitamin, small molecule or peptide. The hydrophobic molecule can be covalently or non covalently attached.

Figure 15:
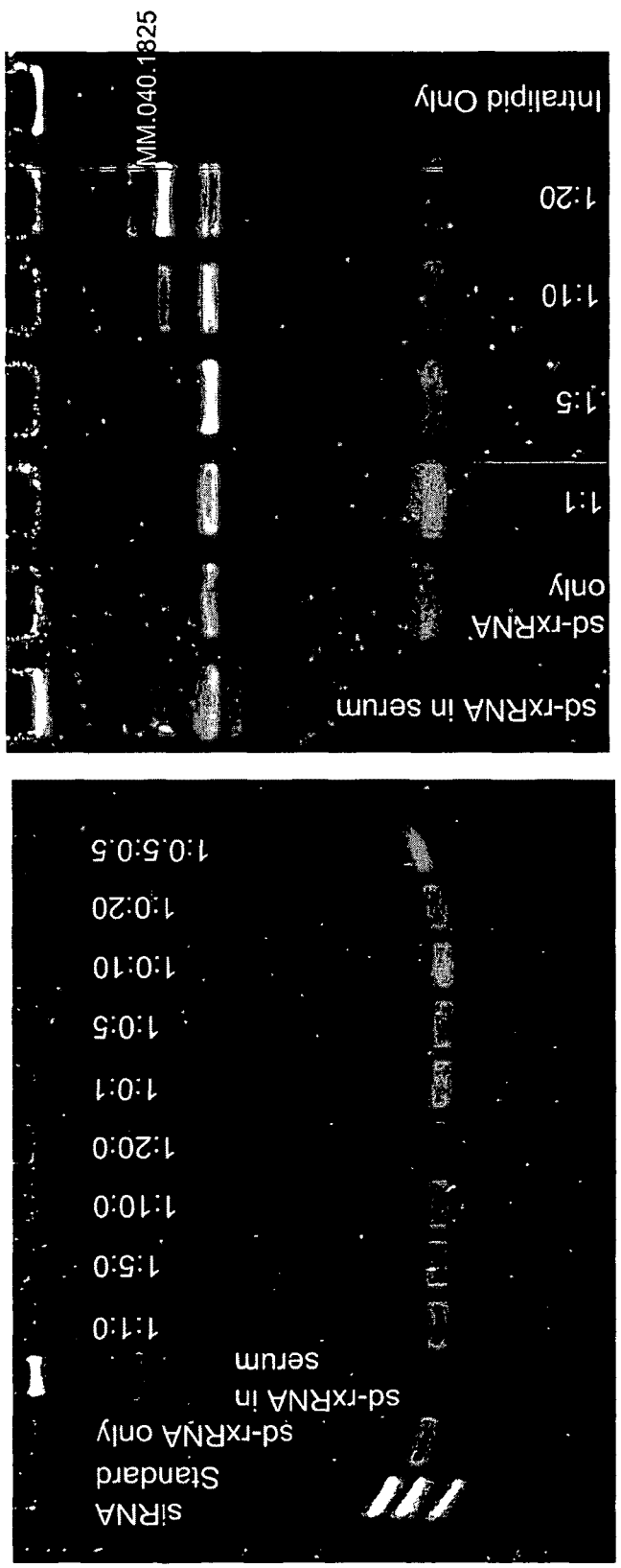
FIG. 15 presents gels that demonstrate a lack of complex formation between hydrophobic oligonucleotides (sd-rxRNA) and neutral fat formulations. Panel A shows a lack of complex formation with a DOPC:DOPE mixture. Panel B demonstrate lack of complex formation with Intralipid. The complex formation is evaluated by complexing reagents and evaluating a shift in oligonucleotide band formation using a non-denaturing polyacrylamide gel. The position of the oligonucleotide is determined by staining.

Hydrophobic oligonucleotides (sd-rxRNA) and neutral fat formulations alone were not found to form complexes (FIG. 15). FIG. 15A shows a lack of complex formation with a DOPC:DOPE mixture and FIG. 15B shows a lack of complex formation with Intralipid. The complex formation was evaluated by complexing reagents and evaluating a shift in oligonucleotide band formation using a non-denaturing polyacrylamide gel. The position of the oligonucleotide is determined by staining.

Figure 16:
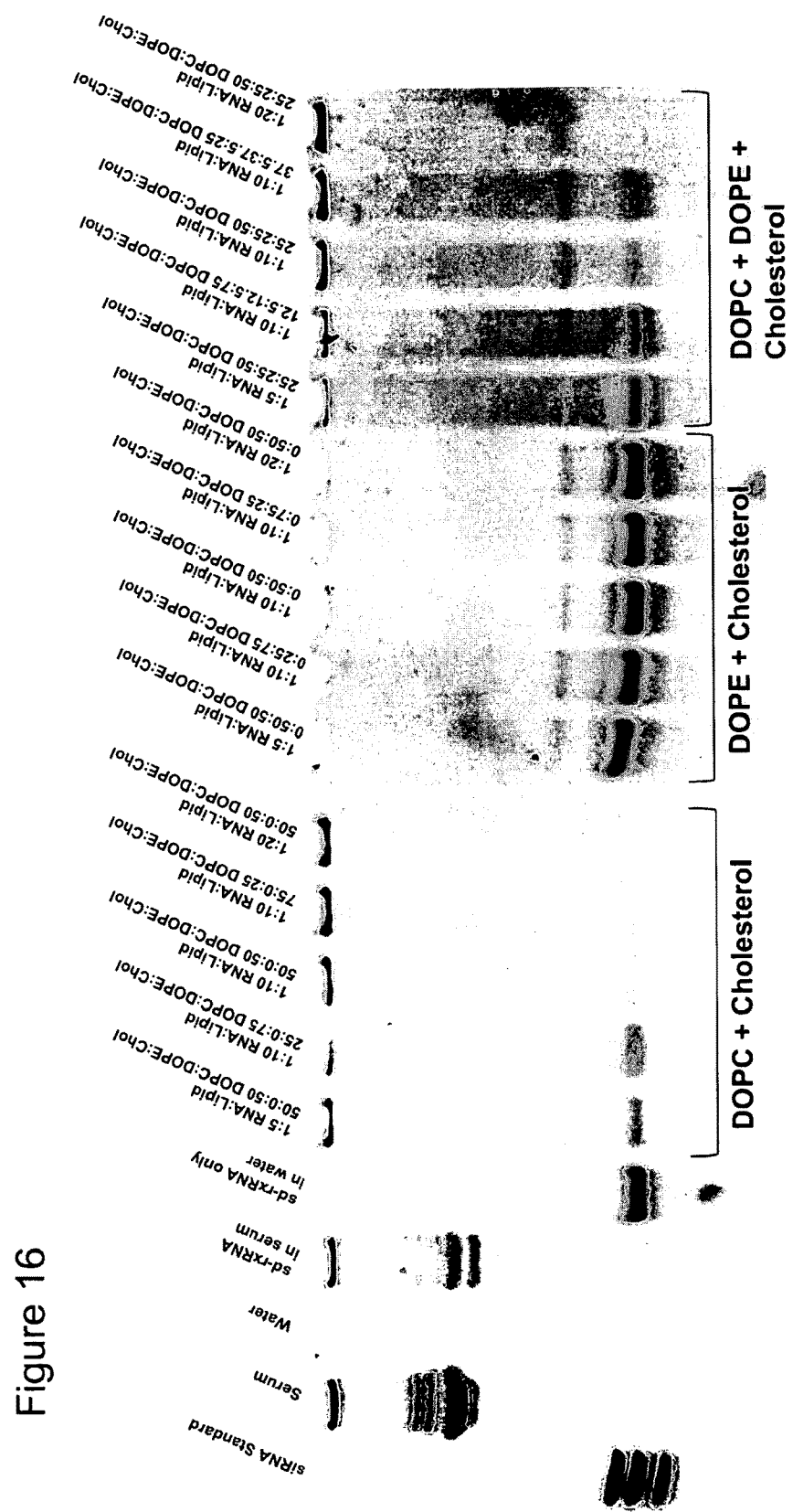
FIG. 16 presents gels demonstrating that the simultaneous presence of DOPC and Cholesterol results in a hydrophobic nucleic acid complexing with neutral lipid formulations. As low as 1:5 weight (lipid to oligonucleotide) ratio was sufficient to produce a significant fraction of encapsulated oligonucleotide. In the context of DOPC:Cholesterol formulation, other neutral lipids can be added without interfering with particle formation. For example, DOPC:cholesterol: DOPE.
Figure 17:
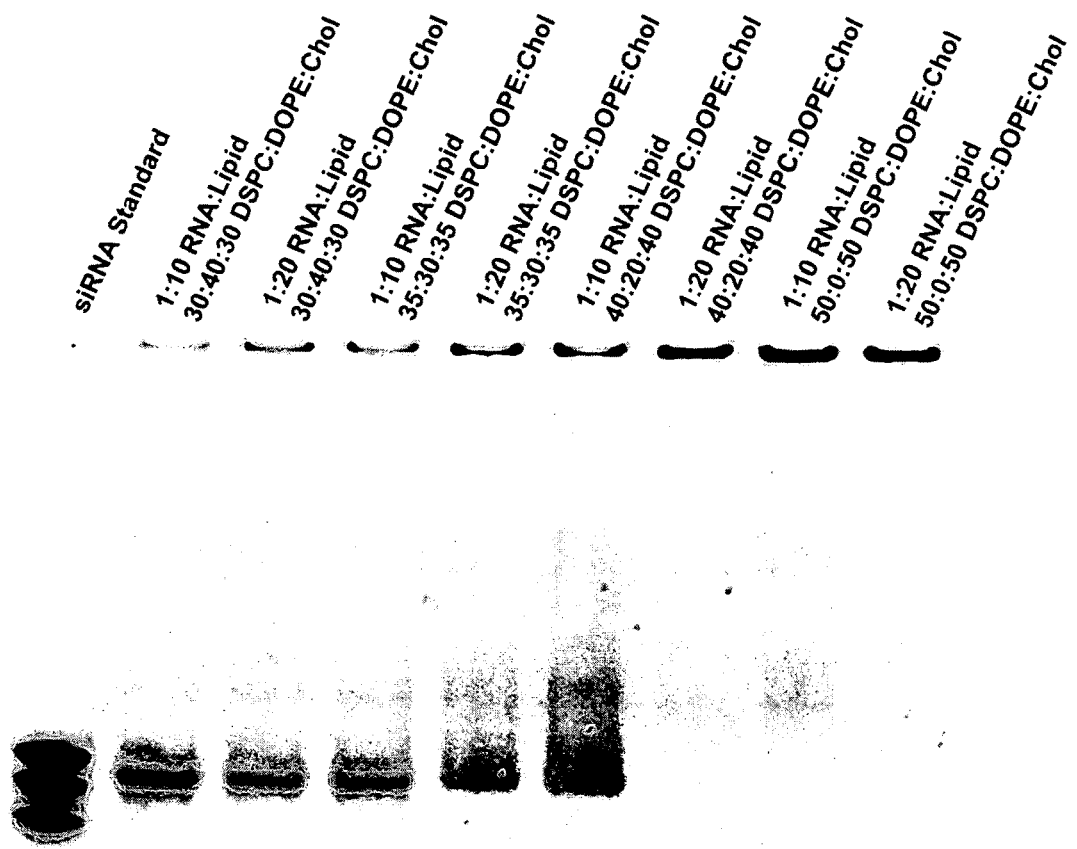
FIG. 17 presents a gel demonstrating that DSPC (saturated fatty acids) may take place of DOPC without any impact on efficiency of complex formation
Figure 18:
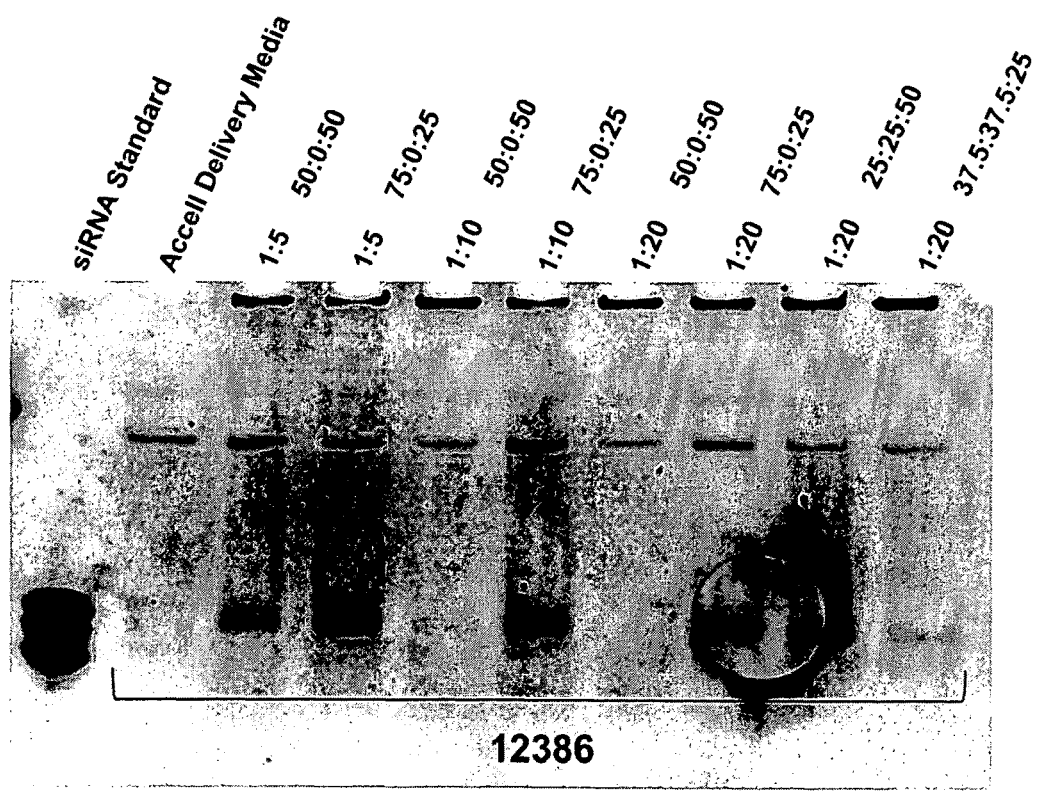
FIG. 18 presents a gel demonstrating DOPC/Intralipid/ Cholesterol Formulation involving sd-rxRNA (12386). Complexes were still present when diluted to 500 nM from 1 µM with Accell media.
Figure 19:
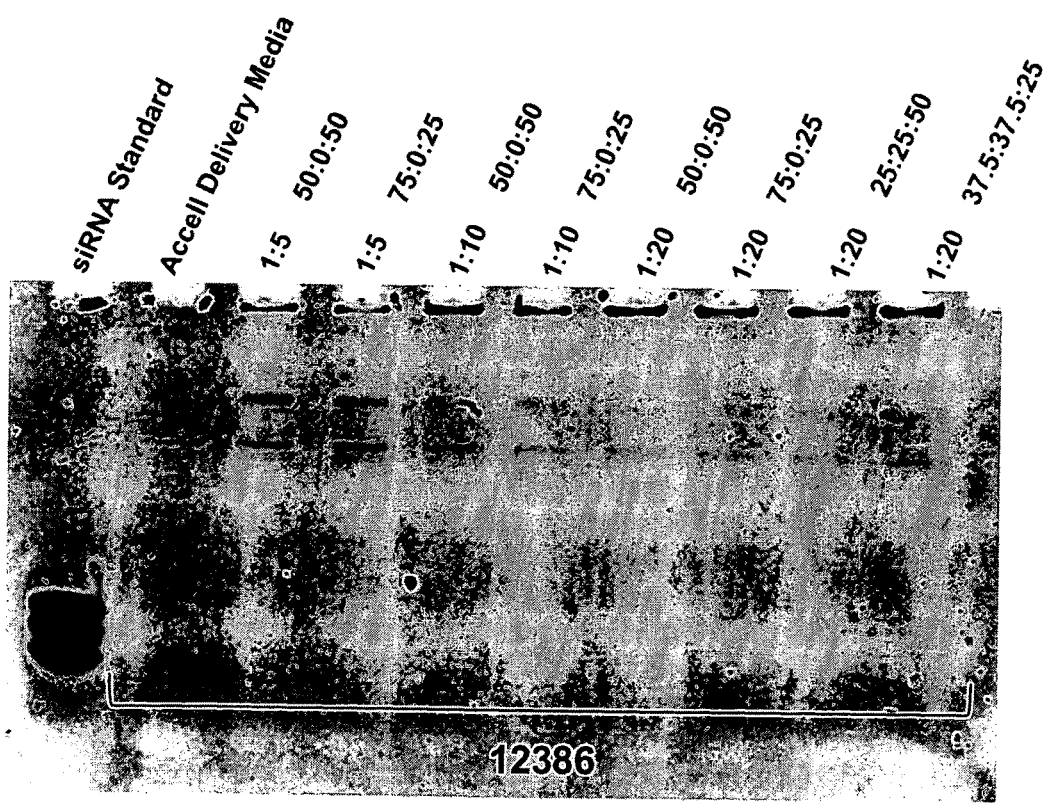
FIG. 19 presents a gel demonstrating DOPC/Intralipid/ Cholesterol Formulation involving sd-rxRNA (12386). Complexes were still found to be present when diluted to 500 nM from 5 µM with Accell media. More RNA appeared to be complexed here than when diluting to 500 nM from 1 µM.

Significantly, the simultaneous presence of DOPC and Cholesterol was found to result in a hydrophobic nucleic acid complexing with neutral lipid formulations (FIG. 16). As low as 1:5 weight (lipid to oligonucleotide) ratio was found to be sufficient to produce a significant fraction of encapsulated oligonucleotide. In the context of DOPC:Cholesterol formulation, other neutral lipids can be added without interfering with particle formation. For example, DOPC:cholesterol: DOPE. FIG. 17 demonstrates that DSPC (saturated fatty acids) can take place of DOPC without any impact on efficiency of complex formation. FIGS. 18-19 present results demonstrating DOPC/Intralipid/Cholesterol formulation containing sd-rxRNA (12386). Complexes were still present when diluted to 500 nM from 1 µM with Accell media (FIG. 18) and when diluted to 500 nM from 5 µM with Accell media (FIG. 19). More RNA appeared to be complexed when diluted to 500 nM from 5 than when diluting to 500 nM from 1 µM.

Figure 20:
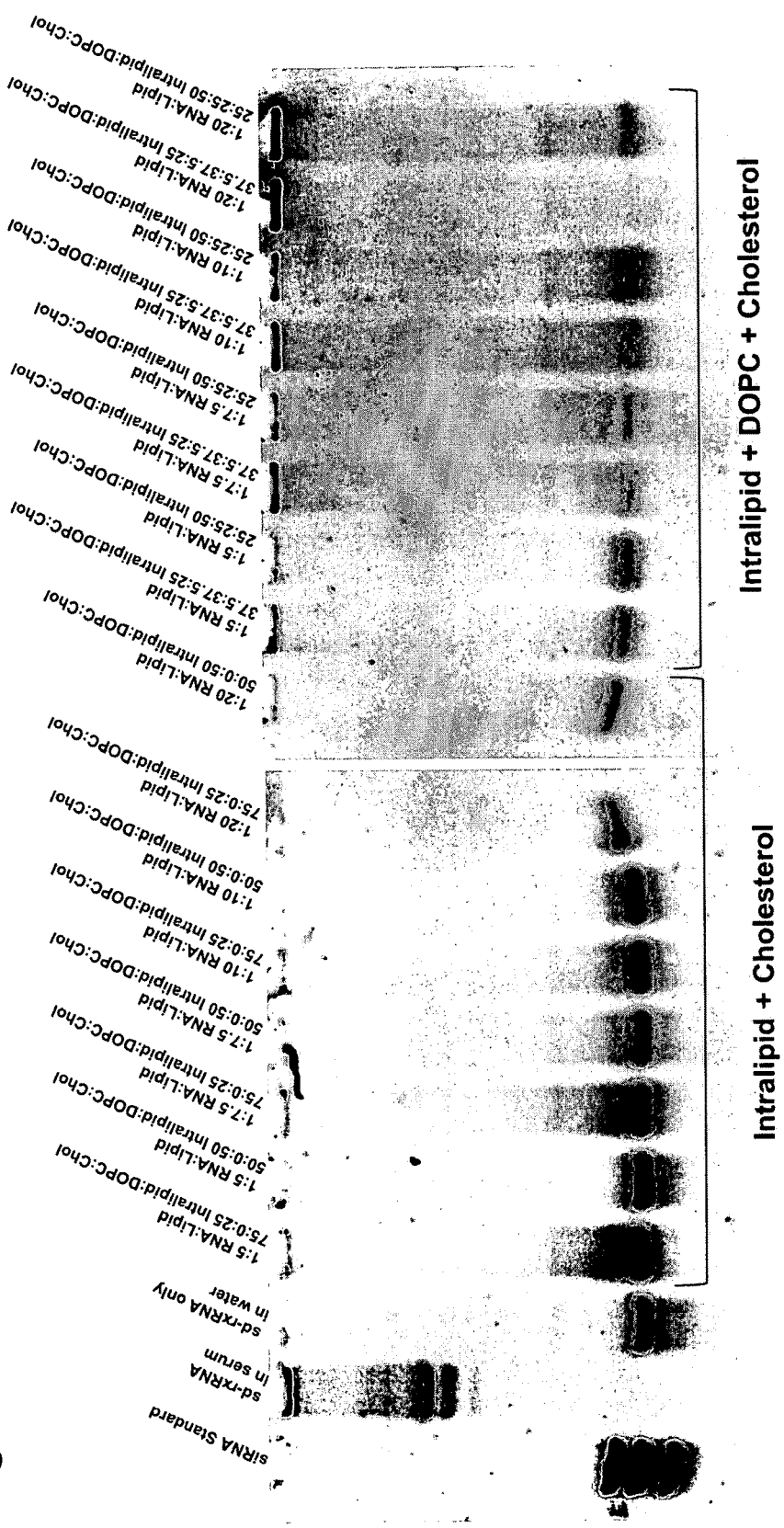
FIG. 20 presents gels demonstrating that the presence of both DOPC and Cholesterol in significant proportions is required to enable significant formation of Intralipid-containing neutral fat/oligo particles. A slight complex formation is observed with Intralipd:cholesterol but it is minor.

FIG. 20 reveals that the presence of both DOPC and Cholesterol in significant proportions was required to enable significant formation of Intralipid-containing neutral fat/oligo particles. A slight complex formation was observed with Intralipd:cholesterol but it was minor compared to the complex formation that occurred in the presence of both DOPC and Cholesterol.

Various additional compounds (i.e., lipids, peptides, small molecules) can be encapsulated into the particle as long as formulation comprises at least 20% of DOPC/Cholesterol-type compounds (FIG. 21). The demonstrated cargo lipid is intralipid. Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. Complexes are formed at different oligonucleotide concentrations, with higher concentrations favoring more efficient complex formation (FIGS. 21-22).

Figure 23:
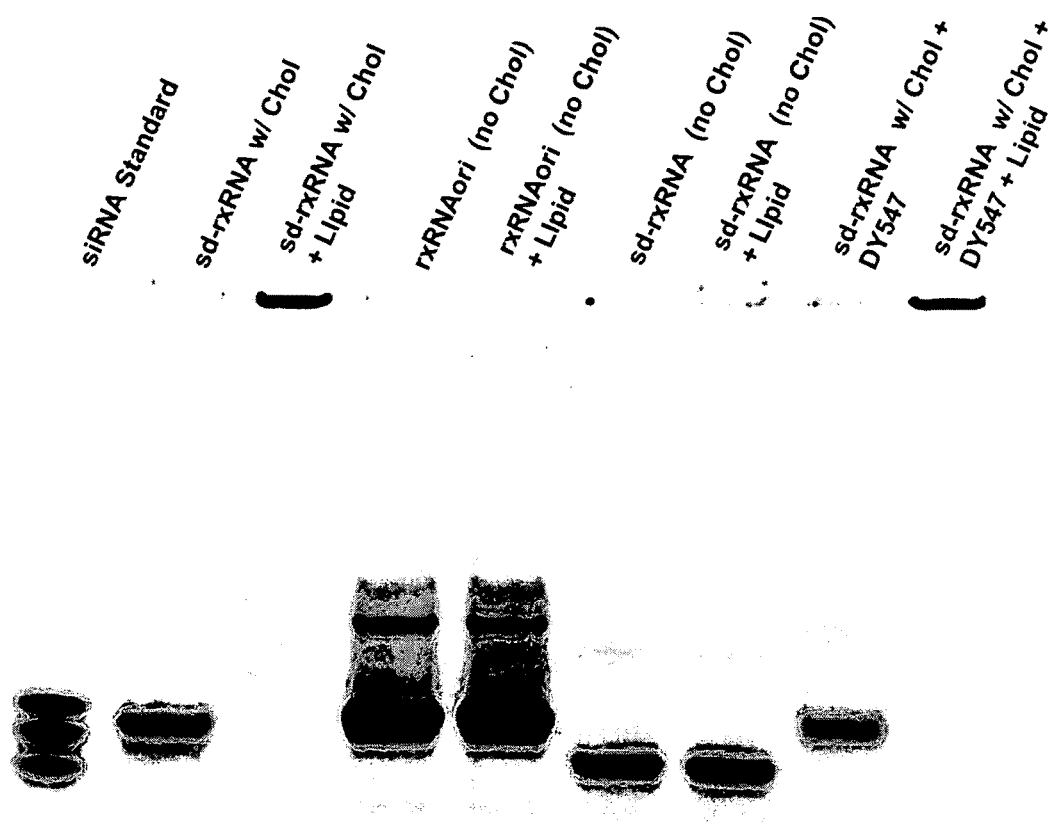
FIG. 23 presents a gel demonstrating that only hydrophobically modified oligonucleotides are complexed with neutral fat formulations. When a cholesterol-modified sd-rxRNA compound was mixed with 50:50 DOPC/Cholesterol formulation, the sd-rxRNA quantitatively entered into a complex. When rxRNA (Omethyl modified siRNA), regular siRNA or sd-rxRNA, without a hydrophobic compound is mixed with the same formulation, no complex was formed, demonstrating that the combination of a hydrophobic modification of the oligonucleotide with neutral fat formulations comprising at least 20% of DOPC:Cholesterol-type compounds are required for efficient encapsulation of oligos into neutral fat formulations.

Only hydrophobically modified oligonucleotides were found to form complexes with neutral fat formulations (FIG. 23). When a cholesterol-modified sd-rxRNA compound was mixed with 50:50 DOPC/Cholesterol formulation, the sd-rxRNA quantitatively entered into a complex. When rxRNA (Omethyl modified siRNA), regular siRNA or sd-rxRNA, without a hydrophobic compound is mixed with the same formulation, no complex was formed, demonstrating that the combination of a hydrophobic modification of the oligonucleotide with neutral fat formulations comprising at least 20% of DOPC:Cholesterol-type compounds are required for efficient encapsulation of oligonucleotides into neutral fat formulations.

Neutral lipid based formulations were found to enter cells (i.e., HeLa cells) and effectively silence genes (FIG. 24). FIG. 24B demonstrates that the oligonucleotide/lipid ratio and formulation composition affects the level of silencing. Significantly, no toxicity was observed even at 1 uM concentration. This lack of toxicity is a significant improvement over positively charged traditional formulations (i.e., lipofectamine) which exhibit a drastic toxicity at a much lower dose range. This data demonstrates that neutral fat/oligonucleotide formulations are non toxic or have highly reduced toxicity relative to previously described positively charged formulations, and have a wider therapeutic index.

Figure 25:
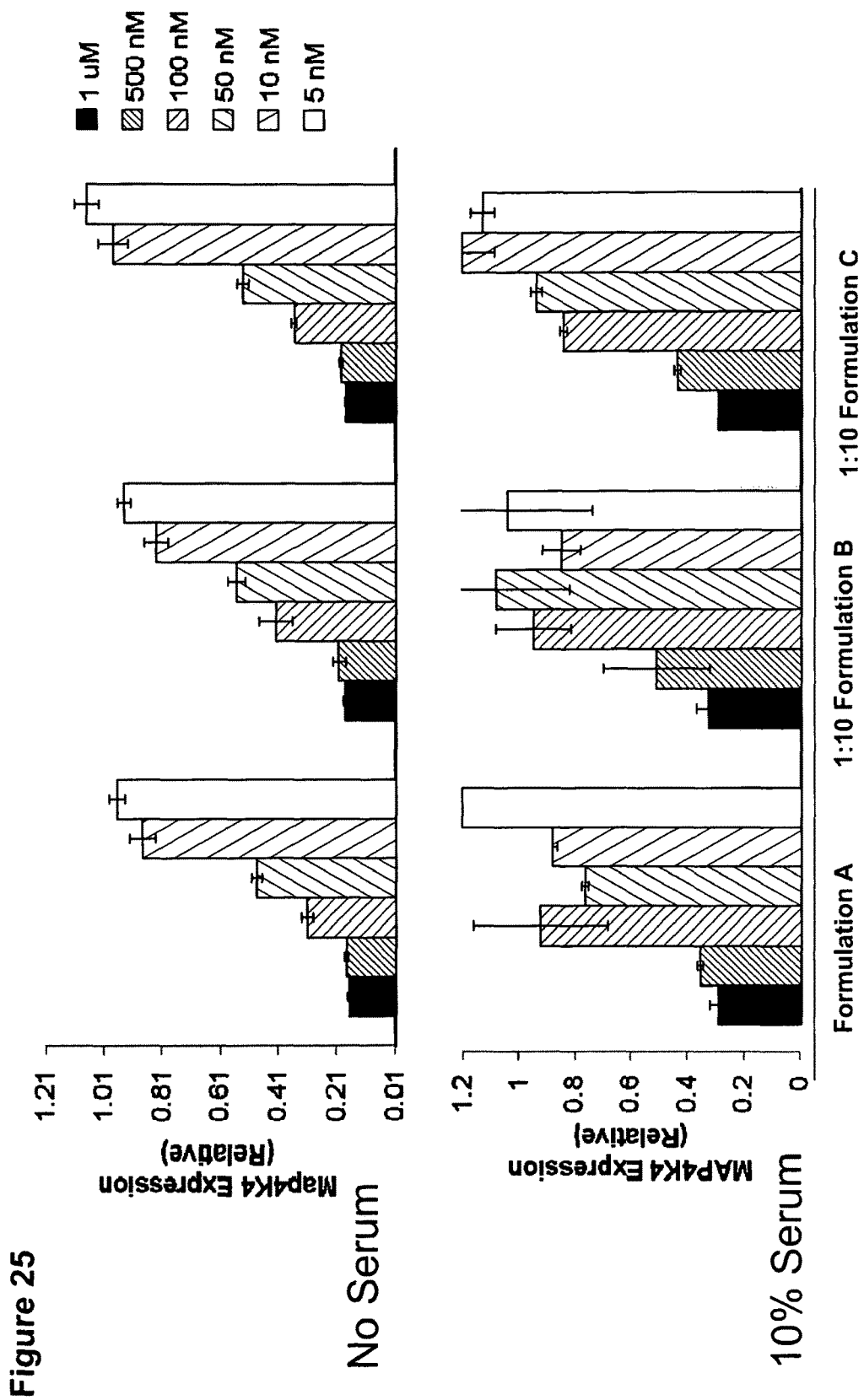
FIG. 25 presents a graph demonstrating various the efficacies of various formulations in vitro with and without serum. Formulation B is DOPC-Cholesterol 50:50; Formulation C is DOPC-DOPE:Cholesterol 33:33:33.

FIG. 25 demonstrates the efficacies of various formulations in achieving gene silencing in vitro with and without serum. Formulation B is DOPC-Cholesterol 50:50 and Formulation C is DOPC-DOPE:Cholesterol 33:33:33.

Figure 27:
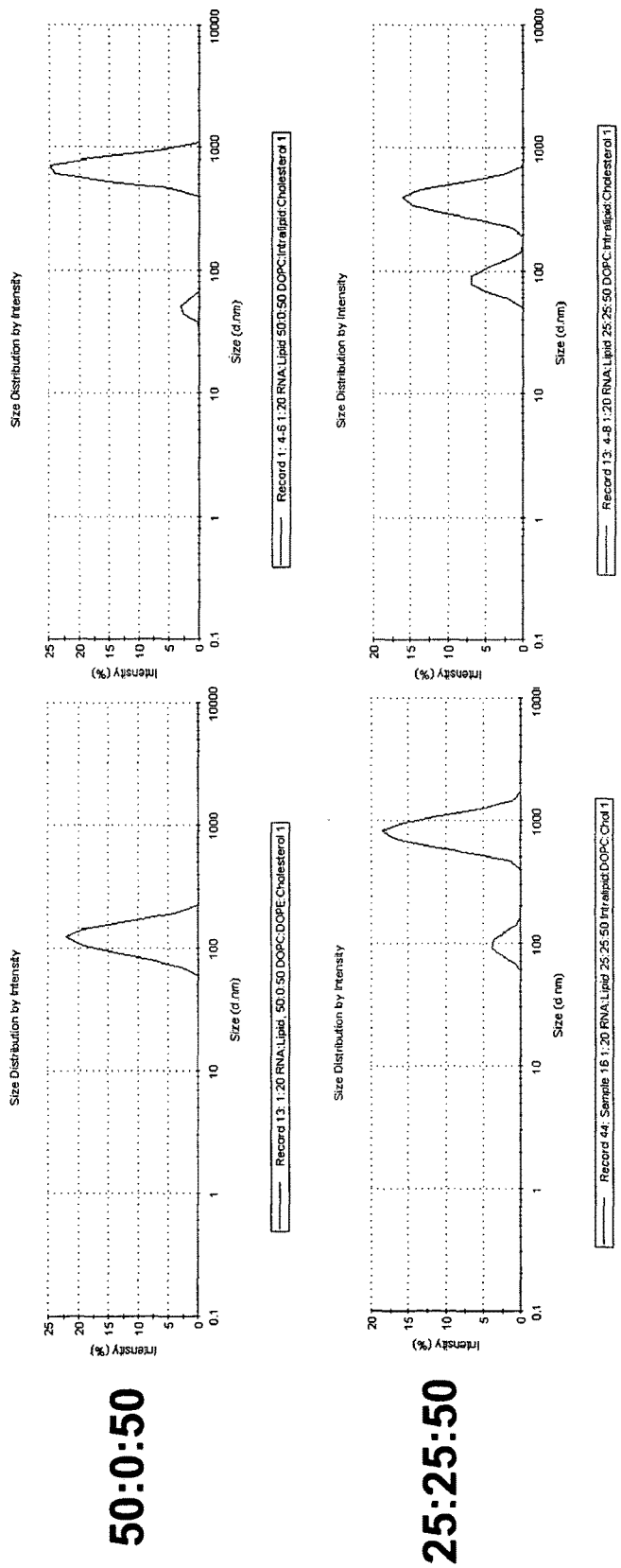
FIG. 27 presents graphs demonstrating size and zeta potential of particles formed upon complexing of neutral fat formulations with hydrophobically modified oligos. While neutral fat by itself forms agglomerates ~500-1000 nm in size, addition of increasing concentrations of an oligonucleotide results in the formation of stable small particles (around 60-120 nm) which are not charged (Zeta Potential ~−10). The neutral particles, sized around 50-100 nM, are ideal for systemic administration. The size and charge of the particles is affected by the oligonucleotide/lipid ratio, lipid mixture composition and lipid ratios within formulation.

FIGS. 26-27 present data on the size and zeta potential of particles formed upon complexing of neutral fat formulations with hydrophobically modified oligos. While neutral fat by itself forms agglomerates ~500-1000 nm in size, addition of increasing concentrations of an oligonucleotide results in the formation of stable small particles (around 60-120 nm) which are not charged (Zeta Potential ~–10). The neutral particles, sized around 50-100 nM, are ideal for systemic administration. The size and charge of the particles is affected by the oligonucleotide/lipid ratio, lipid mixture composition and lipid ratios within formulation.

Figure 29:
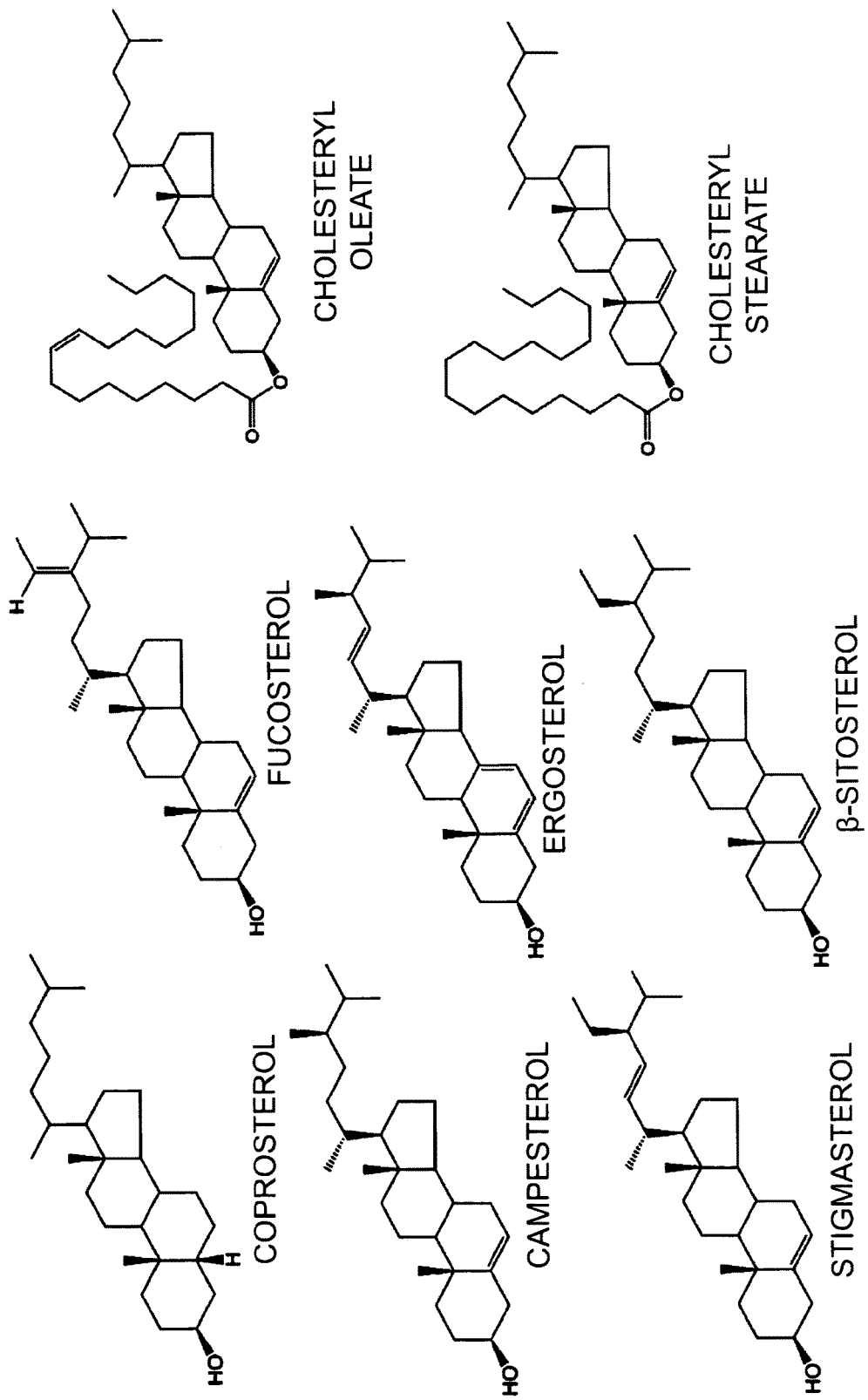
FIG. 29 presents schematics demonstrating sterol-type molecules used for formulation preparations. In some instances, some of the formulations comprising longer chain sterol type molecules have a significantly better cellular uptake and tissue distribution properties
Figure 30:
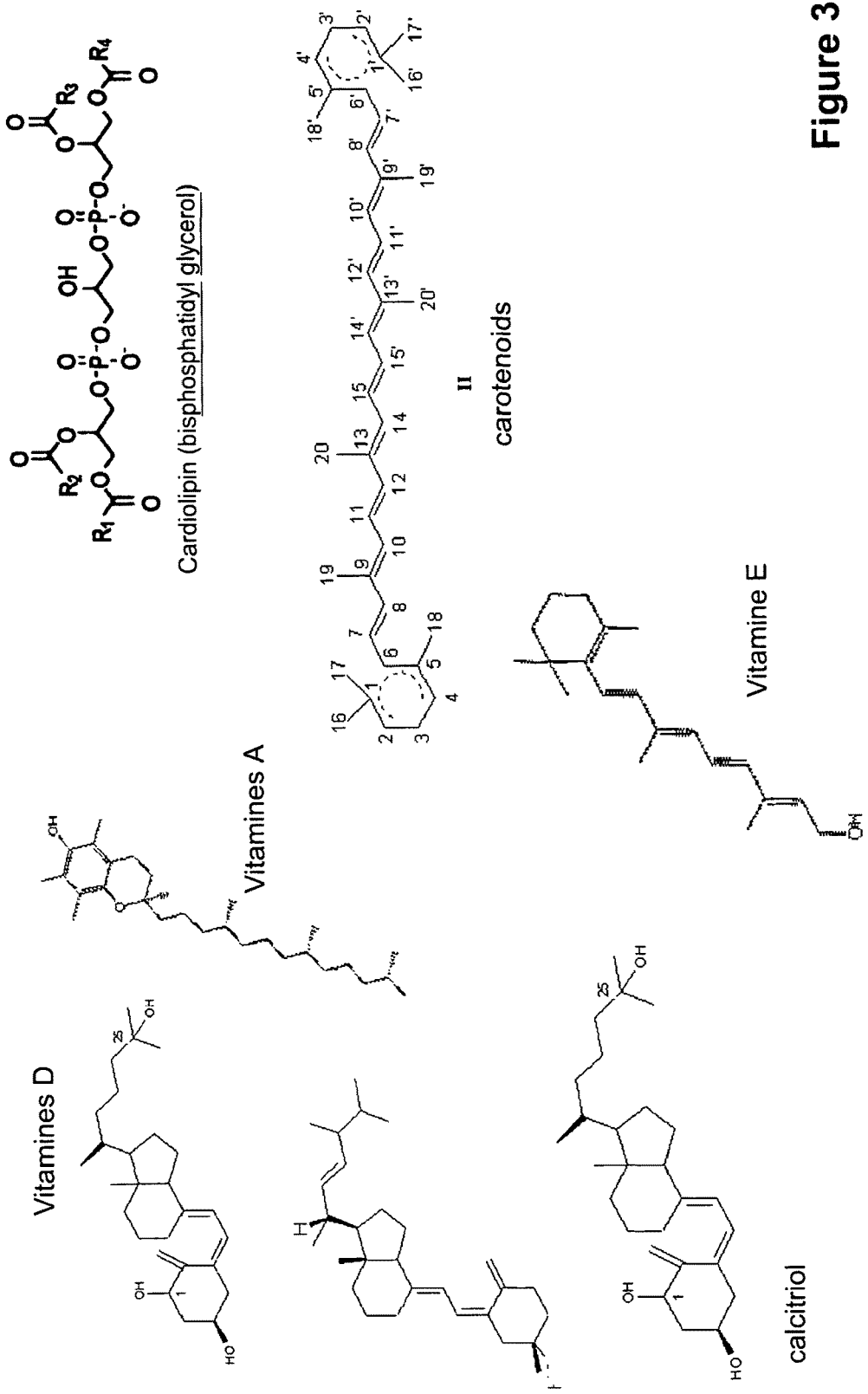
FIG. 30 presents schematics demonstrating some hydrophobic molecules which can be linked to an oligonucleotide or included as part of a formulation to improve or alter cellular uptake and tissue distribution.
Figure 31:
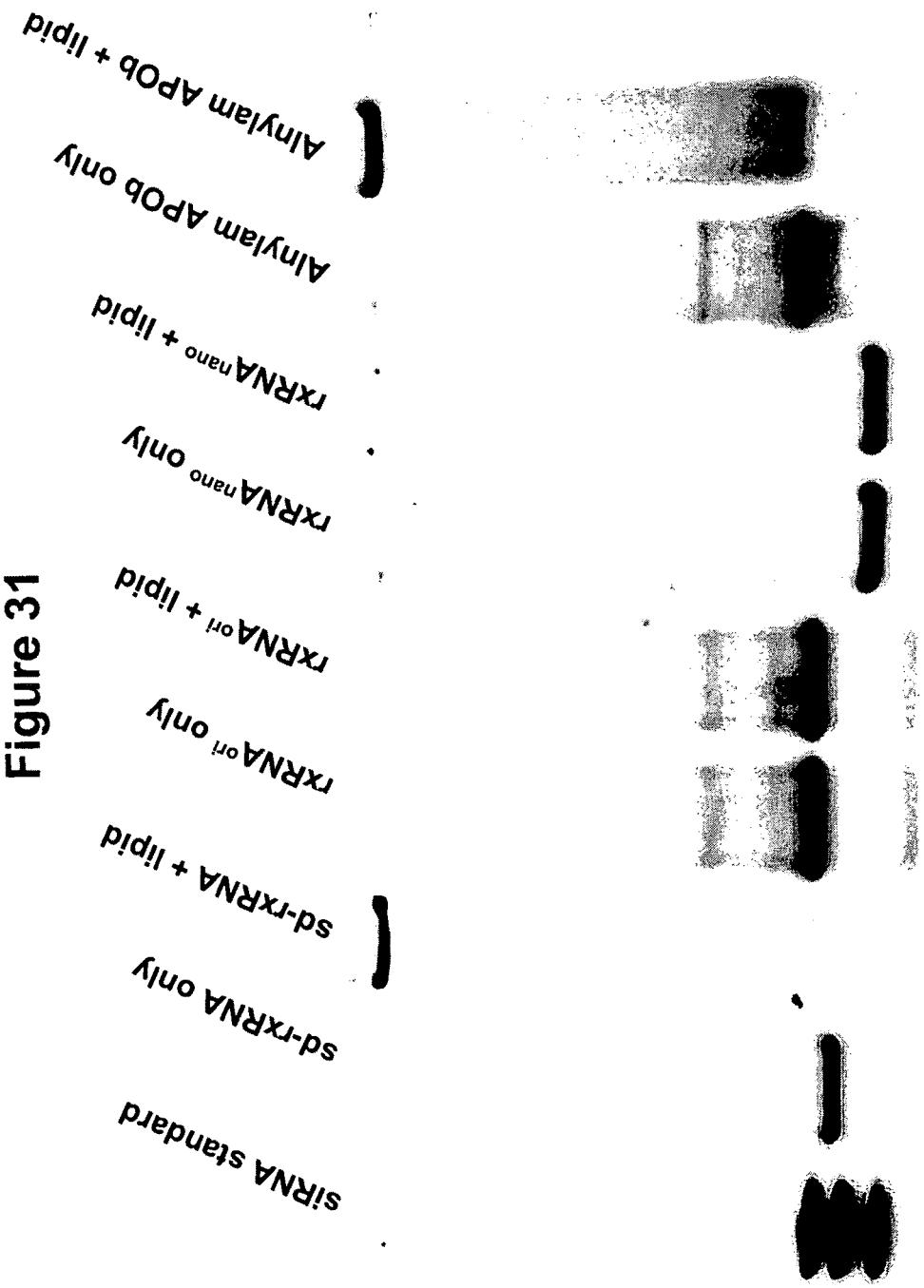
FIG. 31 presents evidence that the presence of a hydrophobic conjugate is sufficient to get an oligonucleotide formulated in a neutral fat formulation. In particular, sd-rxRNA and cholesterol conjugated siRNA (labeled as Alnylam) both form effective complexes, while the non hydrophobically modified oligo does not. It is worth noting that sd-rxRNA complex incorporation was more efficient with sd-rxRNA rather than regular cholesterol conjugated siRNA. It may be due to better hydrophobicity of the compound.
Figure 32:
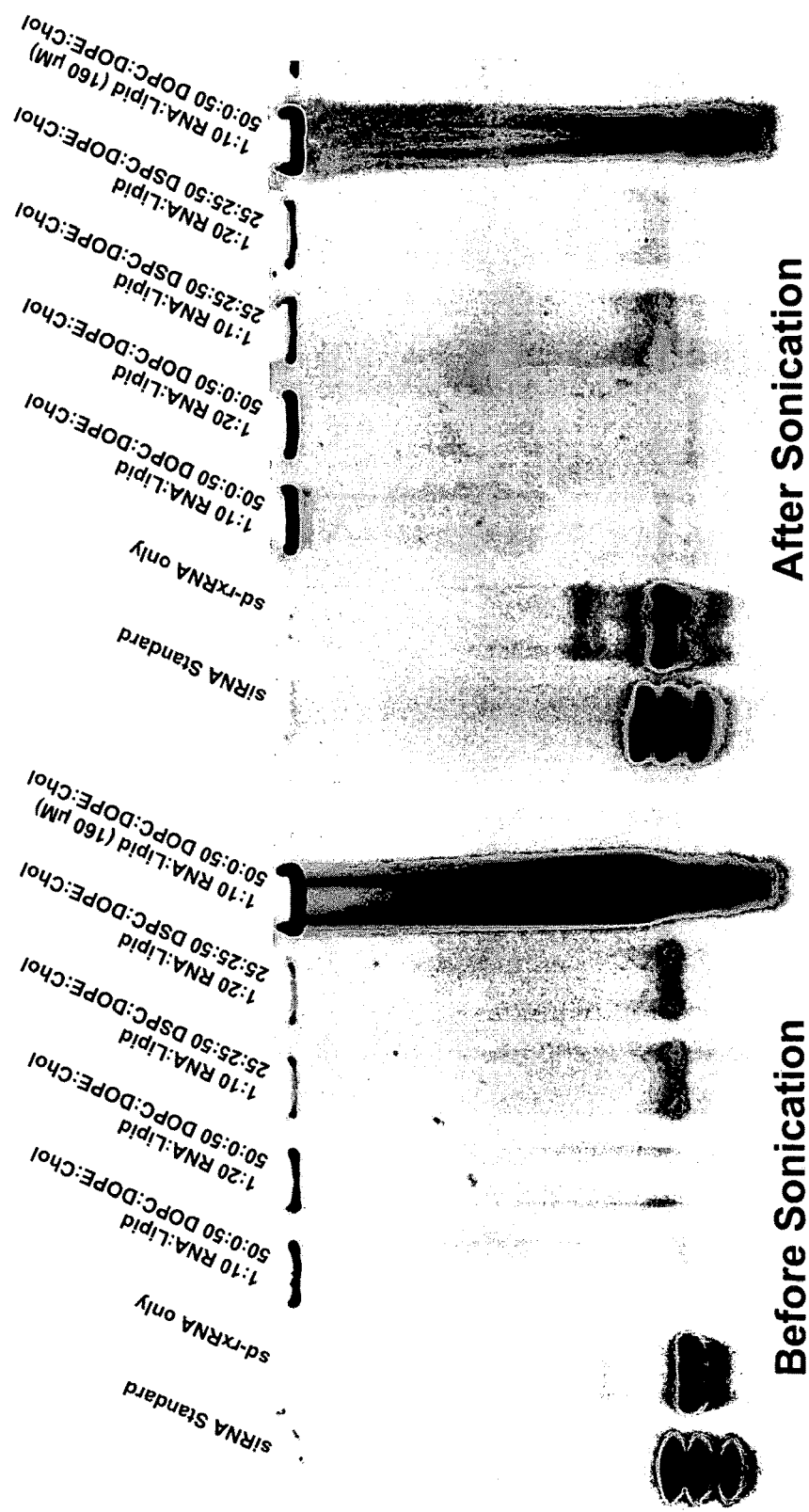
FIG. 32 presents evidence of efficient incorporation of hydrophobic oligos into neutral fat formulations at high concentrations (160 uM). This concentration enables oligo administration at 20 ng/kg in vivo. The Figure further demonstrates that use of sonication might be beneficial for improving the particle size and distribution.
Figure 33:
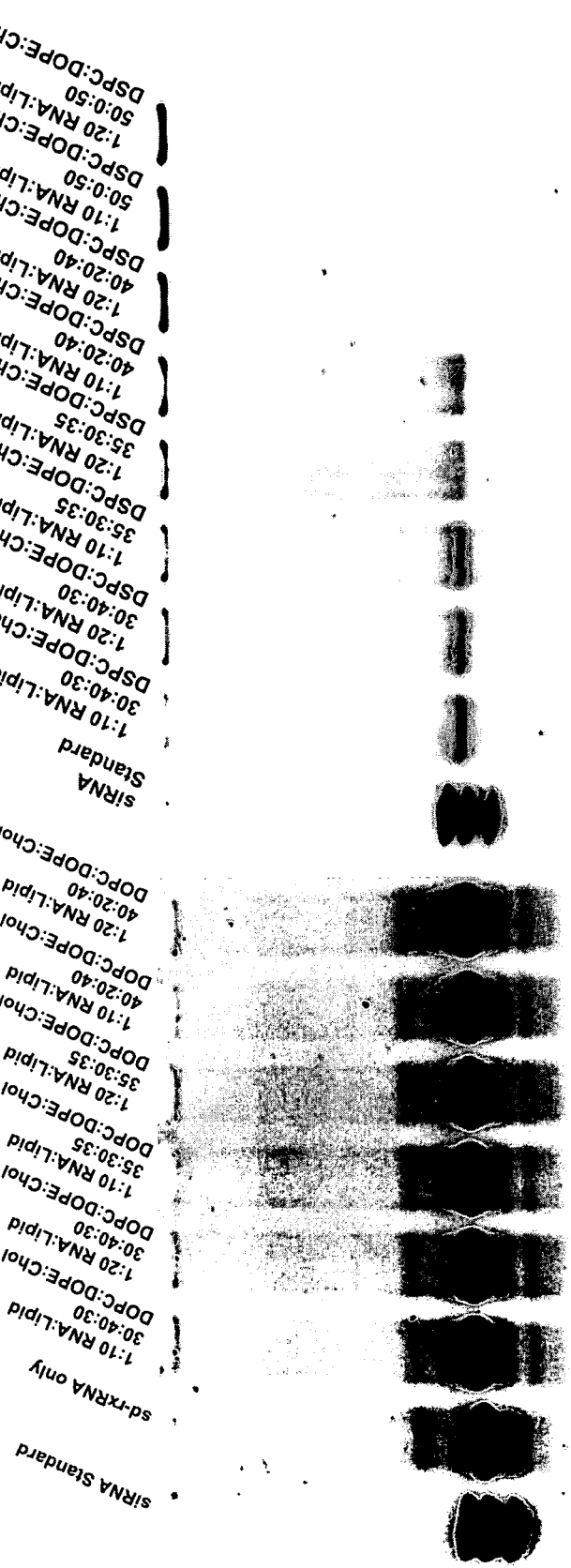
FIG. 33 presents data demonstrating that DSPC is more effective in formation of hydrophobic oligonucleotide containing DOPE containing particles than DOPC. The DSPC and DOPC are highly similar molecule with only difference of the single double bone. Apparently these compounds are different in ability to tolerate DOPE as a cargo molecule. We expect that optimization of the fatty acid structure of choline derivative is important for optimizing the formulation for different cargo load and tissue distribution properties.
Figure 34:
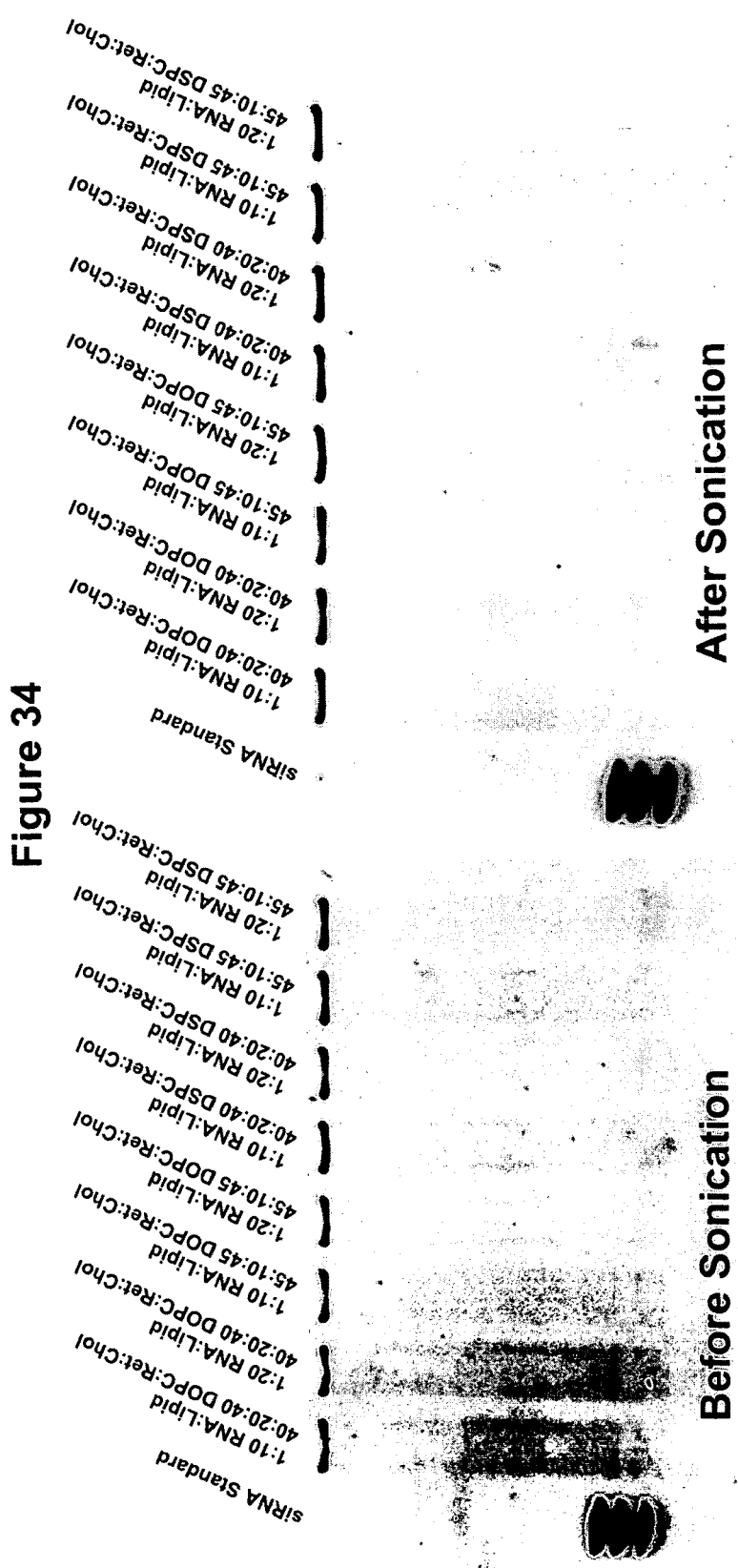
FIG. 34 presents data showing a highly effective complex formation using DOPC:Retinol and Cholesterol. Surprisingly the presence of Retinol improved the complex formation and is expected to change tissue distribution profiles. This data further support the notion that optimizing of the chemical composition of the formulation is important.
Figure 35:
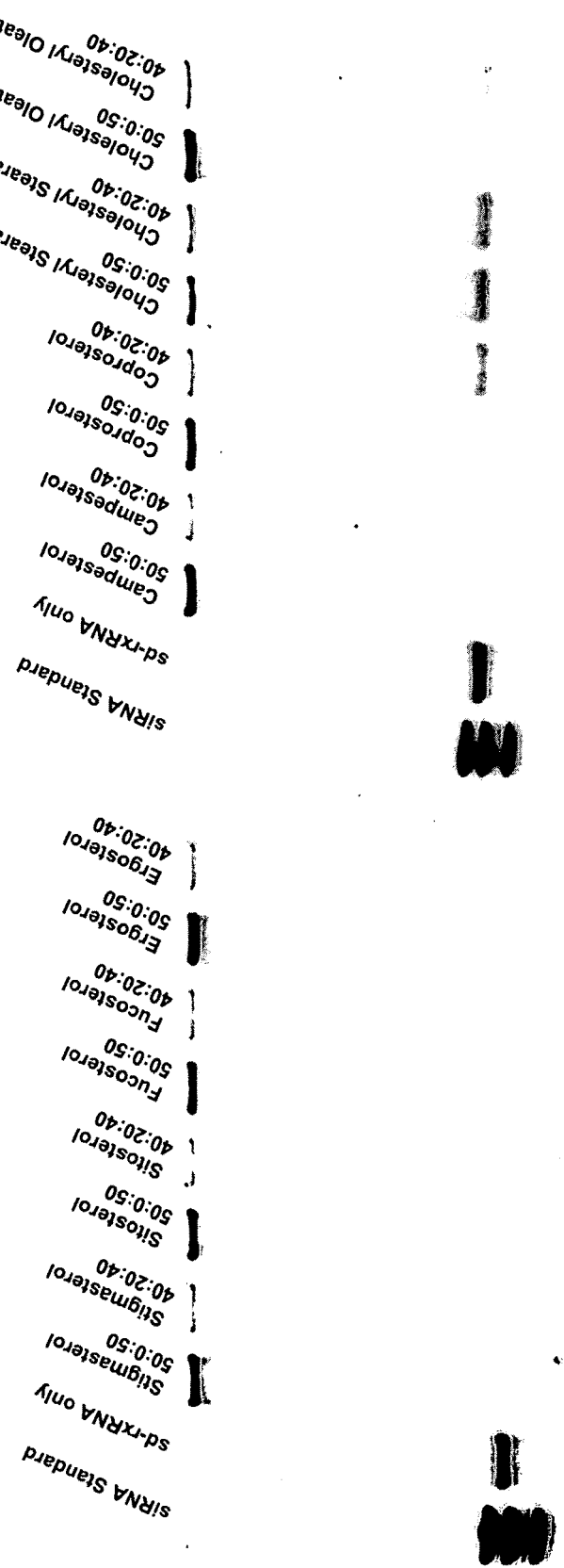
FIG. 35 presents data demonstrating that a variety of sterol type molecules are effectively incorporated in neutral fat formulations. Interestingly use of cholesteryl oleate actually improved the extent of the complex formation. It is expected that chemical diversity of sterol type compounds is important for cargo loading and tissue distribution and cellular uptake.
Figure 36:
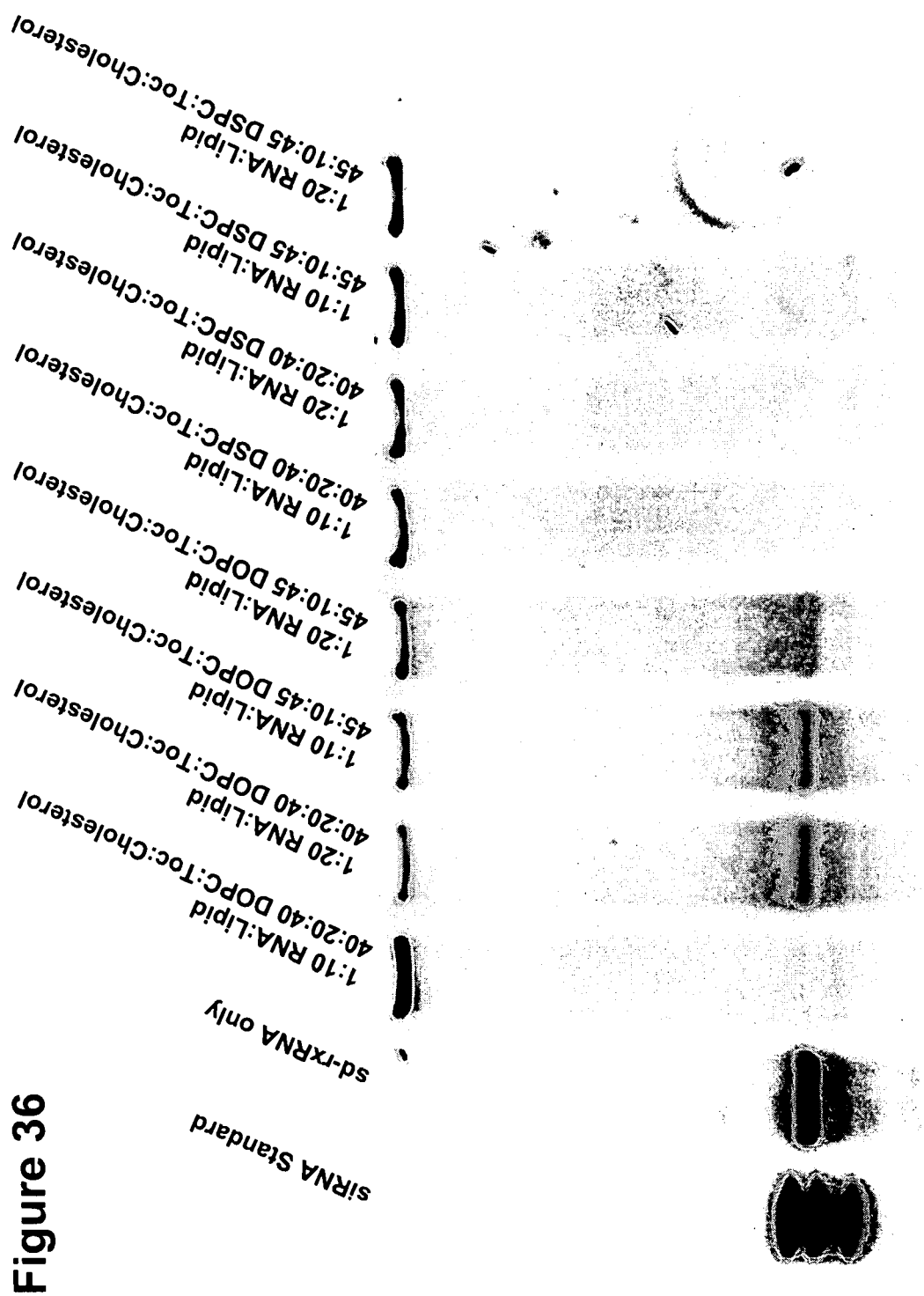
FIG. 36 demonstrates efficient incorporation of tochopherol in hydrophobic oligo: neutral fat formulations.

A panel of lipids used for formulation preparations is demonstrated in FIG. 28, and schematics of the sterol-type molecules used for formulation preparations is demonstrated in FIG. 29. In some instances, some of the formulations comprising longer chain sterol type molecules have a significantly better cellular uptake and tissue distribution properties. FIG. 30 demonstrates examples of hydrophobic molecules that can be linked to a nucleic acid or included as part of a formulation to improve or alter cellular uptake and tissue distribution.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A composition comprising:
a hydrophobic modified polynucleotide, wherein the hydrophobic modified polynucleotide comprises an isolated double stranded nucleic acid molecule comprising a guide strand and a passenger strand, wherein the isolated double stranded nucleic acid molecule includes a double stranded region and a single stranded region, wherein the double stranded region is from 8-14 nucleotides long, wherein the single stranded region is at the 3' end of the guide strand and is 4-12 nucleotides long, wherein the single stranded region contains 3, 4, 5, 6, 7, 8, 9, 10, 11 or 12 phosphorothioate modifications, wherein at least 40% of the nucleotides of the isolated double stranded nucleic acid molecule are modified, and wherein a hydrophobic conjugate is attached to the isolated double stranded nucleic acid molecule at the 3' end of the sense strand, and wherein the isolated double stranded nucleic acid molecule does not form a hairpin;
a neutral fatty mixture comprising at least 20% dioleoyl-phosphatidylcholine (DOPC) or distearoylphosphatidylcholine (DSPC), and at least 20% sterol; and
optionally a cargo molecule,
wherein the hydrophobic modified polynucleotide and the neutral fatty mixture forms a micelle.

2. The composition of claim 1, wherein the polynucleotide is RNA.

3. The composition of claim 1, wherein the neutral fatty mixture comprises at least 25% DOPC or 25% DSPC.

4. The composition of claim 3, wherein the neutral fatty mixture comprises at least 25% sterol.

5. The composition of claim 1, wherein the composition includes at least 20% DOPC and at least 20% cholesterol.

6. A method of inducing RNAi in a cell comprising:
contacting a cell with a composition of claim 1, wherein the polynucleotide has at least a region of sequence correspondence to a target gene and wherein the polynucleotide induces RNAi of mRNA of the target gene.

7. A method of inducing RNAi in a subject in need thereof comprising:
administering to the subject an effective amount for inducing RNAi of mRNA of a target gene, a composition of claim 1, wherein the polynucleotide has at least a region of sequence correspondence to the target gene.

8. The method of claim 7, wherein the subject is a human.

9. A method for delivering a polynucleotide to a target tissue of a subject in need thereof, comprising
administering to the subject a composition of claim 1 wherein the composition includes a fatty acid in the neutral fatty mixture or cargo molecule associated with targeting to the target tissue in order to deliver the polynucleotide to the target tissue in an amount effective to deliver the polynucleotide to the target tissue.

10. A method of inducing RNAi in a subject in need thereof comprising:
administering to the subject an effective amount for inducing RNAi of mRNA of a target gene, a composition of claim 1, wherein the polynucleotide has at least a region of sequence correspondence to the target gene, wherein the step of administering is systemic, intravenous, intraperitoneal, intradermal, topical, intranasal, inhalation, oral, intramucosal or intraocular.

11. The composition of claim 1, wherein each of the at least 40% of nucleotides independently comprises a chemical modification selected from the group consisting of 2' d, 2'OMe, 2'F, hydrophobic and phosphorothioate.

12. The composition of claim 1, wherein the cargo molecule is an intralipid or a nutralipid.

13. The composition of claim 1, wherein the cargo molecule is a fatty acid mixture containing more than 74% linoleic acid, a fatty acid mixture containing at least 6% of cardiolipin, or a fatty acid mixture containing at least 74% linoleic acid and at least 6% of cardiolipin.

14. The composition of claim 1, wherein the cargo molecule is a fusogenic lipid.

15. The composition of claim 14, wherein the fusogenic lipid is DOPE.

* * * * *

SEQUENCE LISTING

<160> NUMBER OF SEQ ID NOS: 5

<210> SEQ ID NO 1
<211> LENGTH: 25
<212> TYPE: RNA
<213> ORGANISM: Artificial Sequence -continued

```
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (1)..(12)
<223> OTHER INFORMATION: 2-O-methyl
<220> FEATURE:
<221> NAME/KEY: misc_feature
<222> LOCATION: (16)..(25)
<223> OTHER INFORMATION: 2-O-methyl
<220> FEATURE:
<221> NAME/KEY: misc_feature
<222> LOCATION: (25)..(25)
<223> OTHER INFORMATION: 3'-cholesterol

<400> SEQUENCE: 1
cuuugaagag uucuguggaa gucua                                           25

<210> SEQ ID NO 2
<211> LENGTH: 25
<212> TYPE: RNA
<213> ORGANISM: Artificial sequence
<220> FEATURE:
<223> OTHER INFORMATION: synthetic oligonucleotide

<400> SEQUENCE: 2
uagacuucca cagaacucuu caaag                                           25

<210> SEQ ID NO 3
<211> LENGTH: 25
<212> TYPE: RNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (20)..(25)
<223> OTHER INFORMATION: phosphorothioate linkage

<400> SEQUENCE: 3
uagacuucca cagaacucuu caaag                                           25

<210> SEQ ID NO 4
<211> LENGTH: 23
<212> TYPE: RNA
<213> ORGANISM: Artificial sequence
<220> FEATURE:
<223> OTHER INFORMATION: syntehtic oligonucleotide
<220> FEATURE:
<221> NAME/KEY: misc_feature
<222> LOCATION: (1)..(23)
<223> OTHER INFORMATION: 2-O-methyl
<220> FEATURE:
<221> NAME/KEY: misc_feature
<222> LOCATION: (20)..(23)
<223> OTHER INFORMATION: phosphorothioate linkage
<220> FEATURE:
<221> NAME/KEY: misc_feature
<222> LOCATION: (23)..(23)
<223> OTHER INFORMATION: 3'-cholesterol

<400> SEQUENCE: 4
acaaacacca uugucacacu cca                                             23

<210> SEQ ID NO 5
<211> LENGTH: 13
<212> TYPE: RNA
```

```
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2-O-methyl
<220> FEATURE:
<221> NAME/KEY: misc_feature
<222> LOCATION: (4)..(4)
<223> OTHER INFORMATION: 2-O-methyl
<220> FEATURE:
<221> NAME/KEY: misc_feature
<222> LOCATION: (10)..(12)
<223> OTHER INFORMATION: 2-O-methyl

<400> SEQUENCE: 5
cuguggaagu cua                                                      13
```